United States Patent
Chen et al.

(10) Patent No.: US 11,129,871 B1
(45) Date of Patent: Sep. 28, 2021

(54) COMPOSITIONS AND METHODS FOR TREATING AND PREVENTING ENDOPLASMIC RETICULUM (ER) STRESS-MEDIATED KIDNEY DISEASES

(71) Applicants: Ying Chen, St. Louis, MO (US);
Fumihiko Urano, St. Louis, MO (US);
Yeawon Kim, St. Louis, MO (US);
Sun-Ji Park, St. Louis, MO (US)

(72) Inventors: Ying Chen, St. Louis, MO (US);
Fumihiko Urano, St. Louis, MO (US);
Yeawon Kim, St. Louis, MO (US);
Sun-Ji Park, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 16/446,073

(22) Filed: Jun. 19, 2019

Related U.S. Application Data

(60) Provisional application No. 62/828,514, filed on Apr. 3, 2019, provisional application No. 62/686,705, filed on Jun. 19, 2018.

(51) Int. Cl.
*A61K 38/17* (2006.01)
*A61P 13/12* (2006.01)
*A61K 31/554* (2006.01)

(52) U.S. Cl.
CPC ........ *A61K 38/1709* (2013.01); *A61K 31/554* (2013.01); *A61P 13/12* (2018.01)

(58) Field of Classification Search
None
See application file for complete search history.

(56) References Cited

U.S. PATENT DOCUMENTS 7,704,990 B2 4/2010 Landry et al.

OTHER PUBLICATIONS

Park et al. "Endoplasmic reticulum stress and monogenic kidney diseases in precision nephrology" Pediatric Nephrology 34:1493-1500. (Year: 2018).*
Kim et al. "Mesencephalic astrocyte-derived neurotrophic factor (MANF), a new player in endoplasmic reticulum diseases: structure, biology and therapeutic roles" Transl. Res. 188:1-9. (Year: 2017).*
Lisy et al. "New Cardioprotective Agent K201 Is Natriuretic and Glomerular Filtration Rate Enhancing" Circulation 113:246-251. (Year: 2006).*
Anonymous "Minimal Change Disease" National Kidney Foundation kidney.org/atoz/content/minimal-change-disease (Year: 2015).*
Anonymous "Membranous Nephropathy" National Kidney Foundation. kidney.org/atoz/content/membranous-nephropathy-mn.*
Anonymous "Focal Segmental Glomerulosclerosis" National Kidney Foundation. kidney.org/atoz/content/focal (Year: 2014).*
Ismail et al. "Treatment with enalapril and not diltiazem ameliorated progression of chronic kidney disease in rats, and normalized renal AT1 receptor expression as measured with PET imaging" PLoS ONE 12:e0177451. (Year: 2017).*
Airavaara M, Shen H, Kuo C-C, et al. Mesencephalic astrocyte-derived neurotrophic factor reduces ischemic brain injury and promotes behavioral recovery in rats. *J Comp Neurol*. 2009;515(1):116-124. doi:10.1002/cne.22039.
Apostolou A, Shen Y, Liang Y, Luo J, Fang S. Armet, a UPR-upregulated protein, inhibits cell proliferation and ER stress-induced cell death. *Exp Cell Res*. 2008;314(13):2454-2467. doi:10.1016/j.yexcr.2008.05.001.
Bek MF, Bayer M, Müller B, et al. Expression and function of C/EBP homology protein (GADD153) in podocytes. *Am J Pathol*. 2006; 168(1):20-32. doi:10.2353/ajpath.2006.040774.
Bernascone I, Janas S, Ikehata M, et al. A transgenic mouse model for uromodulin-associated kidney diseases shows specific tubulo-interstitial damage, urinary concentrating defect and renal failure. *Hum Mol Genet*. 2010;19(15):2998-3010. doi:10.1093/hmg/ddq205.
Bernascone I, Vavassori S, Pentima AD, et al. Defective Intracellular Trafficking of Uromodulin Mutant Isoforms. *Traffic*. 2006;7(11):1567-1579. doi:10.1111/j. 1600-0854.2006.00481.x.
Chen YM, Kikkawa Y, Miner JH. A Missense LAMB2 Mutation Causes Congenital Nephrotic Syndrome by Impairing Laminin Secretion. *J Am Soc Nephrol*. 2011;22(5):849-858. doi:10.1681/ASN.2010060632.
Chen YM, Zhou Y, Go G, Marmerstein JT, Kikkawa Y, Miner JH. Laminin β32 gene missense mutation produces endoplasmic reticulum stress in podocytes. *J Am Soc Nephrol*. 2013;24(8):1223-1233. doi:10.1681/ASN.2012121149.
Cozzolino M, Gentile G, Mazzaferro S, Brancaccio D, Ruggenenti P, Remuzzi G. Blood pressure, proteinuria, and phosphate as risk factors for progressive kidney disease: a hypothesis. *Am J Kidney Dis*. 2013;62(5):984-992. doi:10.053/j.ajkd.2013.02.379.
Cybulsky AV. Endoplasmic reticulum stress, the unfolded protein response and autophagy in kidney diseases. *Nat Rev Nephrol*. 2017;13(11):681-696. doi:10.1038/nrneph.2017.129.
Cybulsky AV, Takano T, Papillon J, Bijian K, Guillemette J, Kennedy CRJ. Glomerular epithelial cell injury associated with mutant alpha-actinin-4. *Am J Physiol Renal Physiol*. 2009;297(4):F987-995. doi:10.1152/ajprenal.00055.2009.
Dincer UD. Cardiac ryanodine receptor in metabolic syndrome: is JTV519 (K201) future therapy? *Diabetes Metab Syndr Obes*. 2012;5:89-99. doi:10.2147/DMSO.S30005.
Drozdova T, Papillon J, Cybulsky AV. Nephrin missense mutations: induction of endoplasmic reticulum stress and cell surface rescue by reduction in chaperone interactions. *Physiol Rep*. 2013;1(4):e00086. doi:10.1002/phy2.86.

(Continued)

*Primary Examiner* — Sudhakar Katakam
*Assistant Examiner* — Zachary J Miknis

(57) ABSTRACT

Among the various aspects of the present disclosure is the provision of methods and compositions to treat or prevent an endoplasmic reticulum (ER) stress-mediated kidney disease in a subject, the method comprising administering to the subject a pharmaceutical composition comprising a therapeutically effective amount of an ER calcium channel stabilizing agent or an ER stress modulating agent (e.g., mesencephalic astrocyte-derived neurotrophic factor (MANF), compound K201).

9 Claims, 46 Drawing Sheets

Specification includes a Sequence Listing.

(56) References Cited

OTHER PUBLICATIONS

Ellgaard L, Helenius A. Quality control in the endoplasmic reticulum. *Nat Rev Mol Cell Biol.* 2003;4(3):181-191. doi:10.1038/nrm1052.
Fan Q, Zhang H, Ding J, et al. R168H and V165X mutant podocin might induce different degrees of podocyte injury via different molecular mechanisms. *Genes to Cells.* 2009; 14(9):1079-1090. doi:10.1111/j.1365-2443.2009.01336.x.
Fill M, Copello JA. Ryanodine receptor calcium release channels. *Physiol Rev.* 2002;82(4):893-922. doi:10.1152/physrev.00013.2002.
Gast C, Marinaki T, Arenas-Hernandez M, Campbell S, Venkat-Raman G. Genetic Testing Reveals Increased Prevalence of Uromodulin Associated Kidney Disease. *Nephrol Dial Transplant.* 2015;30(suppl_3):iii56-iii56. doi:10.1093/ndt/gfv160.05.
Gast C, Pengelly RJ, Lyon M, et al. Collagen (COL4A) mutations are the most frequent mutations underlying adult focal segmental glomerulosclerosis. *Nephrol Dial Transplant.* 2016;31(6):961-970. doi:10.1093/ndt/gfv325.
Glembotski CC, Thuerauf DJ, Huang C, Vekich JA, Gottlieb RA, Doroudgar S. Mesencephalic astrocyte-derived neurotrophic factor protects the heart from ischemic damage and is selectively secreted upon sarco/endoplasmic reticulum calcium depletion. *J Biol Chem.* 2012;287(31):25893-25904. doi:10.1074/jbc.M112.356345.
Harding HP, Novoa I, Zhang Y, et al. Regulated translation initiation controls stress-induced gene expression in mammalian cells. *Mol Cell.* 2000;6(5):1099-1108. doi:10.1016/s1097-2765(00)00108-9.
Hassan H, Tian X, Inoue K, et al. Essential Role of X-Box Binding Protein-1 during Endoplasmic Reticulum Stress in Podocytes. *J Am Soc Nephrol.* 2016;27(4):1055-1065. doi:10.1681/ASN.2015020191.
Henderson MJ, Richie CT, Airavaara M, Wang Y, Harvey BK. Mesencephalic astrocyte-derived neurotrophic factor (MANF) secretion and cell surface binding are modulated by KDEL receptors. *J Biol Chem.* 2013;288(6):4209-4225. doi:10.1074/jbc.M112.400648.
Henderson MJ, Wires ES, Trychta KA, Richie CT, Harvey BK. SERCaMP: a carboxy-terminal protein modification that enables monitoring of ER calcium homeostasis. *Mol Biol Cell.* 2014;25(18):2828-2839. doi:10.1091/mbc.E14-06-1141.
Hetz C, Mollereau B. Disturbance of endoplasmic reticulum proteostasis in neurodegenerative diseases. *Nat Rev Neurosci.* 2014;15(4):233-249. doi:10.1038/nrn3689.
Heymann J, Winkler CA, Hoek M, Susztak K, Kopp JB. Therapeutics for APOL1 nephropathies: putting out the fire in the podocyte. *Nephrol Dial Transplant.* 2017;32(suppl_1):i65-i70. doi:10.1093/ndt/gfw402.
Hinkes BG, Mucha B, Vlangos CN, et al. Nephrotic syndrome in the first year of life: two thirds of cases are caused by mutations in 4 genes (NPHS1, NPHS2, WT1, and LAMB2). *Pediatrics.* 2007;119(4):e907-919. doi:10.1542/peds.2006-2164.
Hoffmann S, Podlich D, Hähnel B, Kriz W, Gretz N. Angiotensin II Type 1 Receptor Overexpression in Podocytes Induces Glomerulosclerosis in Transgenic Rats. *JASN.* 2004;15(6):1475-1487. doi:10.1097/01.ASN.0000127988.42710.A7.
Johnson BG, Dang LT, Marsh G, et al. Uromodulin p.Cys147Trp mutation drives kidney disease by activating ER stress and apoptosis. *J Clin Invest.* 2017;127(11):3954-3969. doi:10.1172/JCI93817.
Ju W, Nair V, Smith S, et al. Tissue transcriptome-driven identification of epidermal growth factor as a chronic kidney disease biomarker. *Sci Transl Med.* 2015;7(316):316ra193. doi:10.1126/scitranslmed.aac7071.
Kemter E, Prueckl P, Sklenak S, et al. Type of uromodulin mutation and allelic status influence onset and severity of uromodulin-associated kidney disease in mice. *Hum Mol Genet.* 2013;22(20):4148-4163. doi:10.1093/hmq/ddt263.
Kim Y, Lee H, Manson SR, et al. Mesencephalic Astrocyte-Derived Neurotrophic Factor as a Urine Biomarker for Endoplasmic Reticulum Stress-Related Kidney Diseases. *J Am Soc Nephrol.* 2016;27(10):2974-2982. doi:10.1681/ASN.2014100986.
Kim Y, Park S-J, Manson SR, et al. Elevated urinary CRELD2 is associated with endoplasmic reticulum stress-mediated kidney disease. *JCI Insight.* 2017;2(23). doi:10.1172/jci.insight.92896.
Kitamura M. Endoplasmic reticulum stress and unfolded protein response in renal pathophysiology: Janus faces. *American Journal of Physiology-Renal Physiology.* 2008;295(2):F323-F334. doi:10.1152/ajprenal.00050.2008.
Kushnir A, Marks AR. The ryanodine receptor in cardiac physiology and disease. *Adv Pharmacol.* 2010;59:1-30. doi:10.1016/S1054-3589(10)59001-X.
Lehtonen S, Ryan JJ, Kudlicka K, Iino N, Zhou H, Farquhar MG. Cell junction-associated proteins IQGAP1, MAGI-2, CASK, spectrins, and alpha-actinin are components of the nephrin multiprotein complex. *Proc Natl Acad Sci USA.* 2005; 102(28):9814-9819. doi:10.1073/pnas.0504166102.
Lindahl M, Danilova T, Palm E, et al. MANF is indispensable for the proliferation and survival of pancreatic β cells. *Cell Rep.* 2014;7(2):366-375. doi:10.1016/j.celrep.2014.03.023.
Lindholm P, Peränen J, Andressoo J-O, et al. MANF is widely expressed in mammalian tissues and differently regulated after ischemic and epileptic insults in rodent brain. *Mol Cell Neurosci.* 2008;39(3):356-371. doi:10.1016/j.mcn.2008.07.016.
Lisy & Burnett. New cardioprotective agent K201 is natriuretic and glomerular filtration rate enhancing. *Circulation.* 2006;113(2):246-251.
Liu L, Doné SC, Khoshnoodi J, et al. Defective nephrin trafficking caused by missense mutations in the NPHS1 gene: insight into the mechanisms of congenital nephrotic syndrome. *Hum Mol Genet.* 2001;10(23):2637-2644. doi:10.1093/hmg/10.23.2637.
Liu X, Betzenhauser MJ, Reiken S, et al. Role of Leaky Neuronal Ryanodine Receptors in Stress-Induced Cognitive Dysfunction. *Cell.* 2012;150(5):1055-1067. doi:10.1016/j.cell.2012.06.052.
Marx SO, Reiken S, Hisamatsu Y, et al. Phosphorylation-dependent regulation of ryanodine receptors: a novel role for leucine/isoleucine zippers. *J Cell Biol.* 2001;153(4):699-708. doi:10.1083/jcb.153.4.699.
Mekahli D, Bultynck G, Parys JB, De Smedt H, Missiaen L. Endoplasmic-Reticulum Calcium Depletion and Disease. *Cold Spring Harb Perspect Biol.* 2011:3(6). doi:10.1101/cshperspect.a004317.
Miner JH, Go G, Cunningham J, Patton BL, Jarad G. Transgenic isolation of skeletal muscle and kidney defects in laminin beta2 mutant mice: implications for Pierson syndrome. *Development.* 2006;133(5):967-975. doi:10.1242/dev.02270.
Mizobuchi N, Hoseki J, Kubota H, et al. ARMET is a soluble ER protein induced by the unfolded protein response via ERSE-II element. *Cell Struct Funct.* 2007;32(1):41-50. doi:10.1247/csf.07001.
Munro S, Pelham HR. An Hsp70-like protein in the ER: identity with the 78 kd glucose-regulated protein and immunoglobulin heavy chain binding protein. *Cell.* 1986;46(2):291-300. doi:10.1016/0092-8674(86)90746-4.
Neves J, Zhu J, Sousa-Victor P, et al. Immune modulation by MANF promotes tissue repair and regenerative success in the retina. *Science.* 2016;353(6294):aaf3646. doi:10.1126/science.aaf3646.
Oh-Hashi K, Tanaka K, Koga H, Hirata Y, Kiuchi K. Intracellular trafficking and secretion of mouse mesencephalic astrocyte-derived neurotrophic factor. *Mol Cell Biochem.* 2012;363(1-2):35-41. doi:10.1007/s11010-011-1155-0.
Oslowski CM, Urano F. Measuring ER stress and the unfolded protein response using mammalian tissue culture system. *Methods Enzymol.* 2011;490:71-92. doi:10.1016/B978-0-12-385114-7.00004-0.
Papazachariou L, Demosthenous P, Pieri M, et al. Frequency of COL4A3/COL4A4 mutations amongst families segregating glomerular microscopic hematuria and evidence for activation of the unfolded protein response. Focal and segmental glomerulosclerosis is a frequent development during ageing. *PLoS ONE.* 2014;9(12):e115015. doi:10.1371/journal.pone.0115015.
Peltier J, Bellocq A, Perez J, et al. Calpain activation and secretion promote glomerular injury in experimental glomerulonephritis: evi-

(56) References Cited

OTHER PUBLICATIONS dence from calpastatin-transgenic mice. *J Am Soc Nephrol.* 2006;17(12):3415-3423. doi:10.1681/ASN.2006050542.
Petrova P, Raibekas A, Pevsner J, et al. MANF: a new mesencephalic, astrocyte-derived neurotrophic factor with selectivity for dopaminergic neurons. *J Mol Neurosci.* 2003;20(2):173-188. doi:10.1385/jmn:20:2:173.
Pieri M, Stefanou C, Zaravinos A, et al. Evidence for activation of the unfolded protein response of collagen IV nephropathies. *J Am Soc Nephrol.* 2014;25(2):260-275. doi:10.1681/ASN.2012121217.
Rampoldi L, Caridi G, Santon D, et al. Allelism of MCKD, FJHN and GCKD caused by impairment of uromodulin export dynamics. *Hum Mol Genet.* 2003;12(24):3369-3384. doi:10.1093/hmg/ddg353.
Reiser J, Polu KR, Möller CC, et al. TRPC6 is a glomerular slit diaphragm-associated channel required for normal renal function. *Nat Genet.* 2005;37(7):739-744. doi:10.1038/ng1592.
Shan J, Betzenhauser MJ, Kushnir A, et al. Role of chronic ryanodine receptor phosphorylation in heart failure and β-adrenergic receptor blockade in mice. *J Clin Invest.* 2010;120(12):4375-4387. doi:10.1172/JCI37649.
Shan J, Kushnir A, Betzenhauser MJ, et al. Phosphorylation of the ryanodine receptor mediates the cardiac fight or flight response in mice. *J Clin Invest.* 2010;120(12):4388-4398. doi:10.1172/JCI32726.
Sonneveld R, Hoenderop JG, Isidori AM, et al. Sildenafil Prevents Podocyte Injury via PPAR-γ-Mediated TRPC6 Inhibition. *J Am Soc Nephrol.* 2017;28(5):1491-1505. doi:10.1681/ASN.2015080885.
Subramanian A, Tamayo P, Mootha VK, et al. Gene set enrichment analysis: A knowledge-based approach for interpreting genome-wide expression profiles. *Proceedings of the National Academy of Sciences.* 2005;102(43): 15545-15550. doi:10.1073/pnas.0506580102.
Takeshima H, Ikemoto T, Nishi M, et al. Generation and characterization of mutant mice lacking ryanodine receptor type 3. *J Biol Chem.* 1996;271(33):19649-19652. doi:10.1074/jbc.271.33.19649.
Tian X, Kim JJ, Monkley SM, et al. Podocyte-associated talin1 is critical for glomerular filtration barrier maintenance. *J Clin Invest.* 2014;124(3):1098-1113. doi:10.1172/JCI69778.
Tunwell Rea, Lai FA. Ryanodine Receptor Expression in the Kidney and a Non-excitable Kidney Epithelial Cell. *J Biol Chem.* 1996;271(47):29583-29588. doi:10.1074/jbc.271.47.29583.

Urano F, Wang X, Bertolotti A, et al. Coupling of Stress in the ER to Activation of JNK Protein Kinases by Transmembrane Protein Kinase IRE1. *Science.* 2000;287(5453):664-666. doi:10.1126/science.287.5453.664.
Vermes I, Haanen C, Steffens-Nakken H, Reutelingsperger C. A novel assay for apoptosis. Flow cytometric detection of phosphatidylserine expression on early apoptotic cells using fluorescein labelled Annexin V. *J Immunol Methods.* 1995;184(1):39-51. doi:10.1016/0022-1759(95)00072-i.
Voutilainen MH, Bäck S, Pörsti E, et al. Mesencephalic astrocyte-derived neurotrophic factor is neurorestorative in rat model of Parkinson's disease. *J Neurosci.* 2009;29(30):9651-9659. doi:10.1523/JNEUROSCI.0833-09.2009.
Vylet'al P, Kublová M, Kalbácová M, et al. Alterations of uromodulin biology: a common denominator of the genetically heterogeneous FJHN/MCKD syndrome. *Kidney Int.* 2006;70(6):1155-1169. doi:10.1038/sj.ki.5001728.
Wehrens XHT, Lehnart SE, Reiken S, Vest JA, Wronska A, Marks AR. Ryanodine receptor/calcium release channel PKA phosphorylation: a critical mediator of heart failure progression. *Proc Natl Acad Sci USA.* 2006; 103(3):511-518. doi:10.1073/pnas.0510113103.
Wehrens XHT, Lehnart SE, Reiken SR, et al. Protection from cardiac arrhythmia through ryanodine receptor-stabilizing protein calstabin2. *Science.* 2004;304(5668):292-296. doi:10.1126/science.1094301.
Winn MP, Conlon PJ, Lynn KL, et al. A mutation in the TRPC6 cation channel causes familial focal segmental glomerulosclerosis. *Science.* 2005;308(5729):1801-1804. doi:10.1126/science.1106215.
Yang W, Shen Y, Chen Y, et al. Mesencephalic astrocyte-derived neurotrophic factor prevents neuron loss via inhibiting ischemia-induced apoptosis. *J Neurol Sci.* 2014;344(1-2):129-138. doi:10.1016/j.jns.2014.06.042.
Ye J, Rawson RB, Komuro R, et al. ER stress induces cleavage of membrane-bound ATF6 by the same proteases that process SREBPs. *Mol Cell.* 2000;6(6):1355-1364. doi:10.1016/s1097-2765(00)00133-7.
Yoshida H, Oku M, Suzuki M, Mori K. pXBP1(U) encoded in XBP1 pre-mRNA negatively regulates unfolded protein response activator pXBP1(S) in mammalian ER stress response. *J Cell Biol.* 2006;172(4):565-575. doi:10.1083/jcb.200508145.

\* cited by examiner

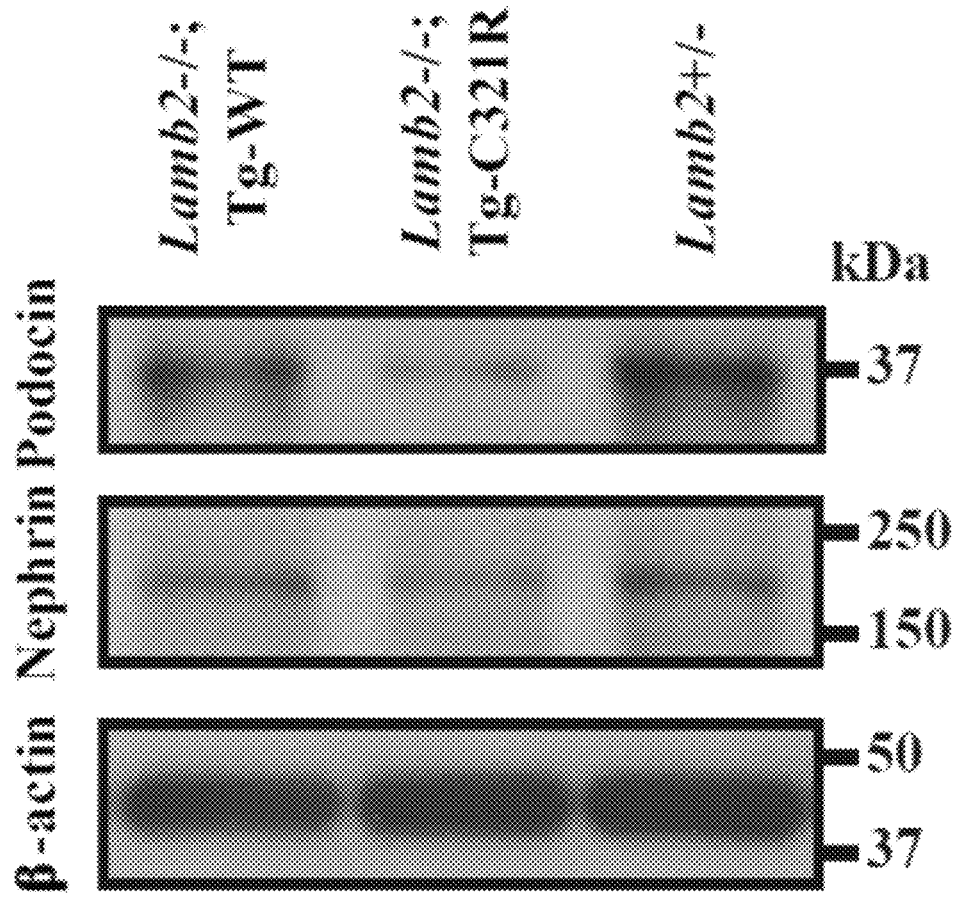

PRIOR ART

_Lamb2-/-; Tg-WT_

_Lamb2-/-; Tg-C321R_

SEQUENCE LISTING

<160> NUMBER OF SEQ ID NOS: 3

<210> SEQ ID NO 1
<211> LENGTH: 18
<212> TYPE: PRT
<213> ORGANISM: Homo sapiens

<400> SEQUENCE: 1

Met Gly Val Lys Val Leu Phe Ala Leu Ile Cys Ile Ala Val Ala Glu
1               5                   10                  15

Ala Lys

<210> SEQ ID NO 2

```
<211> LENGTH: 23
<212> TYPE: PRT
<213> ORGANISM: Homo sapiens

<400> SEQUENCE: 2

Met Trp Ala Thr Gln Gly Leu Ala Val Ala Leu Ala Leu Ser Val Leu
1               5                   10                  15

Pro Gly Ser Arg Ala Leu Arg
            20

<210> SEQ ID NO 3
<211> LENGTH: 7
<212> TYPE: PRT
<213> ORGANISM: Homo sapiens

<400> SEQUENCE: 3

Ala Ser Ala Arg Thr Asp Leu
1               5
```

COMPOSITIONS AND METHODS FOR TREATING AND PREVENTING ENDOPLASMIC RETICULUM (ER) STRESS-MEDIATED KIDNEY DISEASES

CROSS-REFERENCE TO RELATED APPLICATIONS

This application claims priority from U.S. Provisional Application Ser. No. 62/686,705 filed on Jun. 19, 2018 and U.S. Provisional Application Ser. No. 62/828,514 filed on Apr. 3, 2019, which are incorporated herein by reference in their entireties.

STATEMENT REGARDING FEDERALLY SPONSORED RESEARCH OR DEVELOPMENT

This invention was made with government support under grant number DK106451 and DK105056 awarded by National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to treating endoplasmic reticulum (ER)-stress mediated kidney diseases.

SUMMARY OF THE INVENTION

Among the various aspects of the present disclosure is the provision of methods and compositions to treat or prevent an endoplasmic reticulum (ER) stress-mediated kidney disease in a subject.

An aspect of the present disclosure provides for a method of stabilizing endoplasmic reticulum (ER) calcium channels or modulating ER stress in a subject in need thereof comprising: administering a therapeutically effective amount of an ER calcium channel stabilizing agent or an ER stress modulating agent to a subject, the subject having an endoplasmic reticulum (ER) stress-mediated kidney disease.

Another aspect of the present disclosure provides for a method of treating a subject in need thereof having or preventing an endoplasmic reticulum (ER) stress-mediated kidney disease comprising: administering a therapeutically effective amount of a pharmaceutical composition comprising an ER calcium channel stabilizing agent or an ER stress modulating agent to the subject.

In some embodiments, the therapeutically effective amount of the ER calcium channel stabilizing agent or the ER stress modulating agent is an amount sufficient to reduce apoptosis or injury in podocytes or tubular cells, compared to a control or the subject prior to administration of the ER calcium channel modulating agent or the ER stress modulating agent.

In some embodiments, the therapeutically effective amount of the ER calcium channel stabilizing agent or the ER stress modulating agent reduces RyR2 phosphorylation in podocytes or reduces calcium leaks in ER-stressed podocytes or tubular cells, when compared to a control or the subject prior to administration of the ER calcium channel modulating agent or the ER stress modulating agent.

In some embodiments, the therapeutically effective amount of the ER calcium channel stabilizing agent or the ER stress modulating agent: inhibits ER stress-mediated pro-apoptotic pathways, suppressing ER stress-induced apoptosis; inhibits ER stress-induced calcium efflux from the ER to cytosol in kidney cells; inhibits ER calcium depletion; inhibits albuminuria; decreases urinary calpain activity; corrects leaky RyR2 calcium channels; inhibits podocyte or tubular cell injury; inhibits podocyte or tubular cell apoptosis; or decreases proteinuria, compared to a control or the subject prior to administration of the ER calcium channel modulating agent or the ER stress modulating agent.

In some embodiments, the ER calcium channel stabilizing agent is a podocyte ER calcium channel stabilizing agent.

In some embodiments, the ER calcium channel stabilizing agent or the ER stress modulating agent is selected from mesencephalic astrocyte-derived neurotrophic factor (MANF) or compound K201.

In some embodiments, the ER calcium channel stabilizing agent or the ER stress modulating agent is MANF and the therapeutically effective amount of MANF is an amount sufficient to reduce RyR2 phosphorylation, block RyR2-Ser2808 phosphorylation-mediated ER calcium depletion, inhibit calpain 2 activation; decrease cleavage of spectrin and talin 1, suppress active cleaved caspase 12, reduce CHOP induction, or reduce early apoptotic rate in podocytes or tubular cells; or In some embodiments, the ER calcium channel stabilizing agent or the ER stress modulating agent is K201 and the therapeutically effective amount of K201 is an amount sufficient to suppress phosphorylation of RyR2, block RyR2-Ser2808 phosphorylation-mediated ER calcium depletion, decrease proteinuria, or block or inhibit podocyte injury in ER-stressed podocytes.

In some embodiments, the ER stress-mediated kidney disease is selected from the group consisting of: podocyte ER stress-mediated glomerular disease; diabetic nephropathy; primary nephrotic syndrome; renal fibrosis; a tubular ER stress-mediated kidney disease; and chronic kidney disease caused by an ER stress-mediated kidney disease.

In some embodiments, (i) the primary nephrotic syndrome is selected from the group consisting of: focal segmental glomerulosclerosis (FSGS), membranous nephropathy (MN), and minimal change disease (MCD); (ii) the podocyte ER stress-mediated glomerular disease is selected from the group consisting of: minimal change disease (MCD), focal segmental glomerulosclerosis (FSGS), membranous nephropathy (MN), hereditary nephrotic syndrome, sporadic nephrotic syndrome, diabetic nephropathy (DN), Alport syndrome, chronic kidney disease (CKD) caused by nephrotic syndrome (NS), and podocyte ER stress-mediated diabetic nephropathy (DN); or (iii) the tubular ER stress-mediated disease is selected from the group consisting of: autosomal dominant tubulointerstitial kidney disease (AD-KTD), ischemic acute kidney injury, or autosomal dominant polycystic kidney disease (ADPKD), and renal fibrosis.

In some embodiments, the tubular ER stress-mediated disease is selected from the group consisting of: renal fibrosis, autosomal dominant tubulointerstitial kidney disease (ADTKD), ischemic acute kidney injury, and autosomal dominant polycystic kidney disease (ADPKD).

DESCRIPTION OF THE DRAWINGS

Those of skill in the art will understand that the drawings, described below, are for illustrative purposes only. The drawings are not intended to limit the scope of the present teachings in any way.

FIG. 16A-FIG. 16D. Podocyte ER stress leads to downregulation of nephrin and podocin. Western blots (A,B) and analysis (C) for podocin and nephrin expression in (A) podocyte lysates and (B) glomerular lysates from Tg-WT, Tg-C321R and Lamb2$^{+/-}$ mice at P27. A Western blot for podocin and nephrin expression in glomerular lysates from mice at 6 weeks is also shown (D).

DETAILED DESCRIPTION OF THE INVENTION

Figure 1A:
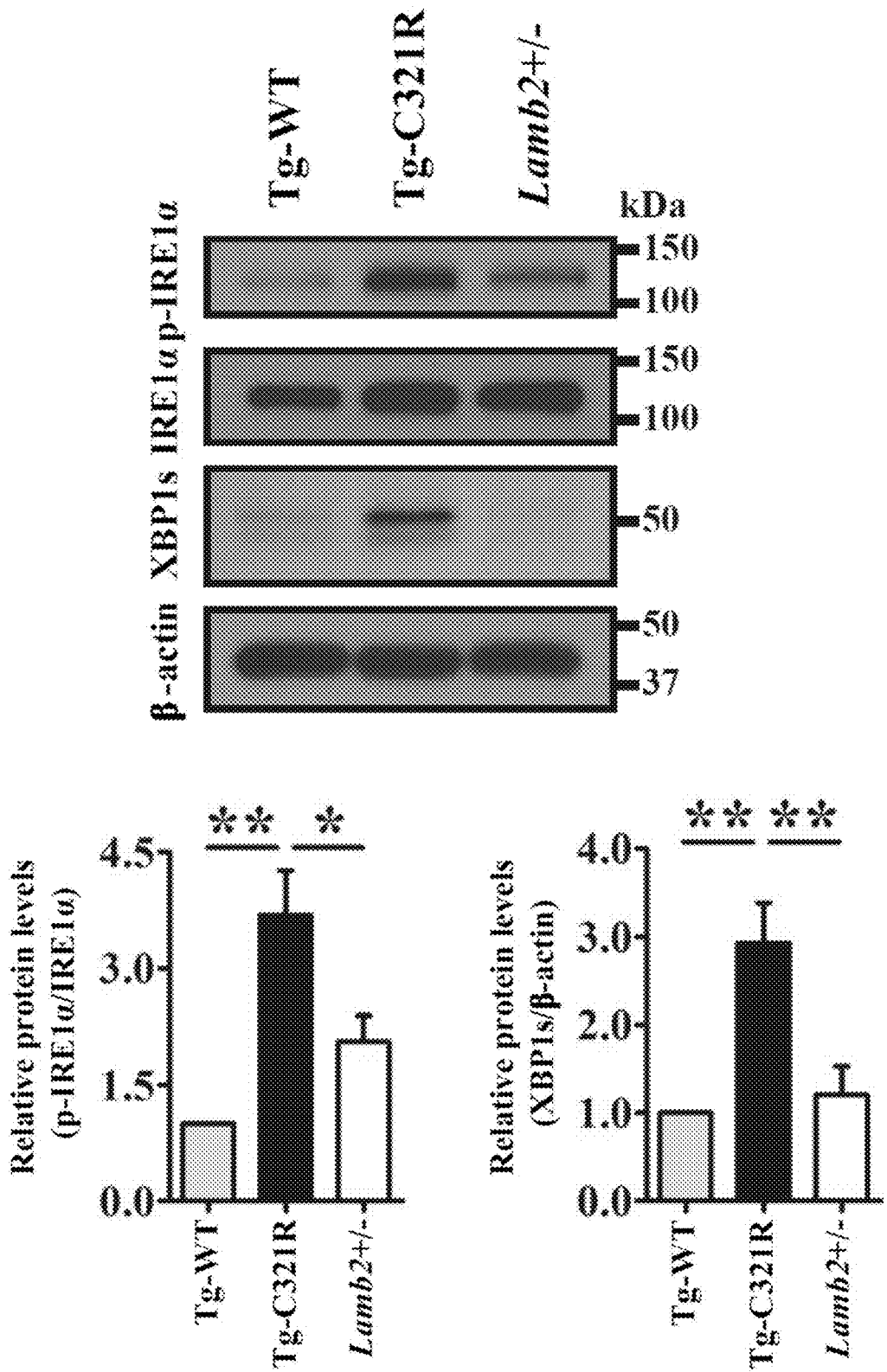
FIG. 1A-FIG. 1C. ER stress induced by C321R-LAMB2 disparately regulates the UPR branches in podocytes at the early stage of nephrotic syndrome (NS). Primary podocytes (P1 or P2) were isolated and cultured from Tg-WT, Tg-C321R, and Lamb2$^{+/-}$ mice at P27. (A) Representative immunoblots of phospho-IRE1α (p-IRE1α), IRE1α, and XBP1s expression in primary podocyte lysates of the indicated genotypes. Densitometry analysis of p-IRE1α normalized to IRE1α and sXBP1 normalized to β-actin was performed in the podocyte lysates. (B) Representative immunoblots of phospho-eIF2α (p-eIF2α), eIF2α, and ATF4 expression in primary podocytes of the indicated genotypes. Densitometry analysis of p-eIF2α normalized to eIF2α, and ATF4 normalized to β-actin was conducted in the podocyte lysates. (C) Representative immunoblot of p50ATF6 expression in primary podocytes of the indicated genotypes. Densitometry analysis of p50ATF6 normalized to β-actin was performed in the podocyte lysates. Quantification data in (A-C) represent the mean±SD of 5 independent experiments. *P<0.05; **P<0.01; NS: not significant by ANOVA.

The present disclosure is based, at least in part, on the discovery of podocyte ER calcium channel stabilizing agents (e.g., K201 and the protein mesencephalic astrocyte-derived neurotrophic factor (MANF)) are effective in the treatment of endoplasmic reticulum (ER) stress-mediated kidney diseases. As shown herein, the inventors discovered and developed a novel treatment for endoplasmic reticulum (ER) stress-mediated kidney diseases. As described herein, ER calcium channel stabilizing agents (e.g., MANF, K201) can inhibit ER stress-mediated pro-apoptotic pathways and ER stress-induced calcium efflux from the ER to the cytosol in kidney cells, thus suppressing ER stress-induced apoptosis. There are currently no therapeutics for ER stress-mediated kidney diseases.

Described herein is an approach to treat or prevent endoplasmic reticulum (ER) stress-mediated kidney diseases in a subject. The present disclosure provides for the use of an ER calcium channel stabilizing agent, such as mesencephalic astrocyte-derived neurotrophic factor (MANF) or K201, in the treatment of ER-stress mediated kidney diseases. The inventors have shown an ER calcium channel stabilizing agents can inhibit ER stress-mediated pro-apoptotic pathways and ER stress-induced calcium efflux from the ER to the cytosol in kidney cells, thus suppressing ER stress-induced apoptosis. For example, the inventors have engineered a mouse model of ER stress in kidney cells using podocyte-specific C321R-LAMB2 transgenic mice on the Lamb2 KO background and have shown K201 and recombinant MANF treatment suppresses apoptosis in TG-C321R podocytes.

Endoplasmic reticulum (ER) stress, the accumulation of misfolded and unfolded proteins in the ER, contributes to a number of kidney diseases. Since podocytes cannot replicate or regenerate, apoptosis of these cells results in kidney disease.

Here, it is shown that a novel ER stress modulator (e.g., MANF) blocks both the calcium dependent and independent apoptotic pathways. It has also been shown that an ER calcium channel stabilizing agent, JTV-519 (K201, ICP-Calstan 100), can inhibit ER stress-induced calcium efflux from the ER to the cytosol in podocytes, thus suppressing activation of the calpain 2-caspase 12 pathway, and mitigating stress-mediated apoptosis. K201 was shown to reverse hyper-phosphorylation of type 2 ryanodine receptor (RyR2) complex in cardiomyocytes, which prevents $Ca^{2+}$ from leaking out (calcium leaks). K201 is currently used to stabilize RyR2 in heart failure, cardiac arrhythmia, and hypertension in animal models. Here, K201 was identified through a screening assay. Studies confirmed decreased cytosolic calcium levels in podocytes and decreased proteinuria in vivo with K201 treatment.

Endoplasmic Reticulum (Er) Stress-Mediated Kidney Diseases

As described herein, endoplasmic reticulum (ER) stress modulating agents and ER calcium channel stabilizing agents can treat or prevent a wide spectrum of kidney diseases caused by ER dysfunction (i.e., ER stress-mediated kidney diseases). ER stress-mediated kidney disease can be a kidney disease characterized by ER stress-induced ER calcium release. There are currently no treatments for ER stress-mediated kidney diseases. An ER stress-mediated kidney disease can be caused by kidney cell ER stress. For example, an ER stress-mediated kidney disease can be a podocyte ER stress-mediated glomerular disease, such as minimal change disease (MCD), focal segmental glomerulosclerosis (FSGS), membranous nephropathy (MN), hereditary nephrotic syndromes, diabetic nephropathy (DN), podocyte ER stress-mediated diabetic nephropathy (DN), Alport syndrome, nephrotic syndrome (NS), or a tubular ER stress-mediated kidney disease, such as autosomal dominant tubulointerstitial kidney disease (ADTKD), ischemic acute kidney injury, autosomal dominant polycystic kidney disease (ADPKD), or renal fibrosis, as well as chronic kidney disease caused by all the above-mentioned etiologies.

As another example, the endoplasmic reticulum (ER) stress-mediated kidney disease can be primary nephrotic syndrome (NS) (e.g., focal segmental glomerulosclerosis, membranous nephropathy, or minimal change disease) or chronic renal fibrosis. Podocyte injury is the hallmark of nephrotic syndrome (NS), a leading cause of chronic kidney disease (CKD) affecting approximately 500 million people worldwide.

ER stress, or accumulation of misfolded and unfolded proteins in the ER lumen, contributes to a number of kidney diseases. It is presently believed that ER stress-induced apoptosis of renal cells is a major contributor to kidney disease. Canonically, podocytes cannot replicate or regenerate, so preventing apoptosis can be an effective route of therapy for a variety of kidney diseases.

Endoplasmic Reticulum (Er) Calcium Channel Stabilizing Agent

As described herein, an endoplasmic reticulum (ER) calcium channel stabilizing agent (e.g., mesencephalic astrocyte-derived neurotrophic factor (MANF), compound K201) can be used therapeutically for ER stress-mediated kidney diseases. For example, the ER calcium channel stabilizing agent can be a podocyte ER calcium channel stabilizing agent or a tubular ER calcium channel stabilizing agent.

As described herein, podocyte endoplasmic reticulum (ER) calcium release channel, type 2 ryanodine receptor (RyR2), undergoes phosphorylation during ER stress. The accelerated podocyte ER calcium efflux, due to leaky RyR2, activates cytosolic protease calpain 2, leading to apoptosis, cytoskeleton disruption, and podocyte injury. Chemical compounds K201 and a biotherapeutic protein, MANF, were discovered to fix leaky RyR2 and inhibit podocyte injury. The new class of drugs, podocyte ER calcium channel stabilizers, such as these RyR2 phosphorylation modulators, is shown to be a therapeutic strategy to treat a wide spectrum of kidney diseases caused by ER dysfunction.

The ER calcium channel stabilizing agent, mesencephalic astrocyte-derived neurotrophic factor (MANF), was discovered, here, to be useful as a therapeutic for ER stress-induced kidney disease. MANF blocks the ER calcium depletion-induced apoptotic pathway. MANF can be produced in any cell in the body undergoing ER stress to inhibit apoptosis; however, there is a high level of basal production in the pancreas beta cells. MANF, also known as ARMET or ARP, can be useful for the treatment of several categories of kidney diseases: podocyte—nephrotic syndrome, minimal change disease, focal segmental glomerulosclerosis, membranous nephropathy, Alport syndrome and diabetic nephropathy, or tubular—autosomal dominant tubulointerstitial kidney disease (ADKTD), ischemic acute kidney injury, autosomal dominant polycystic kidney disease (ADPKD), or renal fibrosis, as well as chronic kidney disease caused by all the above-mentioned etiologies. MANF, as described herein, can be the full protein or a functional fragment thereof, such as a peptide.

Other calcium release channel inhibitors can be calpain inhibitors, 1,4,5-triphosphate receptors (IP3Rs) inhibitors, or RyR2 modulating agents known in the art can be used as a podocyte ER calcium channel stabilizing agent (e.g., Calpeptin, diltiazem, K201/JTV519, dioxole derivative of K201, [4-methoxy-3-methyl phenol, FKBP12, 2-APB, SB 218078, Arguspongin B, Paxilline, S107); see e.g., Ye et al. Molecular Pharmacology January 2012, 81 (1) 53-62; Carragher, Curr Pharm Des. 2006; 12(5):615-38.

K201 (also known as JTV-519) can be of the formula:

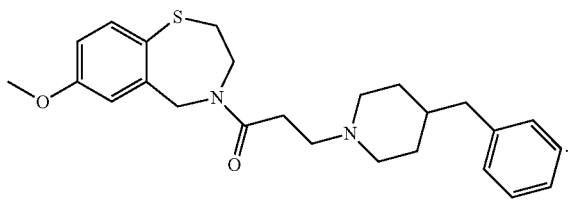

3-(4-Benzyl-1-piperidinyl)-1-(7-methoxy-2,3-dihydro-1,4-benzothiazepin-4(5H)-yl)-1-propanone Other calcium channel blockers can be dihydropyridine (DHP) calcium channel blockers such as Amlodipine (Norvasc); Aranidipine (Sapresta); Azelnidipine (Calblock); Barnidipine (HypoCa); Benidipine (Coniel); Cilnidipine (Atelec, Cinalong, Siscard) Not available in US; Clevidipine (Cleviprex); Efonidipine (Landel); Felodipine (Plendil); Isradipine (DynaCirc, Prescal); Lacidipine (Motens, Lacipil); Lercanidipine (Zanidip); Manidipine (Calslot, Madipine); Nicardipine (Cardene, Carden SR); Nifedipine (Procardia, Adalat); Nilvadipine (Nivadil); Nimodipine (Nimotop) This substance can pass the blood-brain barrier and is used to prevent cerebral vasospasm; Nisoldipine (Baymycard, Sular, Syscor); Nitrendipine (Cardif, Nitrepin, Baylotensin); or Pranidipine (Acalas).

Other calcium channel blockers can be phenylalkylamine calcium channel blockers, such as Fendiline, Gallopamil, or Verapamil (Calan, Isoptin); benzothiazepine calcium channel blockers, such as Diltiazem (Cardizem); non-selective calcium channel blockers, such as mibefradil, bepridil, flunarizine, fluspirilene, or fendiline; gabapentinoids, such as gabapentin or pregabalin; or Ziconotide.

Other calcium channel stabilizers can be SERCa agonists to stabilize the calcium inside the ER. SERCa, also known as sarco/ER $Ca^{2+}$ ATPase, is a pump for uphill transport of $Ca^{2+}$ from the cytoplasm into the ER lumen.

Endoplasmic Reticulum (Er) Stress Modulating Agent

As described herein, an endoplasmic reticulum (ER) stress modulating agent (e.g., mesencephalic astrocyte-derived neurotrophic factor (MANF)) can be used therapeutically for ER stress-mediated kidney diseases. For example, the ER stress modulating agent can be a podocyte ER stress modulating agent or a tubular ER stress modulating agent. As described herein, MANF has additional prosurvival effects than only being a podocyte ER calcium stabilizing agent. It can also inhibit other ER stress-mediated apoptotic pathways and exert its effects in renal tubular cells and podocytes.

The ER stress modulating agent, mesencephalic astrocyte-derived neurotrophic factor (MANF), was discovered, here, to be useful as a therapeutic for ER stress-induced kidney disease. MANF blocks 2 apoptotic pathways in the kidney—both $Ca^{2+}$ dependent and $Ca^{2+}$ independent pathways. MANF can be produced in any cell in the body undergoing ER stress to inhibit apoptosis; however, there is a high level of basal production in the pancreas beta cells. MANF, also known as ARMET or ARP, can be useful for the treatment of several categories of kidney diseases: podocyte—nephrotic syndrome, minimal change disease, focal segmental glomerulosclerosis, membranous nephropathy, Alport syndrome and diabetic nephropathy, or tubular—autosomal dominant tubulointerstitial kidney disease (AD-KTD), ischemic acute kidney injury, autosomal dominant polycystic kidney disease (ADPKD), or renal fibrosis, as well as chronic kidney disease caused by all the above-mentioned etiologies. As described herein, MANF has additional prosurvival effects than just being a podocyte ER calcium stabilizer. It can also inhibit other ER stress-mediated apoptotic pathways and exert its effects in renal tubular cells in addition to podocytes. MANF, as described herein, can be recombinant human MANF (e.g., from R&D Systems Minneapolis, Minn.), the full 18 kDa soluble protein, or a composition comprising or a functional fragment of MANF or a functional MANF peptide with a percent identity in a sufficient amount to retain MANF function.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intranasal, inhalation (e.g., in an aerosol), implanted, intramuscular, intraperitoneal, intravenous, subcutaneous, intranasal, epidural, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating an endoplasmic reticulum (ER) stress-mediated kidney disease in a subject in need of administration of a therapeutically effective amount of a pharmaceutical composition comprising an ER calcium channel stabilizing agent or an ER stress modulating agent, so as to inhibit ER stress-mediated pro-apoptotic pathways, inhibit ER stress-induced calcium efflux from the ER to the cytosol in kidney cells, or suppress ER stress-induced apoptosis.

Methods described herein are generally performed on a subject in need thereof. A subject in need of the therapeutic methods described herein can be a subject having, diagnosed with, suspected of having, or at risk for developing an endoplasmic reticulum (ER) stress-mediated kidney disease. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of a pharmaceutical composition comprising an ER calcium channel stabilizing agent or an ER stress modulating agent is, for example, that amount that would cause the desired therapeutic effect in a subject while minimizing undesired side effects. In various embodiments, an effective amount of a pharmaceutical composition comprising podocyte ER calcium channel stabilizing agent described herein can substantially inhibit an ER stress-mediated kidney disease, slow the progress of an ER stress-mediated kidney disease, or limit the development of an ER stress-mediated kidney disease.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a pharmaceutical composition comprising an ER calcium channel stabilizing agent or an ER stress modulating agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to inhibit ER stress-mediated pro-apoptotic pathways, inhibit ER stress-induced calcium efflux from the ER to the cytosol in kidney cells, or suppress ER stress-induced apoptosis.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a pharmaceutical composition comprising an ER calcium channel stabilizing agent or an ER stress modulating agent can occur as a single event or over a time course of treatment. For example, a pharmaceutical composition comprising an ER calcium channel stabilizing agent or an ER stress modulating agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for an endoplasmic reticulum (ER) stress-mediated kidney disease.

A pharmaceutical composition comprising an ER calcium channel stabilizing agent or an ER stress modulating agent can be administered simultaneously or sequentially with another agent, such as an antibiotic, an anti-inflammatory, or another agent. For example, a pharmaceutical composition comprising an ER calcium channel stabilizing agent or an ER stress modulating agent can be administered simultaneously with another agent, such as an antibiotic or an anti-inflammatory. Simultaneous administration can occur through administration of separate compositions, each containing one or more of a pharmaceutical composition comprising an ER calcium channel stabilizing agent or an ER stress modulating agent, an antibiotic, an anti-inflammatory, or another agent. Simultaneous administration can occur through administration of one composition containing two or more of a pharmaceutical composition comprising an ER calcium channel stabilizing agent or an ER stress modulating agent, an antibiotic, an anti-inflammatory, or another agent. A pharmaceutical composition comprising podocyte ER calcium channel stabilizing agent can be administered sequentially with an antibiotic, an anti-inflammatory, or another agent. For example, a pharmaceutical composition comprising an ER calcium channel stabilizing agent or an ER stress modulating agent can be administered before or after administration of an antibiotic, an anti-inflammatory, or another agent.

Controls or control samples, as described herein, can be a predetermined level, a biological sample (e.g., cells, serum, urine, blood) from a healthy control, a cell culture (e.g., podocyte cells or glomeruli), or a biological sample (e.g., cells, serum, urine, blood) from a subject in need thereof, for example, before treatment.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, renal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 m), nanospheres (e.g., less than 1 m), microspheres (e.g., 1-100 m), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see e.g., Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. (1988). Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Discovery of Novel Endoplasmic Reticulum Calcium Stabilizers to Rescue Er-Stressed Podocytes in Nephrotic Syndrome The following example describes the identification of an ER calcium release inhibitor, chemical compound K201 (4-[-3{1-(4-Benzyl) piperidinyl}propionyl]-7-methoxy-2,3, 4,5-tetrahydro-1,4-benzothiazepine)) and a novel biotherapeutic protein, MANF, which can fix leaky RyR2 and inhibit podocyte injury. The new class of drugs—podocyte ER calcium channel stabilizers—is an emerging therapeutic strategy to treat a wide spectrum of podocytopathies caused by ER dysfunction.

Here it is shown that an existing ER calcium stabilizer, K201 (JTV519), can be repurposed for use in the treatment of ER stress-mediated kidney diseases.

K201 has been shown to treat cardiac arrhythmia in mouse models. However, this chemical has not been used in the treatment of ER stress-mediated kidney diseases. Here, it was discovered that K201 can inhibit ER stress-induced calcium efflux from the ER to the cytosol in kidney cells and suppress ER stress-mediated activation of calpain 2-caspase 12 pathway, thus mitigating ER stress-induced apoptosis.

There are many kidney diseases caused by kidney cell ER stress-induced ER calcium release. These kidney diseases can comprise podocyte ER stress-mediated glomerular diseases, including minimal change disease, focal segmental glomerulosclerosis (FSGS), membranous nephropathy, nephrotic syndrome (NS), hereditary nephrotic syndromes, diabetic nephropathy, Alport disease/thin basement membrane disease, or tubular ER stress-mediated diseases, which can include autosomal dominant tubulointerstitial kidney disease (ADTKD), ischemic acute kidney injury, autosomal dominant polycystic kidney disease (ADPKD), or renal fibrosis, as well as chronic kidney disease caused by the above etiologies.

Emerging evidence has established primary nephrotic syndrome (NS), including focal segmental glomerulosclerosis (FSGS), as a primary podocytopathy. Despite the underlying importance of podocyte endoplasmic reticulum (ER) stress in the pathogenesis of NS, currently no treatment targets the podocyte ER. As described herein, in the monogenic podocyte ER stress-induced NS/FSGS mouse model, the podocyte type 2 ryanodine receptor/calcium release channel (RyR2) on the ER was phosphorylated, resulting in ER calcium leak and cytosolic calcium elevation. The altered intracellular calcium homeostasis led to activation of calcium-dependent cytosolic protease calpain 2 and cleavage of its important downstream substrates, including the apoptotic molecule procaspase 12 and podocyte cytoskeletal protein talin 1. It was discovered that a chemical compound, K201, can block RyR2-Ser2808 phosphorylation-mediated ER calcium depletion and podocyte injury in ER-stressed podocytes, as well as inhibit albuminuria in the NS model. It was also discovered that mesencephalic astrocyte-derived neurotrophic factor (MANF) can revert defective RyR2-induced ER calcium leak, a novel bioactivity for this ER stress responsive protein. Thus, it was shown that podocyte RyR2 remodeling contributes to ER stress-induced podocyte injury. As such, K201 and MANF can be useful for the treatment of podocyte ER stress-induced NS/FSGS.

INTRODUCTION

Primary nephrotic syndrome (NS), including focal segmental glomerulosclerosis (FSGS), is one of the leading causes of chronic kidney disease, which affects approximately 500 million people worldwide and is increasing in incidence. Seminal advances in past decades have identified primary NS/FSGS as a primary podocytopathy with major discoveries of podocyte-specific gene mutations in human NS patients, including NPHS1, NPHS2, WT-1, LAMB2, CD2AP, TRPC6, ACTN4, and INF2. Although accumulating studies have highlighted the importance of intracellular calcium dysregulation in the pathogenesis of podocytopathy, most studies have focused on increased calcium influx across the podocyte plasma membrane, resulting from over-expression of the G-protein-coupled angiotensin II type 1 receptor or hyperactivity/overexpression of transient receptor potential cation channel subfamily C member 6 (TRPC6). The role of podocyte endoplasmic reticulum (ER) calcium efflux under ER stress in the pathogenesis of proteinuria remained to be elucidated.

The ER plays important roles in folding, post-translational modification, and trafficking of newly synthesized secretory and membrane proteins. Protein folding is aided by ER-resident molecular chaperones and enzymes, such as immunoglobulin binding protein (BiP), calnexin, calreticulin, and protein disulfide isomerase. Disturbance to ER homeostasis leads to accumulation of unfolded or misfolded proteins in the ER lumen, which causes ER stress and activates unfolded protein response (UPR) pathways. The UPR is regulated by three ER transmembrane proteins: inositol-requiring enzyme 1 (IRE1), protein kinase-like ER kinase (PERK), and activating transcription factor 6 (ATF6), which act as proximal sensors of ER stress. ER stress activates these sensors by inducing phosphorylation and homodimerization of IRE1α and PERK/eIF2α (eukaryotic initiation factor 2α), as well as relocalization of ATF6 to the Golgi where it is cleaved by S1P/S2P proteases from 90 kDa to the active 50 kDa ATF6, leading to activation of their respective downstream transcription factors, spliced XBP1 (XBP1s), activating transcription factor 4 (ATF4) and p50ATF6. The intense or prolonged UPR can result in cell apoptosis and death. Caspase 12, C/EBP homologous protein (CHOP), and Jun N-terminal kinase (JNK) are ER stress-specific apoptotic pathways.

Mounting evidence has demonstrated that podocyte ER stress plays a vital role in the pathogenesis of idiopathic NS. In cell culture studies, certain NS-causing nephrin or podocin missense mutants are trapped inside the ER and activate ER stress. In mouse models, podocyte ER stress induced by pathogenic mutations Lamb2 C321R, Actn4 K256E, or Col4a3 G1332E leads to NS and podocytopathy. In human studies, multiple collagen IV mutations, the most frequent mutations underpinning adult primary FSGS/steroid-resistant NS, activate the UPR in podocytes. Moreover, in FSGS associated with APOL1 renal risk alleles, ER stress secondary to altered endolysosomal trafficking has been shown to induce cell injury. Finally, CHOP is upregulated in the podocytes of kidney biopsies from FSGS, membranous nephropathy (MN) and minimal change disease (MCD) patients compared with controls. Despite the importance of podocyte ER stress in NS, there is no treatment that targets the podocyte ER dysfunction.

Aberrant ER calcium homeostasis triggered by ER stress may play a critical role in the regulation of apoptotic cell death. Calcium in the ER lumen is maintained at concentrations 1000-fold to 10,000-fold greater than in the cytoplasm by the sarco/ER $Ca^{2+}$ ATPase (SERCA), a pump for uphill transport of $Ca^{2+}$ from the cytoplasm into the ER lumen. The majority of calcium efflux from the ER is mediated by ryanodine receptors (RyRs) and inositol 1,4,5-triphosphate receptors (IP3Rs). Three isoforms of RyR and IP3R have been identified. In contrast to IP3Rs that are expressed in all cell types, RyRs are mainly expressed in muscles and neurons. RyR1 predominates in skeletal muscle, RyR2 in heart and brain, and RyR3 is expressed at low levels in various tissues. Whether these ER calcium channels undergo remodeling in ER-stressed podocytes and their functional impact in podocyte integrity and injury is believed to not have been previously studied.

Figure 19:
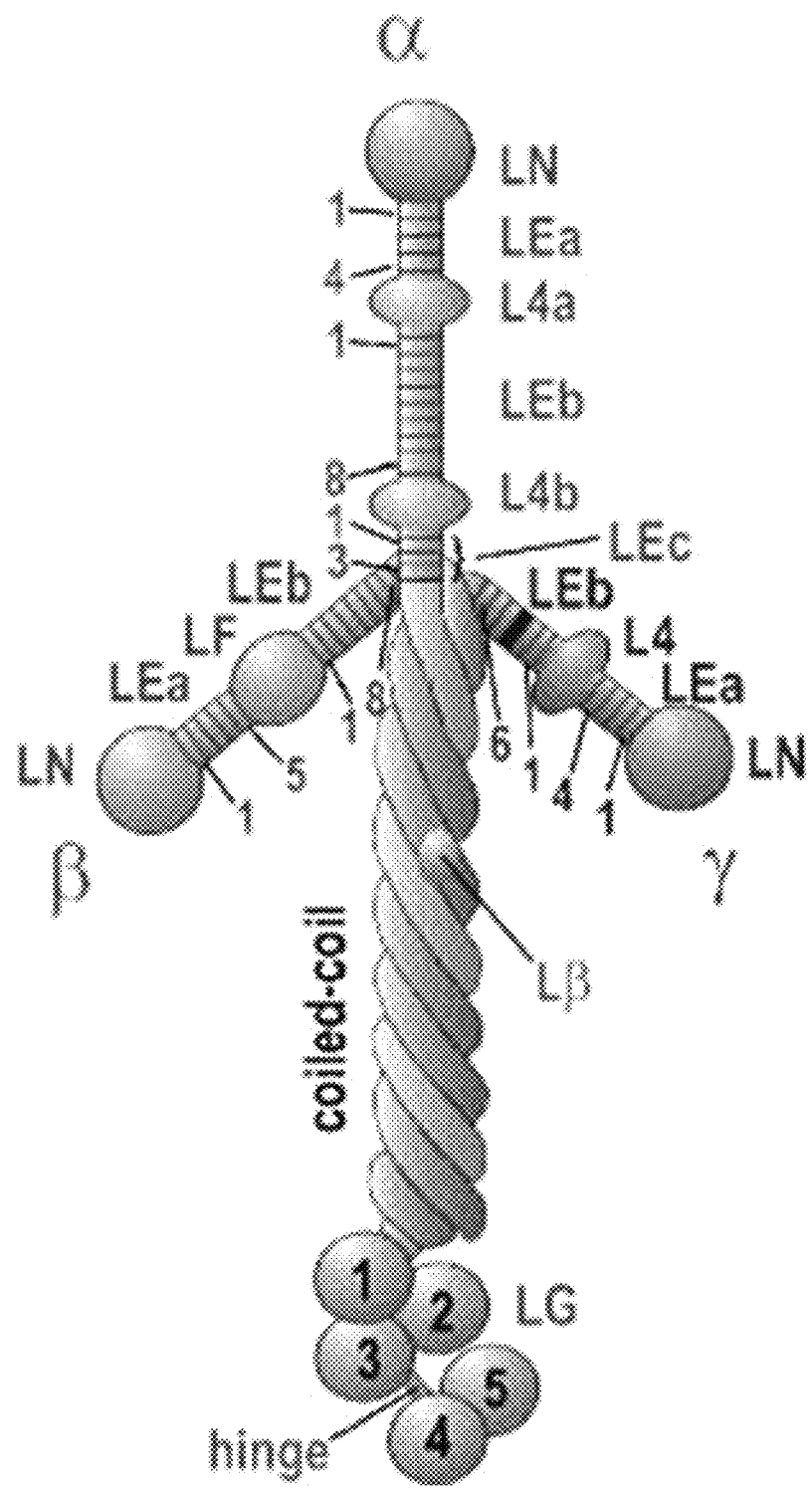
FIG. 19. Schematic of the laminin αβγ heterotrimer protein.

To investigate the molecular pathogenesis and treatment of podocyte ER stress-induced NS, a mouse model of NS caused by LAMB2 C321R, a mutation identified in human patients, was established. Laminin β2 encoded by LAMB2 is a component of the laminin-521 (α5β2γ1) trimer, an important constituent of the mature glomerular basement membrane (GBM) (see e.g., FIG. 19). Laminin trimerization occurs in the ER, and the trimers are secreted by both podocytes and glomerular endothelial cells to the GBM. It was shown that transgenic (Tg) expression of C321R-LAMB2 in podocytes via the podocyte-specific mouse nephrin promoter on the Lamb2$^{-/-}$ background (Lamb2$^{-/-}$; Tg-C321R, hereafter referred to as Tg-C321R mice) recapitulates features of the corresponding human NS patients (see e.g., FIG. 20). At 3-4 weeks of age, when Tg-C321R mutants exhibit trace proteinuria without notable renal histological alterations, podocyte ER stress induced by the C321R mutant protein is evident (see e.g., FIG. 14, FIG. 15, FIG. 18, FIG. 21A). At 6-8 weeks of age, the mutant mice develop diffuse foot process (FP) effacement, mild GBM thickening, overt proteinuria, and FSGS (see e.g., FIG. 21B). It was also shown that in expression-matched Lamb2$^{-/-}$; Tg-WT (hereafter referred to as Tg-WT) mice (see e.g., FIG. 20), expression of wild-type (WT) β2 cDNA in podocytes is sufficient to restore the integrity of the glomerular filtration barrier and prevent proteinuria in Lamb2$^{-/-}$ mice. By utilizing this monogenic NS mouse model, the aim of this study was to determine whether ER calcium homeostasis is dysregulated in podocytes undergoing ER stress and to discover novel therapeutic agents targeting the ER to inhibit podocyte injury and proteinuria in NS/FSGS.

Results

Tripartite UPR is Differentially Regulated in Mutant Podocytes in the Incipient Stage of NS To delineate the molecular mechanism underpinning the regulation of UPR in ER stressed-podocytes at the early stage of proteinuria, passage 0-1 (P0-P1) primary podocytes from Tg-WT, Tg-C321R and Lamb2$^{+/-}$ (WT) mice at postnatal day 27 (P27) were isolated and cultured. Western blot (WB) analysis of primary podocytes showed that protein levels of p-IRE1α and XBP1s, as well as p-eIF2α and ATF4, were increased in Tg-C321R podocytes compared with the Tg-WT and WT podocytes (see e.g., FIG. 1A and FIG. 1B). In contrast, the active form of ATF6 (p50 ATF6) was unchanged across genotypes, excluding its involvement in this disease model (see e.g., FIG. 1C). Together, these data demonstrate that the IRE1α and PERK pathways, but not the ATF6 pathway, are selectively activated in response to podocyte ER stress induced by the C321R mutation in the pathogenesis of NS.

Figure 2A:
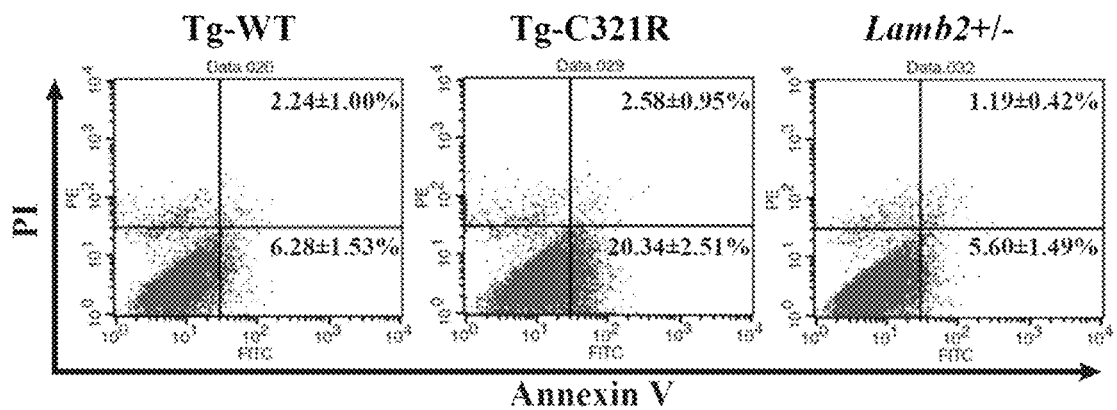
FIG. 2A-FIG. 2D. Caspase 12 contributes to podocyte ER stress-mediated apoptosis at the early stage of NS. (A) Primary podocytes from Tg-WT, Tg-C321R and Lamb2$^{+/-}$ mice at P27 were stained with Annexin V-FITC and PI, and analyzed by flow cytometry. The values in the lower right quadrant of the representative histograms indicate the percentage of podocytes undergoing early apoptosis (Annexin V$^+$/PI$^-$ cells). The percentage of early apoptotic podocytes was expressed as mean±SD from 3 independent experiments. ***P<0.001 by ANOVA. (B-C) Primary podocyte lysates from Tg-WT, Tg-C321R and Lamb2$^{+/-}$ mice at P27 were analyzed by Western Blot with the indicated antibodies. Arrows indicate cleaved forms of the proteins of interest. Quantification of (B) cleaved caspase 12 as well as (C) cleaved caspase 3 was normalized to β-actin. (D) Glomeruli were isolated from age-matched Tg-WT, Tg-C321R and Lamb2$^{+/-}$ mice at P27. Western Blot analysis of cleaved caspase 12, cleaved caspase 3, and β-actin in isolated glomeruli from the indicated genotypes. Quantification of cleaved caspase 12 and cleaved caspase 3 was normalized to β-actin in isolated glomerular lysates. Arrows indicate cleaved (active) caspases 12 and 3. Mean±SD of 5 independent experiments; *P<0.05; **P<0.01 by ANOVA.
Figure 2A:
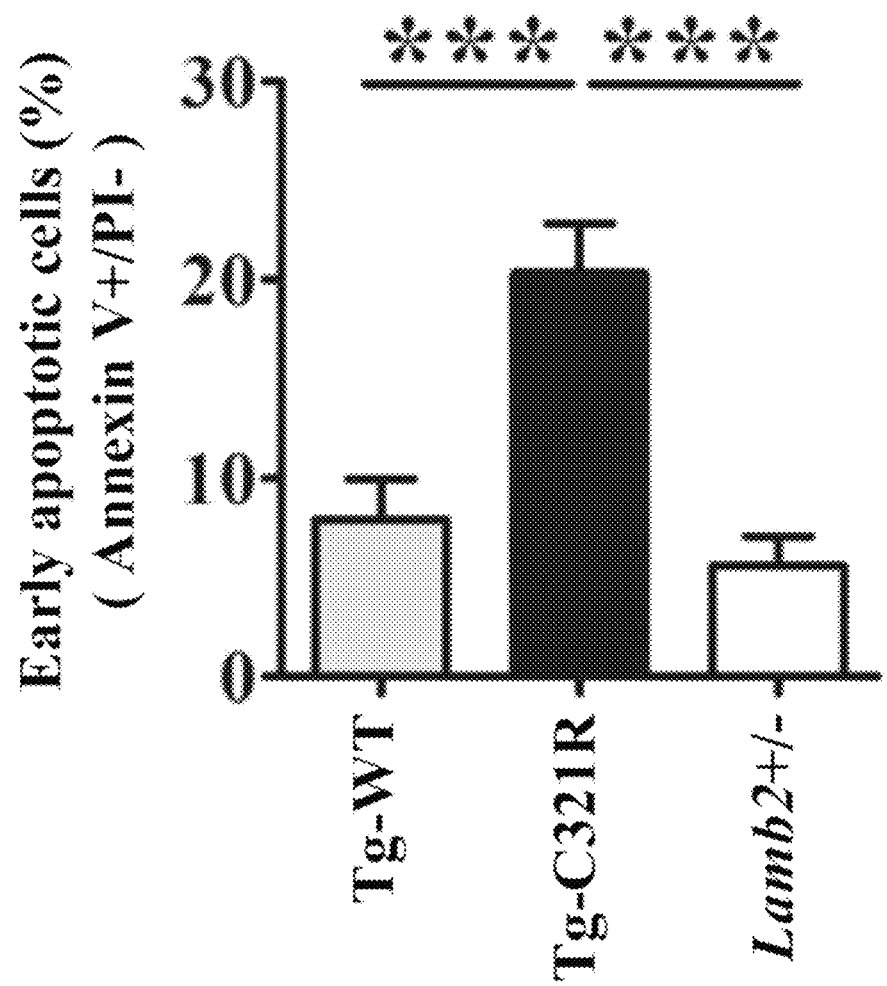
Figure 2B:
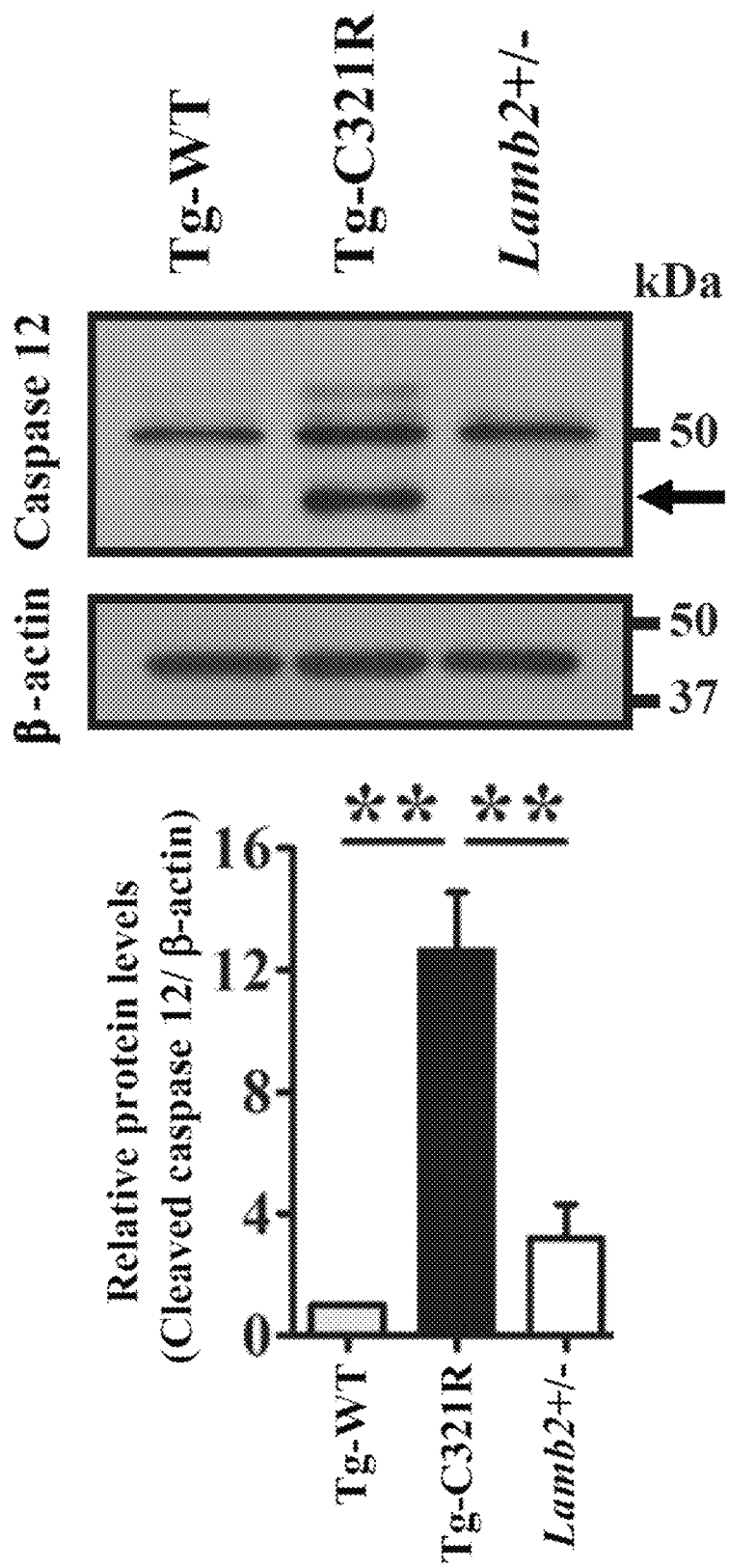
Figure 2C:
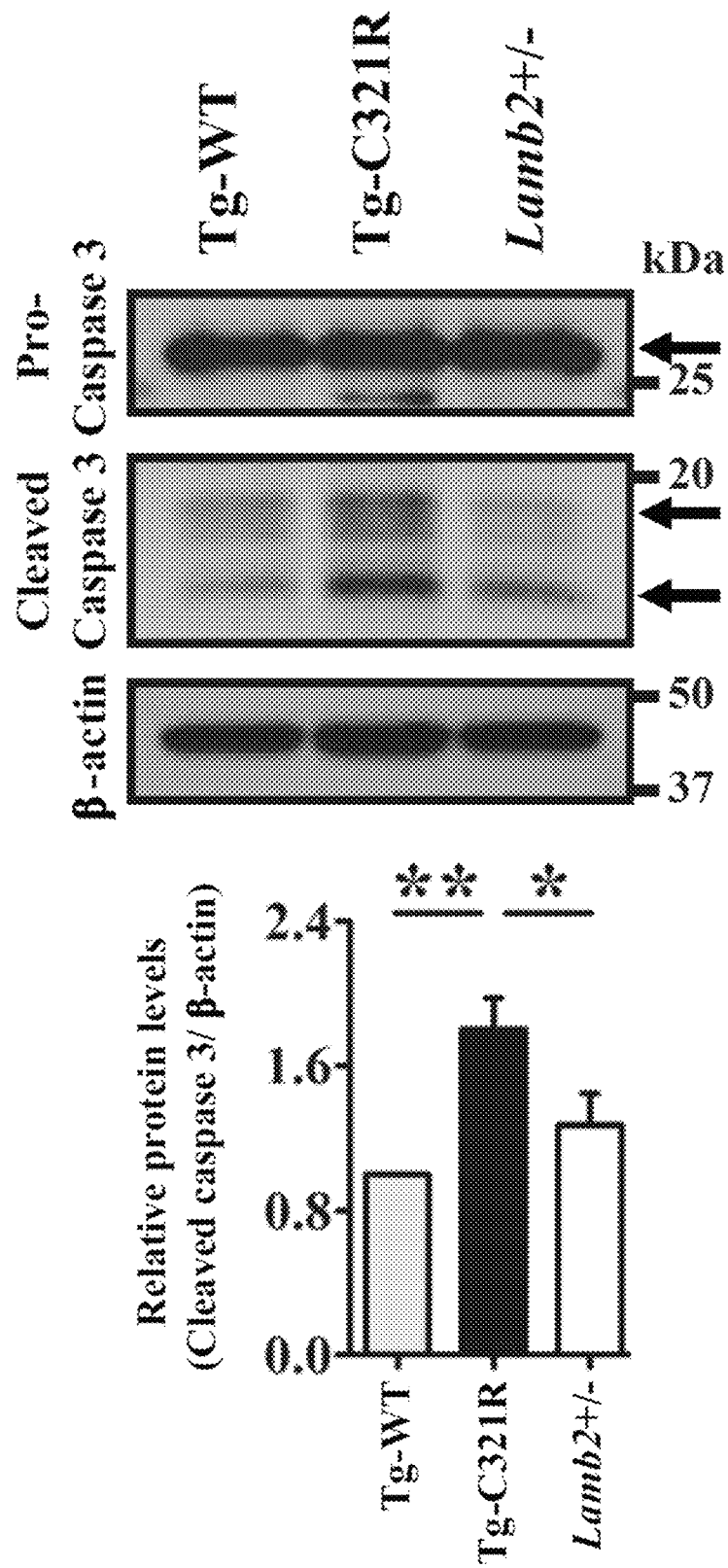
Figure 2D:
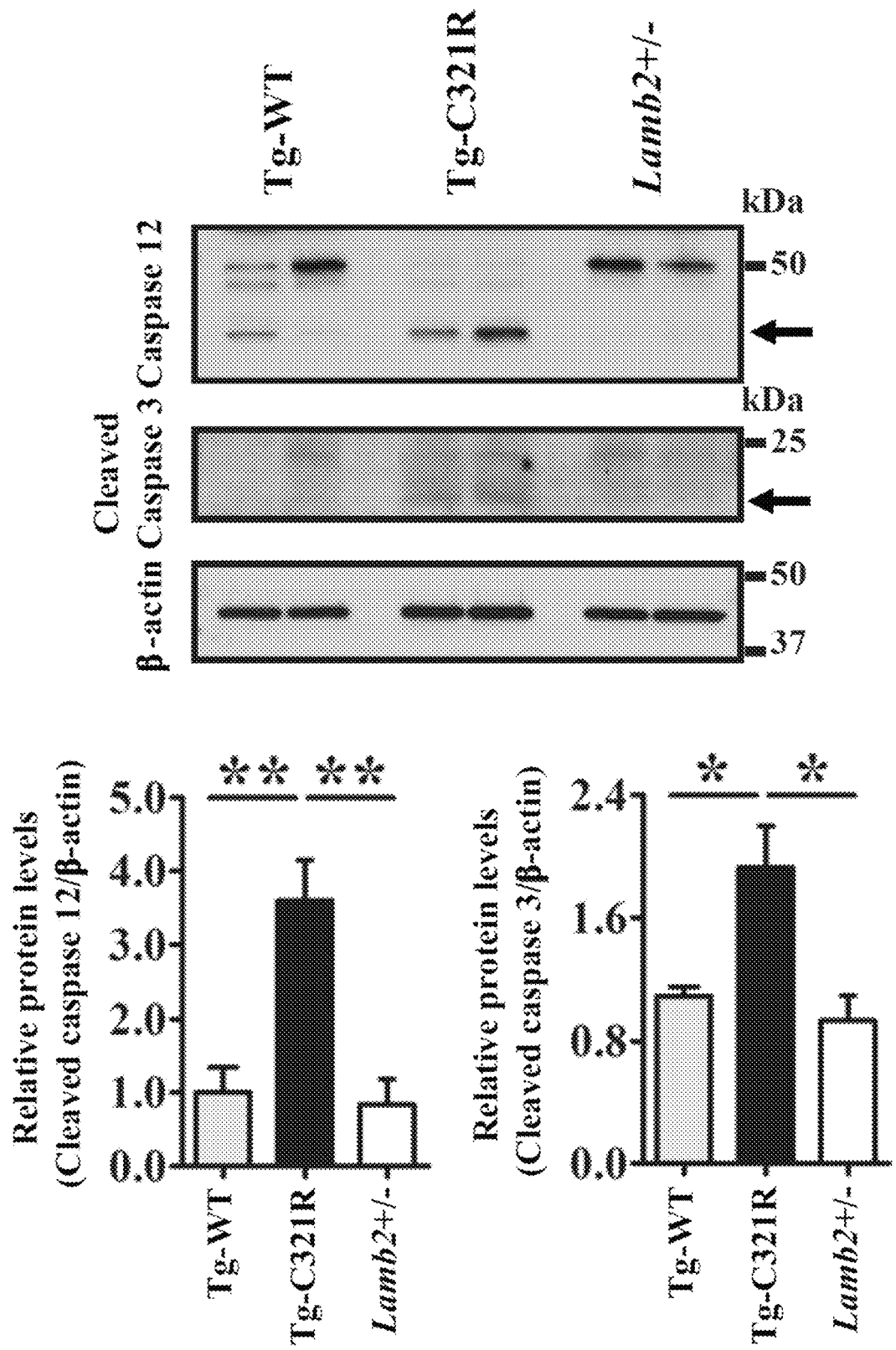

Podocyte ER Stress Results in Caspase 12 Activation and Apoptosis at the Early Stage of the Disease Chronic and unrelieved ER stress may result in apoptosis. Given that mild desmin expression, an indicator of podocyte injury, was previously observed in the mutant podocytes at the early stage of proteinuria, primary podocyte apoptosis at P27 was measured directly by utilizing flow cytometry. Annexin V$^+$/Propidium iodide (PI)$^-$ cells are regarded as early apoptotic cells, whereas double positive cells are regarded as late apoptotic or necroptotic cells. Indeed, the rate of early apoptosis was significantly increased in Tg-C321R podocytes (20.34±2.51%) as compared with Tg-WT (6.28±1.53%) and WT podocytes (5.60±1.49%) (P<0.001) (see e.g., FIG. 2A). Next, the ER stress-specific pro-apoptotic pathways activated in the mutant podocytes at the early stage of disease were identified. Besides CHOP activation in both Tg-C321R podocytes and glomeruli (see e.g., FIG. 18), a striking cleavage of ER-resident procaspase 12, reflecting its activation, was observed in Tg-C321R podocytes compared with control podocytes at P27 (see e.g., FIG. 2B). Consequently, activation of the executioner caspase 3 (cleaved form of procaspase 3) was increased in the mutant podocytes versus control podocytes (see e.g., FIG. 2C). To make sure that the observed activation of caspases 12 and 3 in mutant podocytes was not due to in vitro culturing, glomeruli from the indicated genotypes were also isolated at P27. The same results were confirmed in the isolated glomeruli from the different groups (see e.g., FIG. 2D). On the other hand, the JNK pathway (p46/p54 kDa) was not involved in the podocyte ER stress-induced apoptosis at the early stage of proteinuria (see e.g., FIG. 9A and FIG. 9B). Taken together, these results demonstrate that caspase 12 contributes to podocyte ER stress-mediated apoptosis at the early stage of the disease pathogenesis.

Cytosolic Calcium-Dependent Calpain 2 is Activated in Mutant Podocytes

Figure 3A:
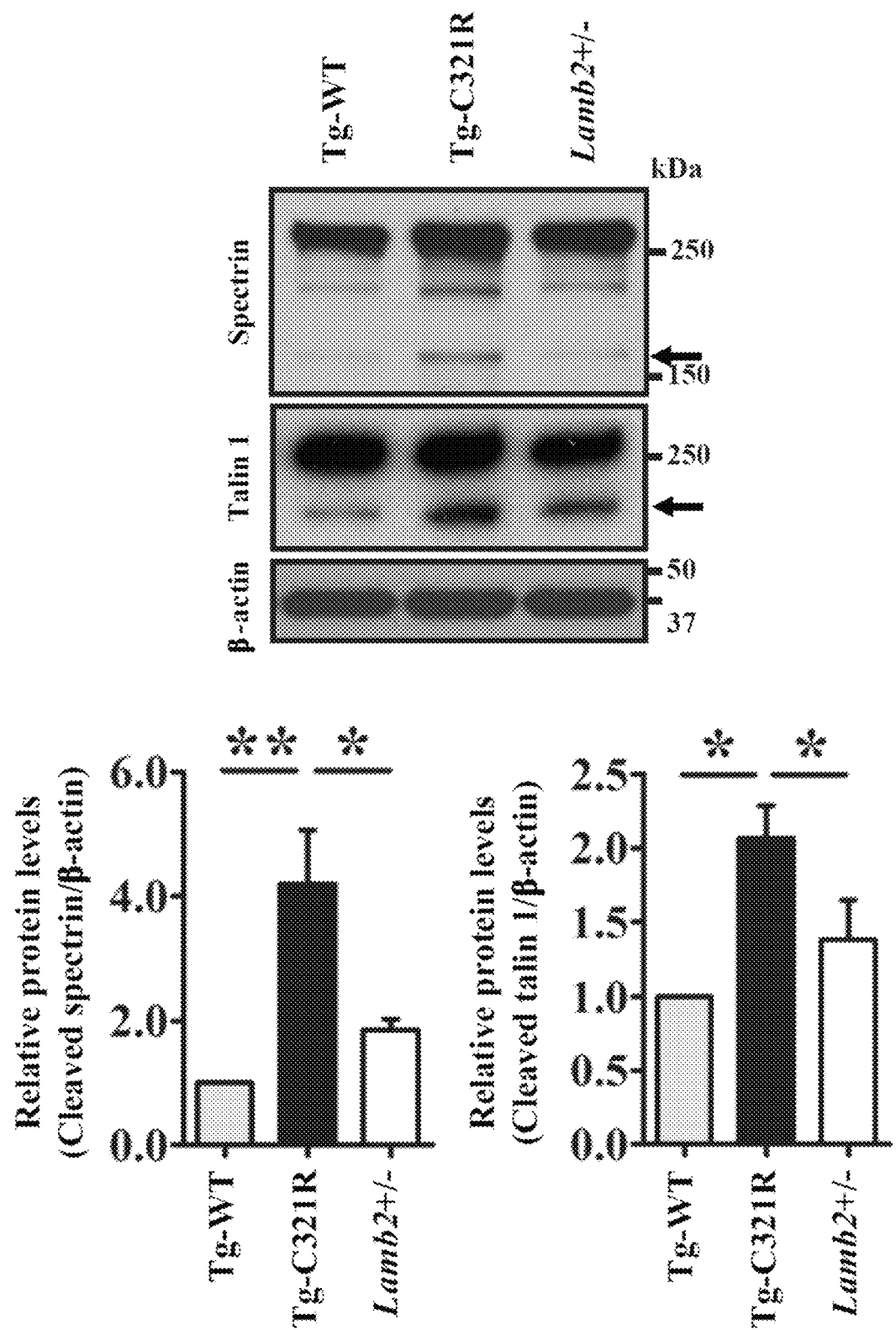
FIG. 3A-FIG. 3D. Podocyte ER stress induces cytosolic calcium elevation and activation of calcium-dependent calpain 2 activity. Western blot analysis of spectrin and talin 1 in (A) primary podocyte lysates and (B) glomerular lysates from Tg-WT, Tg-C321R and Lamb2$^{+/-}$ mice at P27 were analyzed by Western Blot for cleavage of spectrin and talin 1. Arrow indicates cleaved spectrin or talin 1. Quantification of cleaved spectrin and talin 1 was normalized to β-actin in primary podocyte lysates. Mean±SD of 5 independent experiments. *P<0.05; **P<0.01 by ANOVA. Quantification of cleaved spectrin and talin 1 was normalized to β-actin in glomerular lysates. Mean±SD of 5 independent experiments. *P<0.05; P<0.01 by ANOVA. (C) Urinary calpain activity/Cr assay from the indicated groups at P25-P27. The urinary calpain activity/Cr in Lamb2$^{+/-}$ mice was set as 1. n=5 per group, P<0.01 by ANOVA. (D) Fluorescence intensity measured by flow cytometry for Tg-C321R and control podocytes stained with cytosolic calcium indicator Fluo-4 AM. The relative fluorescence intensity was expressed as Mean±SD from 3 independent experiments. ***P<0.001 by ANOVA.
Figure 3B:
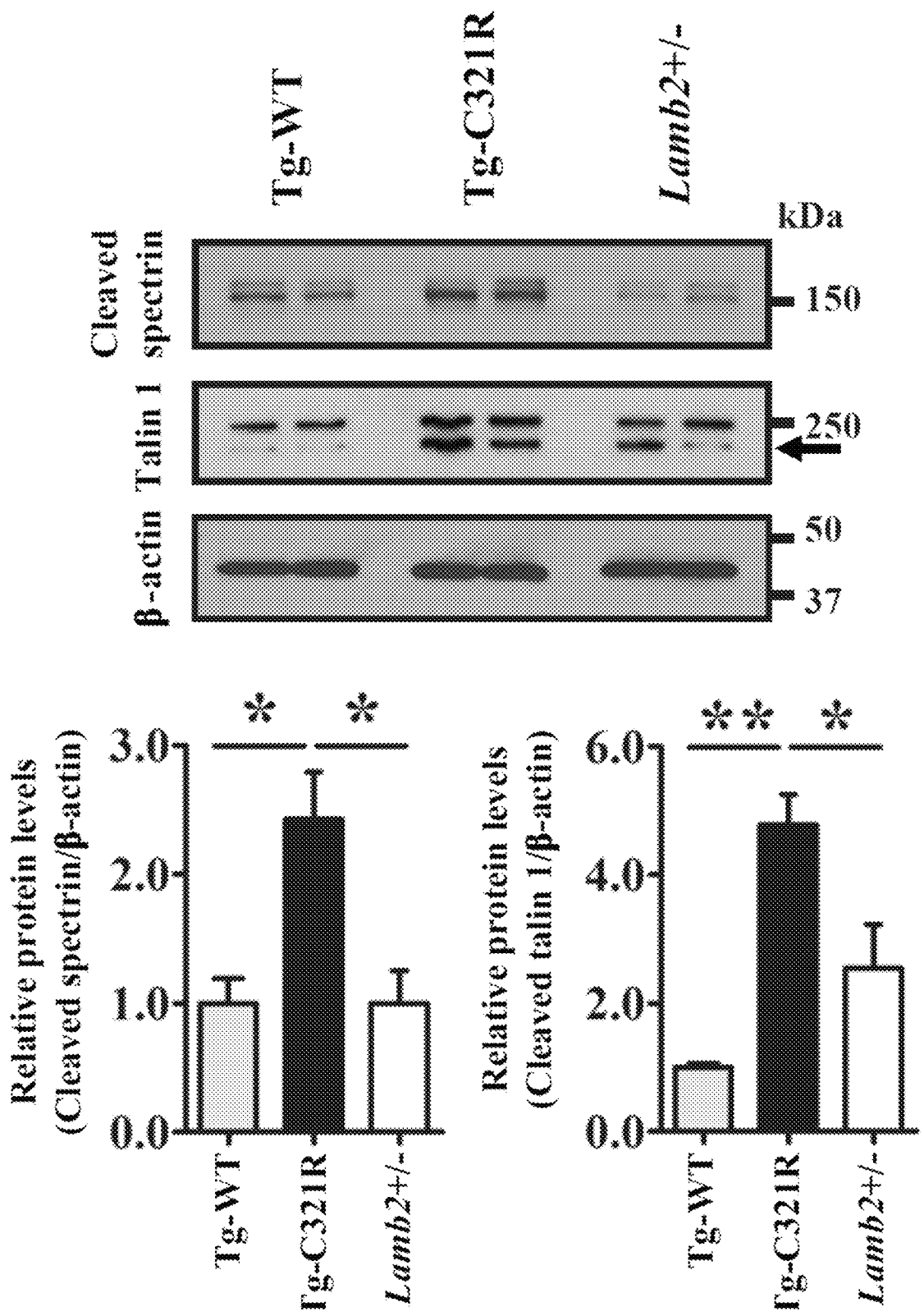
Figure 3C:
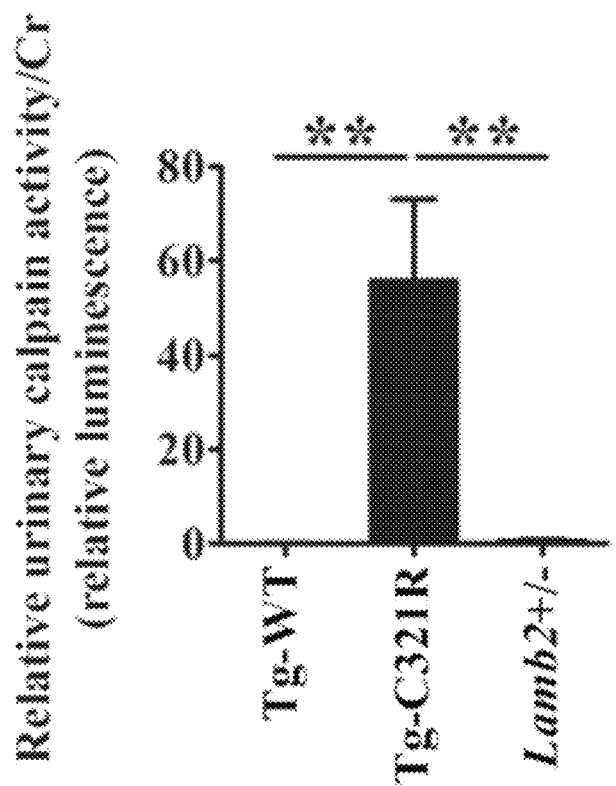
Figure 3D:
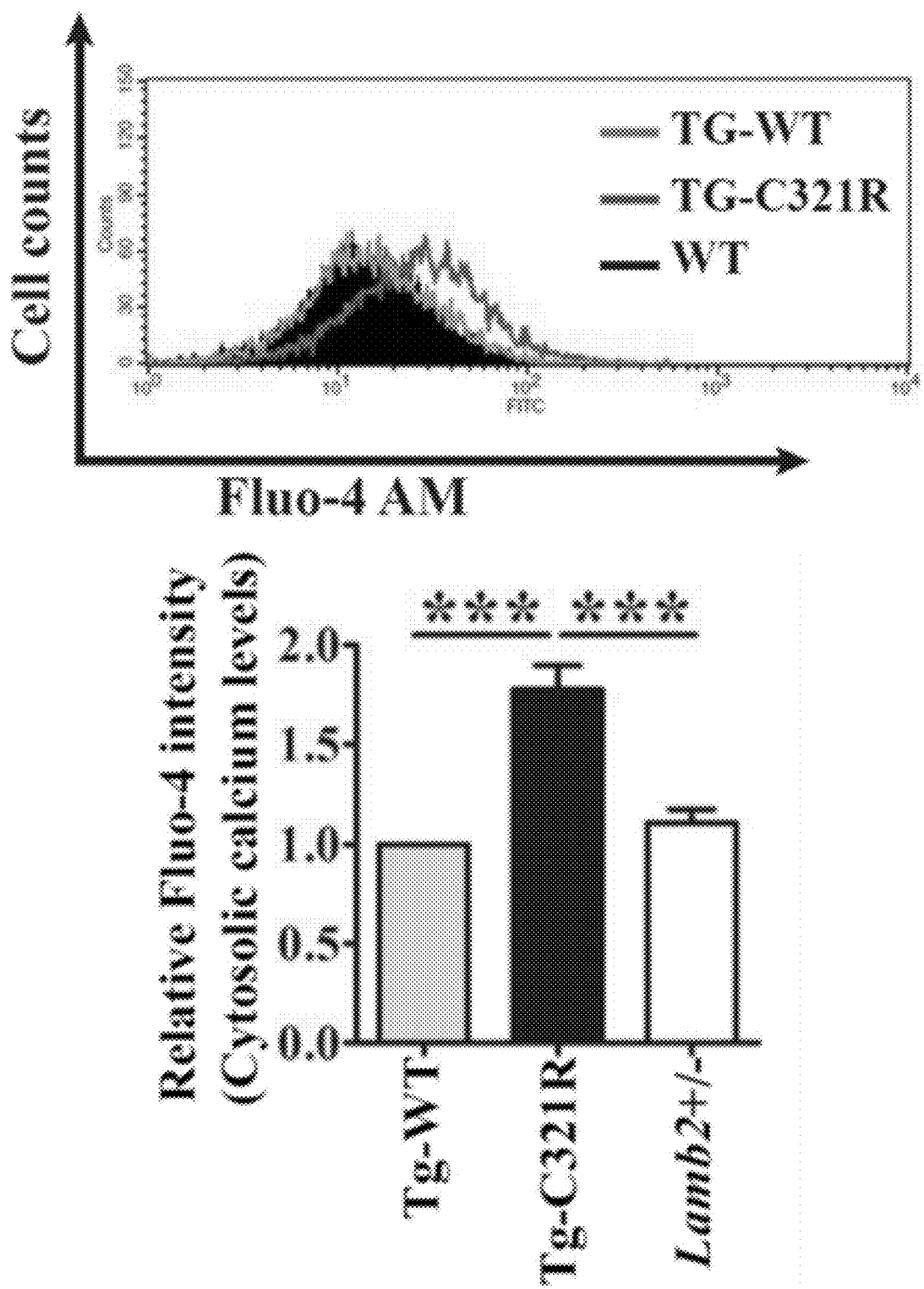

Activation of ER-resident procaspase 12 in the mutant podocytes (see e.g., FIG. 2B and FIG. 2D) prompted further investigation of its upstream calpain 2 activity at the early stage of proteinuria. Calpain 2 is a cytosol cysteine protease, which is known to be activated by cytosolic calcium elevation and cleaves caspase 12 after activation. Additionally, calpain 2 has been shown to mediate diverse biological functions, including cleavage of podocyte cytoskeleton-associated anchoring protein talin 1, leading to FP effacement. Western Blot revealed that Tg-C321R podocytes exhibited increased cleavage of alpha II spectrin, a well characterized substrate for calpain 2 and a component of the nephrin multiprotein complex, compared with control podocytes at P27, indicative of the enhanced activity of calpain 2 and cytosolic calcium overload in Tg-C321R podocytes (see e.g., FIG. 3A). Meanwhile, increased cleavage of talin 1 was also noted in Tg-C321R podocytes compared with control podocytes at P27 (see e.g., FIG. 3A). Increased cleavage of spectrin and talin 1 in Tg-C321R glomeruli compared with control glomeruli at P27 was also verified (see e.g., FIG. 3B). Protein levels of calpain 2 did not differ much among different genotypes in both primary podocytes and isolated glomeruli. As calpain 2 is secreted from podocytes to the urine, urinary calpain activity that was determined by luciferase assay and normalized to urine creatinine (Cr) excretion (urinary calpain activity/Cr), was analyzed in Tg-WT, Tg-C321R and Lamb2-, mice at P25-P27 (see e.g., FIG. 3C). The urinary calpain activity/Cr in Tg-C321R mutants was significantly higher than that in control mice. Next, it was directly demonstrated that cytosolic calcium was increased in the mutant podocytes. Podocytes were stained with fluorescent cytosolic calcium indicator Fluo-4 AM (acetoxymethyl) and the fluorescence intensity was measured by flow cytometry (see e.g., FIG. 3D). Cytoplasmic calcium levels were higher in Tg-C321R podocytes relative to control podocytes. Collectively, these results indicate that the calpain 2-caspase 12 pathway was activated by cytosolic calcium elevation in the mutant podocytes, resulting in the subsequent podocyte injury.

Figure 4A:
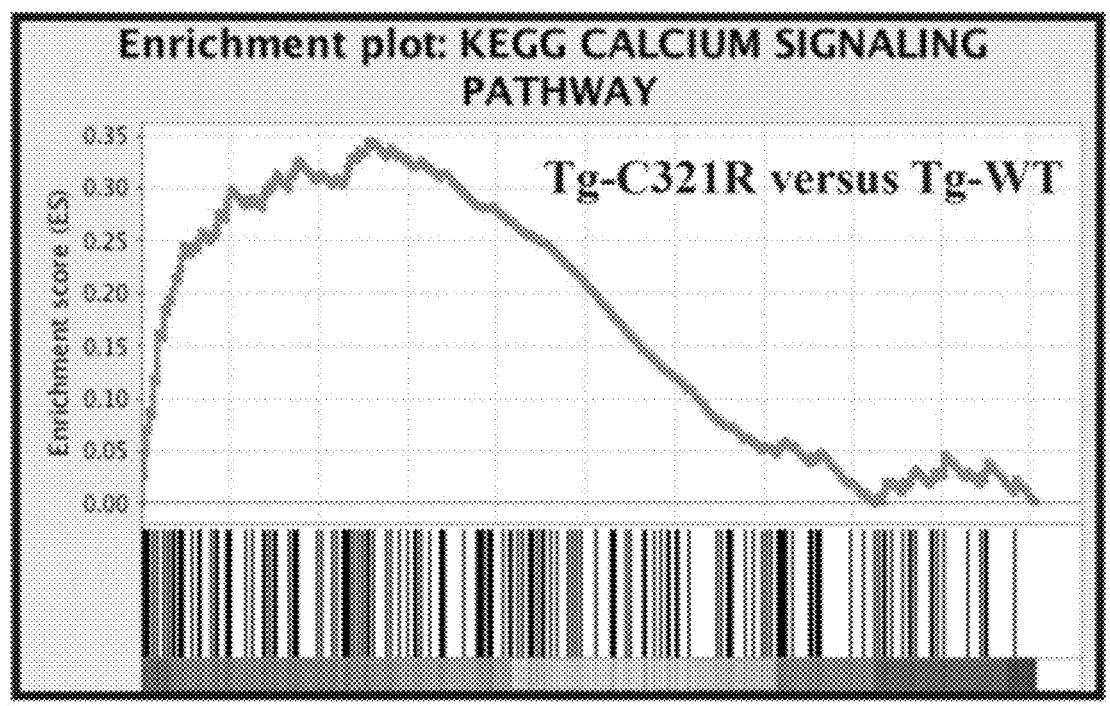
FIG. 4A-FIG. 4D. Podocyte ER stress induces ER calcium release through RyR2 phosphorylation. (A) Gene set enrichment analysis of calcium signaling gene transcript abundance in primary podocytes (P0) isolated from Tg-C321R and Tg-WT mice at P27. P<0.001, enrichment score 0.34 and normalized enrichment score 1.41. (B) Western blot analysis of p-RyR2 (S2808) and RyR expression in primary podocyte lysates from the indicated genotypes. Quantification of p-RyR2 (S2808) was normalized to RyR in the podocyte lysates. Mean±SD of 3 independent experiments. *P<0.05 by ANOVA. (C) Schematic of SERCaMP and control GLuc-STOP fusion proteins. The first 18 amino acids of GLuc (MGVKVLFALICIAVAEAK (SEQ ID NO: 1), signal peptide) were replaced with the signal peptide of MANF (amino acid 1-23, MWATQGLAVALALSVLPGSRALR (SEQ ID NO: 2)) to target the proteins to the secretory pathway. The C-terminal sequence of MANF, ASARTDL (SEQ ID NO: 3), was fused to GLuc. (D) Luciferase activity assay for primary podocytes from Tg-WT, Tg-C321R and Lamb2$^{+/-}$ mice at P27 transduced with lentivirus expressing SERCaMP or GLuc-STOP. 48 hours after the virus infection, luciferase activity was measured in the medium and normalized to the value in Tg-WT. Mean±SD from 3 independent experiments. *P<0.05; NS: not significant by ANOVA.

Phosphorylation of RyR2 Contributes to Podocyte ER Calcium Depletion in Mutant Podocytes To gain insight into the mechanism underlying intracellular calcium dysregulation in the mutant podocytes undergoing ER stress, RNA sequencing of primary podocytes (passage 0) isolated from Tg-WT and Tg-C321R mice at P27 was performed. Gene set enrichment analysis (GSEA) revealed that expression of genes involved in calcium signaling was significantly increased in Tg-C321R podocytes compared with Tg-WT podocytes (see e.g., FIG. 4A). A detailed profile (including gene rank in gene list, rank metric score, running enrichment score (ES), and core enrichment) of the genes analyzed by GSEA is shown in TABLE 1.

TABLE 1

Gene rank in gene list, rank metric score, running enrichment score (ES), and core enrichment of genes included in GSEA.

| Gene Symbol | Rank in Gene List | Rank Metric Score | Running ES | Core Enrichment |
|---|---|---|---|---|
| PDGFRB | 99 | 1.410113931 | 0.020506648 | Yes |
| PLCB2 | 276 | 1.1281147 | 0.033080984 | Yes |
| CD38 | 288 | 1.119413257 | 0.052035376 | Yes |
| P2RX1 | 317 | 1.094357014 | 0.06988289 | Yes |
| P2RX7 | 344 | 1.068946123 | 0.08736942 | Yes |
| ATP2A3 | 359 | 1.064842463 | 0.10525983 | Yes |
| CHRM2 | 472 | 1.013872385 | 0.11838848 | Yes |
| ITPKB | 586 | 0.972600222 | 0.13076267 | Yes |
| PTAFR | 627 | 0.948414862 | 0.1456073 | Yes |
| MYLK | 644 | 0.944312453 | 0.16133079 | Yes |
| AGTR1A | 729 | 0.909538627 | 0.17376049 | Yes |
| F2R | 778 | 0.889754117 | 0.1872724 | Yes |
| PDGFRA | 864 | 0.854739964 | 0.19871333 | Yes |
| AVPR1A | 1016 | 0.798218787 | 0.20656294 | Yes |
| NOS3 | 1258 | 0.734969497 | 0.20975472 | Yes |
| SPHK1 | 1494 | 0.679501176 | 0.21222322 | Yes |
| TACR1 | 1553 | 0.665862381 | 0.22146119 | Yes |
| NOS2 | 1583 | 0.660674512 | 0.23175716 | Yes |
| CACNA1A | 1696 | 0.641712666 | 0.24980457 | Yes |
| CHRNA7 | 1740 | 0.635790467 | 0.25911537 | Yes |
| EDNRB | 1767 | 0.632647872 | 0.2690446 | Yes |
| ADORA2B | 1999 | 0.59610939 | 0.27022696 | Yes |
| MYLK3 | 2173 | 0.570175886 | 0.27325577 | Yes |
| PLCB3 | 2234 | 0.563309968 | 0.28063825 | Yes |
| ADORA2A | 2657 | 0.537881017 | 0.27325213 | Yes |
| CACNA1E | 2850 | 0.527458906 | 0.274789 | Yes |
| HTR2B | 3042 | 0.523973405 | 0.27630508 | Yes |
| DRD1 | 3124 | 0.517434597 | 0.28206176 | Yes |
| ADCY4 | 3824 | 0.498291165 | 0.26302612 | Yes |
| STIM1 | 3873 | 0.494133085 | 0.2696853 | Yes |
| SLC8A1 | 3881 | 0.493384331 | 0.27795434 | Yes |
| TRHR2 | 4457 | 0.438746691 | 0.26279527 | Yes |
| HRH1 | 4548 | 0.430426866 | 0.26668862 | Yes |
| ADCY7 | 4600 | 0.425532579 | 0.27204084 | Yes |
| ATP2B4 | 4629 | 0.422857314 | 0.27825704 | Yes |
| PPP3CA | 4727 | 0.416302145 | 0.28162867 | Yes |
| SLC25A31 | 4780 | 0.41224736 | 0.2867112 | Yes |
| ERBB4 | 4844 | 0.407592118 | 0.29127768 | Yes |
| PDE1C | 4850 | 0.40718326 | 0.29813275 | Yes |
| PRKACA | 4884 | 0.404372752 | 0.30383086 | Yes |
| RYR2 | 5281 | 0.373151571 | 0.2946205 | Yes |
| CAMK2D | 5289 | 0.372842312 | 0.3008016 | Yes |
| EGFR | 5301 | 0.372201681 | 0.30681324 | Yes |
| PLCG2 | 5319 | 0.370584369 | 0.31255943 | Yes |
| CACNA1C | 5580 | 0.349621534 | 0.30832443 | Yes |
| CAMK4 | 5706 | 0.340954274 | 0.30928266 | Yes |
| LTB4R2 | 5751 | 0.337851971 | 0.31339318 | Yes |
| GRIN1 | 5787 | 0.335853487 | 0.31782532 | Yes |
| NOS1 | 5844 | 0.333010405 | 0.321377 | Yes |
| PRKACB | 5957 | 0.324430496 | 0.3225636 | Yes |
| ITPKA | 6259 | 0.304564804 | 0.31592536 | No |
| HTR4 | 6560 | 0.28544727 | 0.30899554 | No |
| ERBB2 | 6730 | 0.276365817 | 0.3070935 | No |
| PLCB4 | 6950 | 0.264296085 | 0.30300334 | No |
| PPIF | 7226 | 0.246755347 | 0.29639286 | No |
| ITPR1 | 7299 | 0.24142921 | 0.29772496 | No |
| PDE1A | 7370 | 0.237642229 | 0.29907063 | No |
| ORAI2 | 7393 | 0.236504719 | 0.30229643 | No |
| ATP2A2 | 7402 | 0.235748753 | 0.3060633 | No |
| SPHK2 | 7715 | 0.216123208 | 0.29745772 | No |
| ADRB2 | 7893 | 0.206066892 | 0.29402137 | No |
| PLN | 8010 | 0.200679213 | 0.29290608 | No |
| SLC8A3 | 8207 | 0.193581387 | 0.28850138 | No |
| ADRB1 | 8469 | 0.18304801 | 0.28134155 | No |
| PPP3R1 | 8531 | 0.182279348 | 0.28208447 | No |
| GNAL | 8626 | 0.177047193 | 0.2814306 | No |
| PRKCB | 8796 | 0.16756089 | 0.2776439 | No |
| GNA15 | 9009 | 0.157241717 | 0.27197647 | No |
| ATP2B2 | 9041 | 0.156293482 | 0.2734567 | No |
| OXTR | 9203 | 0.149155736 | 0.26966783 | No |
| PLCD1 | 9344 | 0.144071519 | 0.2666221 | No |
| HRH2 | 9409 | 0.140234157 | 0.266518 | No |
| ADCY1 | 9486 | 0.135632753 | 0.26585922 | No |
| P2RX5 | 9594 | 0.131429374 | 0.26390064 | No |
| GRM1 | 9648 | 0.129080668 | 0.26403874 | No |
| NTSR1 | 9651 | 0.129080668 | 0.26619545 | No |
| PTK2B | 9679 | 0.128037915 | 0.26734456 | No |
| PPP3CC | 9985 | 0.116183281 | 0.25728497 | No |
| ADCY3 | 10144 | 0.109252907 | 0.25292367 | No |
| PDE1B | 10204 | 0.106270552 | 0.2524292 | No |
| CHRM3 | 10251 | 0.104030296 | 0.25241044 | No |
| CHRM1 | 10257 | 0.103894219 | 0.2540121 | No |
| ADCY2 | 10342 | 0.10003797 | 0.25242016 | No |
| PLCG1 | 10345 | 0.099857457 | 0.25407067 | No |
| CACNA1D | 10411 | 0.09693417 | 0.25317696 | No |
| CAMK2A | 10587 | 0.086848609 | 0.24775472 | No |
| PHKG2 | 10621 | 0.085596338 | 0.24793121 | No |
| HTR2C | 10670 | 0.08333239 | 0.24747479 | No |
| ADRA1D | 10719 | 0.08333239 | 0.24701835 | No |
| CACNA1H | 10958 | 0.08333239 | 0.23904164 | No |
| CACNA1S | 10959 | 0.08333239 | 0.24048507 | No |
| GRIN2C | 11091 | 0.08333239 | 0.23674347 | No |
| ATP2B3 | 11209 | 0.08333239 | 0.23355599 | No |
| PPP3R2 | 11272 | 0.08333239 | 0.23254544 | No |
| TBXA2R | 11467 | 0.083273672 | 0.22630924 | No |
| P2RX4 | 11610 | 0.075534053 | 0.22199717 | No |
| ADCY9 | 11798 | 0.065762453 | 0.21573472 | No |
| RYR1 | 11901 | 0.06045064 | 0.21274461 | No |
| P2RX3 | 12135 | 0.048316438 | 0.20435926 | No |
| CALM3 | 12192 | 0.045939781 | 0.2029385 | No |
| CALML4 | 12211 | 0.045224238 | 0.2030094 | No |
| GNA11 | 12307 | 0.040190082 | 0.1999454 | No |
| SLC8A2 | 12363 | 0.037426185 | 0.19841675 | No |
| CACNA1G | 12732 | 0.019237598 | 0.18418437 | No |
| PHKA1 | 12868 | 0.012959976 | 0.1790655 | No |
| ORAI1 | 13104 | 0.002622269 | 0.1698095 | No |
| VDAC2 | 13482 | −0.014938378 | 0.15514643 | No |
| CAMK2G | 13556 | −0.018229784 | 0.15257283 | No |
| MYLK4 | 13694 | −0.023544491 | 0.14755806 | No |
| ITPR2 | 13806 | −0.027200989 | 0.1436358 | No |
| GRIN2D | 13942 | −0.032465409 | 0.13885479 | No |
| ADRB3 | 14105 | −0.040411133 | 0.13314272 | No |
| CALM1 | 14196 | −0.043697622 | 0.13033739 | No |
| GNAQ | 14438 | −0.054367375 | 0.12174022 | No |
| PLCD3 | 14712 | −0.065596476 | 0.11207098 | No |
| ORAI3 | 14818 | −0.071340106 | 0.109150745 | No |
| ADRA1B | 15334 | −0.0983494 | 0.09047036 | No |
| MYLK2 | 15347 | −0.099110007 | 0.09171212 | No |
| PPP3CB | 15522 | −0.107924804 | 0.08669452 | No |
| PTGER1 | 15655 | −0.114971913 | 0.08346138 | No |
| PLCD4 | 15920 | −0.127797306 | 0.07522576 | No |
| PRKCA | 16007 | −0.132582709 | 0.07411836 | No |
| PHKB | 16075 | −0.135451064 | 0.07381267 | No |
| EDNRA | 16583 | −0.160114959 | 0.056518797 | No |
| GNA14 | 16663 | −0.163629368 | 0.056226227 | No |
| ADCY8 | 16737 | −0.167586446 | 0.05623968 | No |
| CCKAR | 16769 | −0.168847993 | 0.057937365 | No |
| CALM2 | 16798 | −0.17041707 | 0.05978097 | No |
| PTGER3 | 16906 | −0.176907167 | 0.05861014 | No |
| BDKRB2 | 17014 | −0.182164624 | 0.057530373 | No |
| HTR5B | 17061 | −0.184984565 | 0.05891386 | No |
| P2RX6 | 17103 | −0.187770873 | 0.06054351 | No |
| PHKG1 | 17182 | −0.191487655 | 0.060773067 | No |
| TNNC1 | 17294 | −0.197911486 | 0.059807736 | No |
| TNNC2 | 17451 | −0.206166804 | 0.05720428 | No |
| CACNA1F | 17477 | −0.207696885 | 0.059812363 | No |
| HTR2A | 17527 | −0.210220739 | 0.061514232 | No |
| VDAC1 | 17768 | −0.223877475 | 0.05589279 | No |
| CYSLTR1 | 17952 | −0.234213576 | 0.052706473 | No |
| ATP2B1 | 17975 | −0.235648155 | 0.055917453 | No |
| BDKRB1 | 18072 | −0.241508141 | 0.056300983 | No |
| CACNA1B | 18705 | −0.281539202 | 0.036162786 | No |
| STIM2 | 18858 | −0.292550206 | 0.03521393 | No |

TABLE 1-continued

Gene rank in gene list, rank metric score, running enrichment score (ES), and core enrichment of genes included in GSEA.

| Gene Symbol | Rank in Gene List | Rank Metric Score | Running ES | Core Enrichment |
|---|---|---|---|---|
| ITPKC | 19031 | −0.304297954 | 0.033676952 | No |
| PLCE1 | 19132 | −0.310789257 | 0.035102203 | No |
| GNAS | 19181 | −0.314664572 | 0.038652766 | No |
| GRPR | 19251 | −0.31980446 | 0.041461166 | No |
| P2RX2 | 19816 | −0.328203887 | 0.024822738 | No |
| CACNA1I | 19931 | −0.329604328 | 0.026019769 | No |
| CALM4 | 20425 | −0.338997573 | 0.012378512 | No |
| CYSLTR2 | 20556 | −0.342508465 | 0.013165771 | No |
| CALML3 | 20788 | −0.345310926 | 0.010003949 | No |
| PHKA2 | 21021 | −0.363582462 | 0.007119034 | No |
| SLC25A4 | 21162 | −0.375091374 | 0.008074869 | No |
| MCU | 21606 | −0.394050211 | −0.002633777 | No |
| HTR7 | 21655 | −0.398845673 | 0.002374917 | No |
| VDAC3 | 21668 | −0.399238706 | 0.008815315 | No |
| CAMK2B | 21725 | −0.403389901 | 0.013586077 | No |
| ADRA1A | 21741 | −0.404718935 | 0.020002658 | No |
| HTR6 | 21777 | −0.407536685 | 0.025676439 | No |
| SLC25A5 | 21835 | −0.411562532 | 0.030549182 | No |
| TACR2 | 22194 | −0.44660759 | 0.02411524 | No |
| ITPR3 | 22259 | −0.45298183 | 0.02942836 | No |
| ERBB3 | 22595 | −0.49291262 | 0.024706833 | No |
| PLCB1 | 22701 | −0.50636971 | 0.029321905 | No |
| AGTR1B | 23172 | −0.56456697 | 0.020498173 | No |
| TACR3 | 23400 | −0.576457977 | 0.021498457 | No |
| PTGFR | 23535 | −0.587186873 | 0.02636556 | No |
| AVPR1B | 23762 | −0.608450353 | 0.027959576 | No |
| CHRM5 | 23804 | −0.613890529 | 0.036970206 | No |
| GRIN2A | 24411 | −0.741415739 | 0.025826795 | No |
| ATP2A1 | 24785 | −0.85115695 | 0.025806496 | No |

Figure 4B:
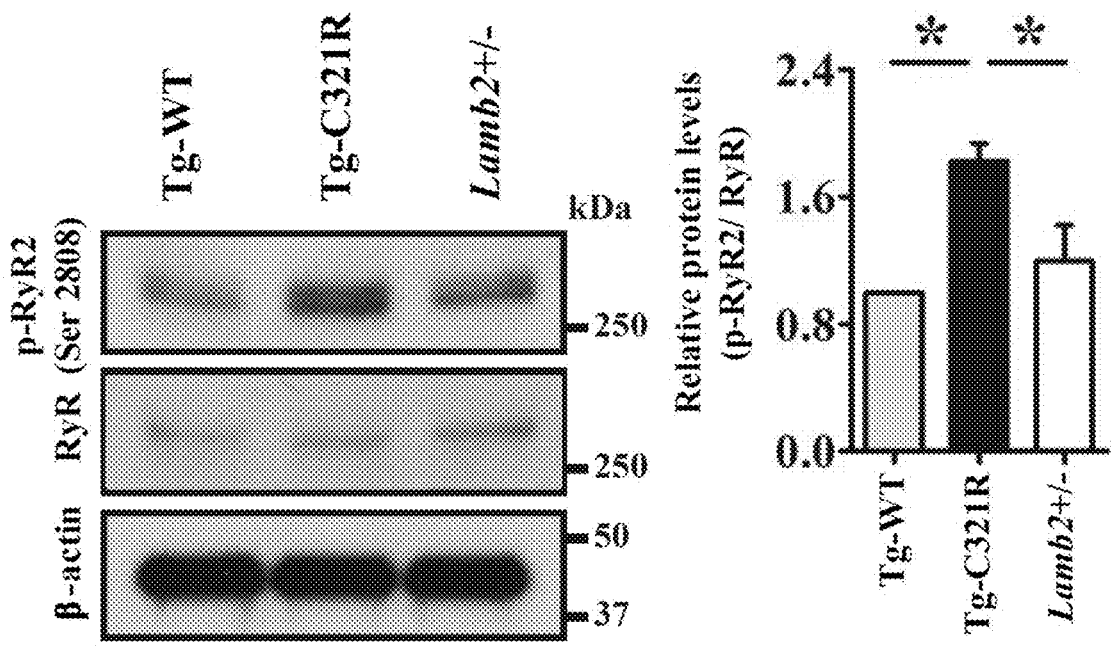
Figure 4C:
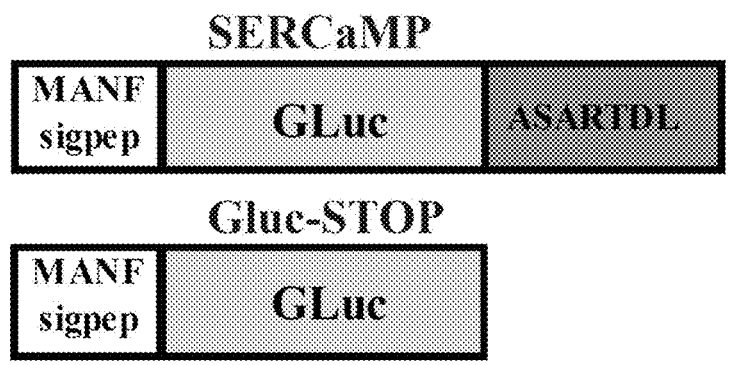
Figure 10:
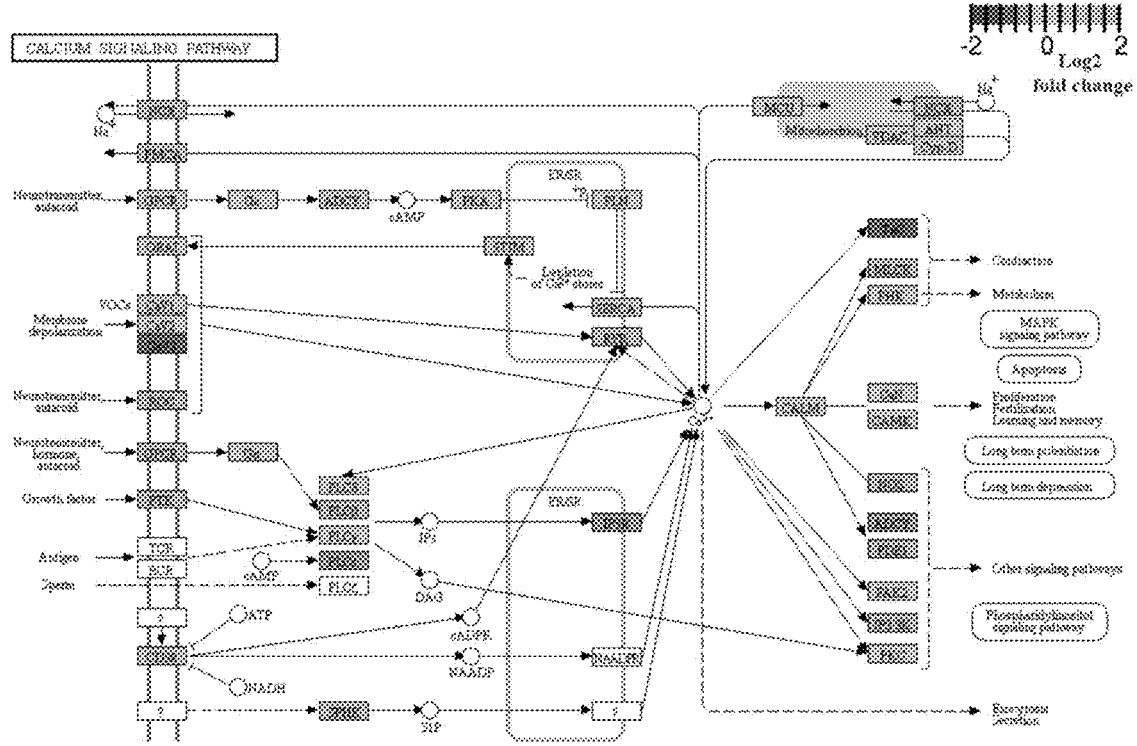
FIG. 10. KEGG pathway analysis of dysregulated calcium signaling pathway in Tg-C321R podocytes compared with Tg-WT podocytes. Enrichment analysis showed that calcium signaling pathway is deregulated in Tg-C321R podocytes versus Tg-WT podocytes. The KEGG pathway depicts the molecules that are involved in the calcium signaling pathway. Color indicates the magnitude of gene expression changes. The most upregulated genes in the pathway are highlighted in orange, whereas the most downregulated genes are blue.

Furthermore, Kyoto Encyclopedia of Genes and Genomes (KEGG) calcium-signaling pathway depicting significantly deregulated molecules showed that RyR expression was upregulated with downregulation of IP3R and upregulation of SERCA in the mutant podocytes versus Tg-WT podocytes (see e.g., FIG. 10), suggesting that aberrant RyR may mediate ER calcium leak, contributing to cytosolic calcium overload in podocytes under ER stress. RyR expression was next examined at the protein level. Western Blot did not reveal difference of RyR expression among the different groups by using an anti-RyR antibody that recognizes all three isoforms of RyR (see e.g., FIG. 4B). Since it has been shown that RyR2 isoform is present in the rabbit kidney cortex and its activity is modulated by phosphorylation of the channel, phosphorylation of RyR2 at Ser2808 was further examined. In cardiomyocytes, chronic hyperphosphorylation of RyR2-Ser2808 in heart failure and ventricular arrhythmia has been shown to be critical in causing diastolic sarcoplasmic reticulum calcium leak by destabilizing the closed state of the channel. Here, mutant podocytes showed increased phosphorylation of RyR2 at Ser2808 compared with control podocytes at the early stage of disease (see e.g., FIG. 4B). Finally, to demonstrate that ER calcium was depleted due to augmented ER calcium release in live podocytes, podocyte ER calcium homeostasis was monitored by utilizing secreted ER calcium-monitoring proteins (SERCaMPs). It has been shown that the carboxy-terminal sequence of an ER stress protein MANF (mesencephalic astrocyte-derived neurotrophic factor), ASARTDL (SEQ ID NO: 3), is sufficient to specifically confer ER calcium-depletion-dependent secretion. In SERCaMP, ASARTDL (SEQ ID NO: 3) is appended to an unrelated secreted protein Gaussia Luciferase (GLuc), and the first 18 amino acids of GLuc were replaced with the signal peptide of MANF to target GLuc to the secretory pathway (see e.g., FIG. 4C).

Figure 11A:
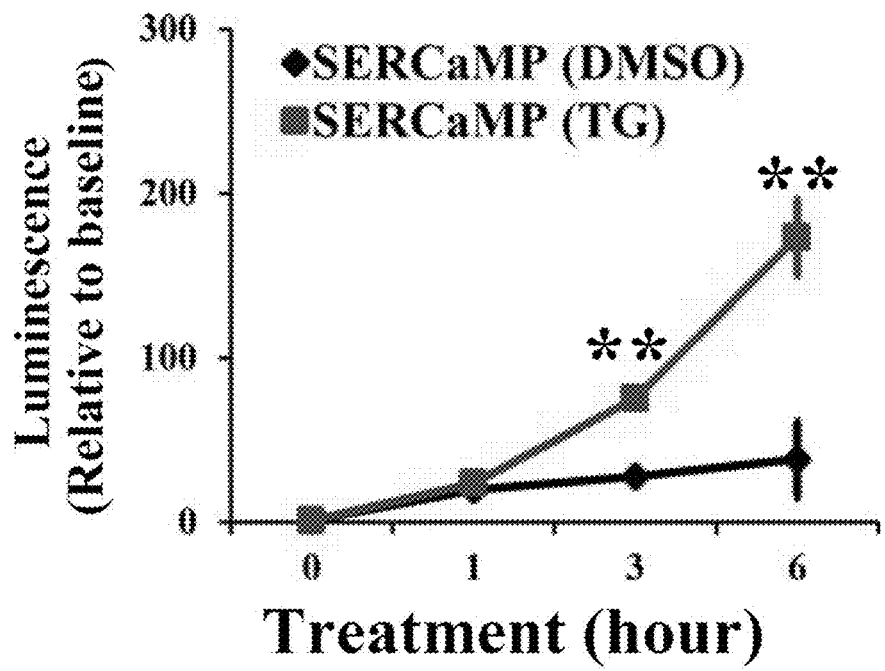
FIG. 11A-FIG. 11B. SERCaMP secretion is specifically triggered by ER calcium depletion. 293T cells stably expressing (A) SERCaMP or (B) control GLuc-STOP were treated with 0.1 µM TG or DMSO, for varying durations. Luciferase activity was measured in the medium (mean±SD, n=3) and normalized to the respective baseline. **P<0.01 by t-test.
Figure 11B:
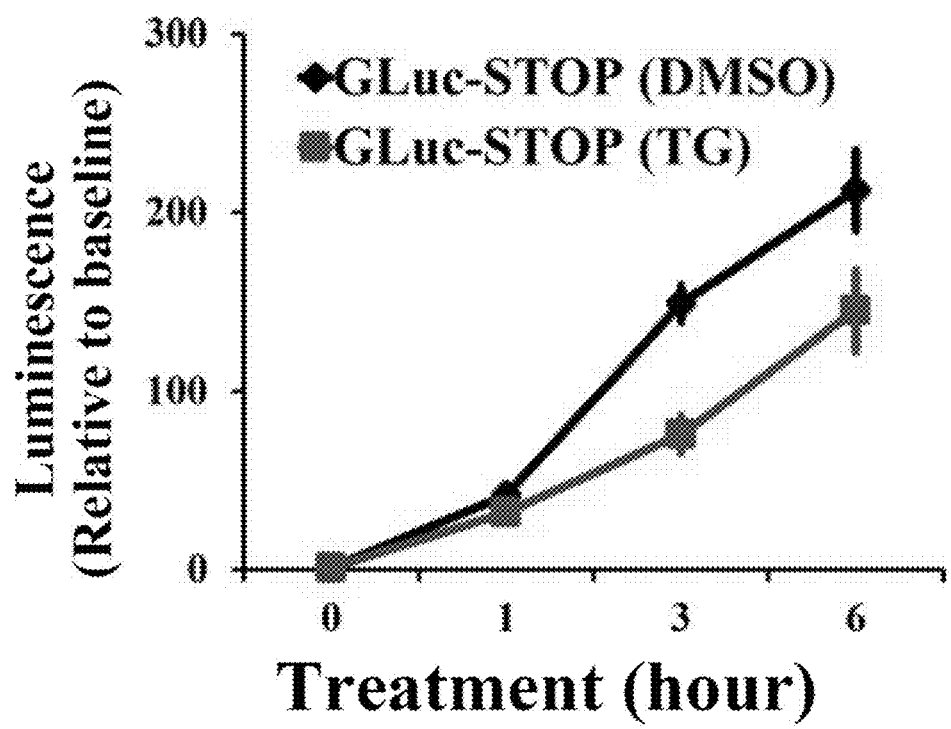

The GLuc-based SERCaMP is localized to the lumen of the ER under normal conditions, whereas it is secreted specifically in response to ER calcium depletion. When human embryonic kidney (HEK) 293T cells stably expressing SER-CaMP or control GLuc-STOP without the ASARTDL tag were treated with DMSO or 0.1 µM thapsigargin (TG), a SERCA inhibitor causing ER calcium depletion for 6 hours, SERCaMP secretion, as measured by luciferase activity in the cell culture medium, was increased in response to ER calcium depletion induced by TG (see e.g., FIG. 11A and FIG. 11B). Importantly, when equal numbers of Tg-C321R as well as control Tg-WT and WT primary podocytes, which were isolated from the respective mice at P27, were transduced with lentivirus expressing SERCaMP or GLuc-STOP for 48 hours, luciferase assay showed that secreted SER-CaMP by Tg-C321R podocytes was significantly increased compared with that by control podocytes (see e.g., FIG. 4D). In contrast, secretion of untagged GLuc did not differ among the different genotypes (see e.g., FIG. 4D). In summary, these data demonstrate that podocyte RyR2 hyperphosphorylation is one molecular mechanism mediating the accelerated podocyte ER-to-cytosol calcium efflux and ER calcium depletion before significant proteinuria.

Identification of K201 as a Novel Podocyte ER Stabilizer

Figure 5A:
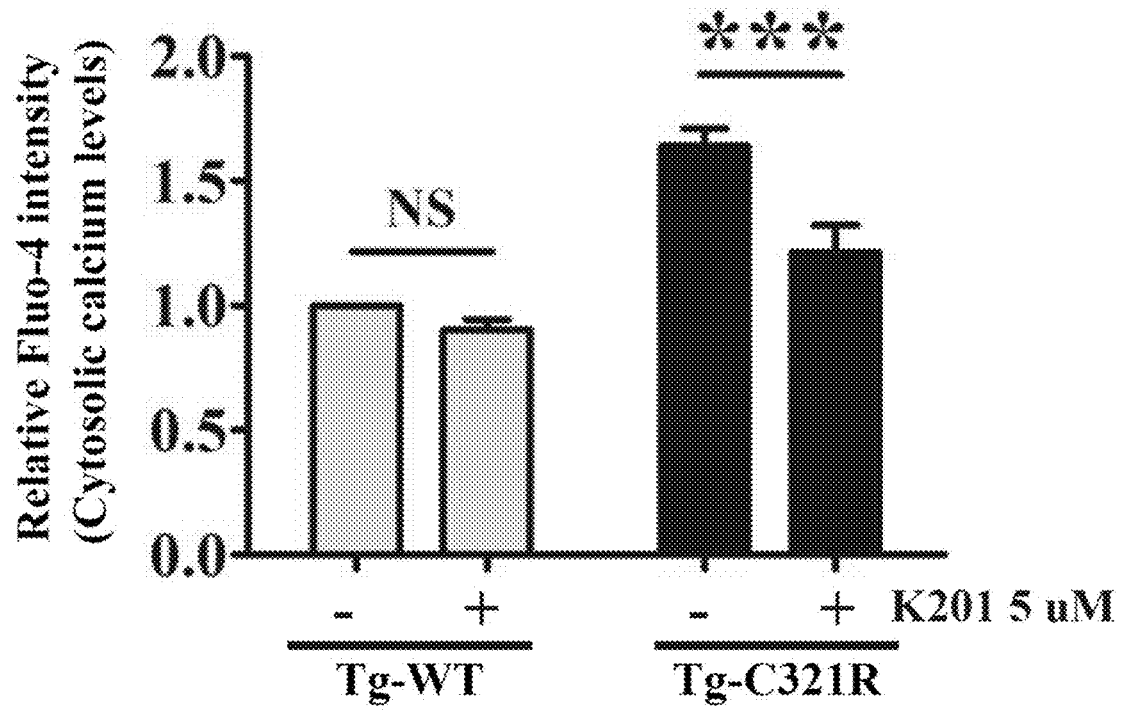
FIG. 5A-FIG. 5E. K201 attenuates ER calcium release, downstream calpain 2-caspase 12 activation, and apoptosis in Tg-C321R podocytes. Cultured primary podocytes from Tg-WT and Tg-C321R mice at P27 were treated with 5 μM K201 or DMSO (vehicle control) for 24 hours. (A) Cytosolic calcium levels in DMSO- and K201-treated podocytes measured by cytosolic calcium indicator Fluo-4. Mean±SD of 3 independent experiments. ***P<0.001 by ANOVA. Podocyte lysates treated with or without K201 were analyzed by Western blot for levels of (B) p-RyR2 (S2808) and RyR, (C) cleaved spectrin and talin 1, and (D) cleaved caspase 12 and caspase 3. Arrows indicate cleaved proteins. (E) Flow cytometry analysis of Annexin V$^+$/PI$^-$ podocytes in the presence or absence of K201. The percentage of early apoptotic cells was expressed as Mean±SD from 3 independent experiments. *P<0.05 by ANOVA.
Figure 12:
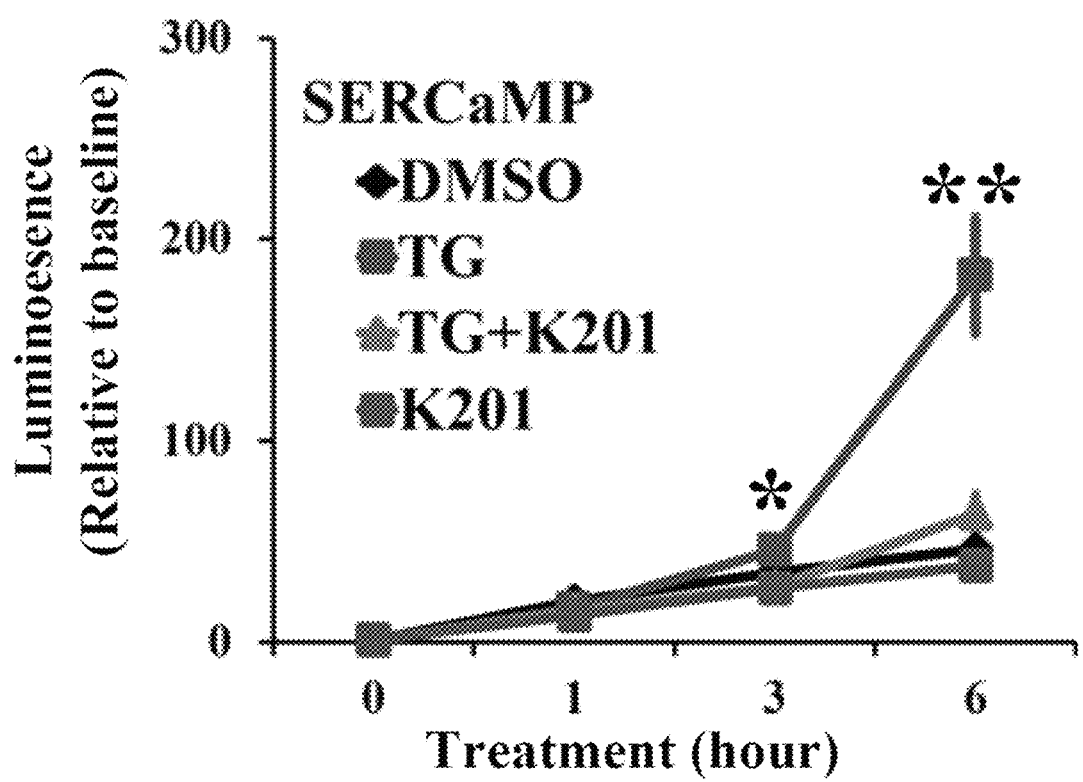
FIG. 12. K201 inhibits ER calcium depletion induced by thapsigargin (TG). 293T cells stably expressing SERCaMP were treated with DMSO, 0.1 µM TG, 1 µM K201+TG or K201 alone for 6 hours. GLuc activity was measured in the medium (mean±SD, n=3) and normalized to the respective baseline. *P<0.05 and **P<0.01 TG vs. TG+K201 by ANOVA with Tukey multiple comparisons.

The effect of a previously reported ER calcium release inhibitor K201, which is known to stabilize the closed state of RyR2 calcium channel in cardiomyocytes during heart failure or cardiac arrhythmia, was tested on podocytes. First, it was confirmed that K201 can abrogate TG-induced ER calcium depletion in HEK 293T cells (see e.g., FIG. 12). Then, primary podocytes isolated and cultured from Tg-WT and Tg-C321R mice at P27, were treated with K201 at 5 µM for 24 hours. Based on 3-(4, 5-dimethylthiazol-2-yl)-2, 5-diphenyltetrazolium bromide (MTT) cell viability assay, 1-5 µM of K201 was noted to be non-toxic to primary podocytes. K201 markedly blocked the increased podocyte ER-to-cytosol calcium leak in Tg-C321R podocytes, as measured by the cytosolic calcium indicator Fluo-4 (see e.g., FIG. 5A). Mechanistically, treatment with K201 inhibited hyperphosphorylation of RyR2 at Ser2808 in the mutant podocytes (see e.g., FIG. 5B). Consequently, K201 suppressed overactivation of calpain 2, as indicated by the decreased cleavage of alpha II spectrin, as well as cytoskeletal protein talin 1 in the mutant podocytes (see e.g., FIG. 5C). Furthermore, K201 treatment abolished its downstream activation of procaspases 12 and 3 in the ER-stressed podocytes (see e.g., FIG. 5D). Ultimately, K201 significantly decreased early apoptotic rate in Tg-C321R podocytes (Annexin $V^+/PI^-$ cells) from 24.73±2.22% to 15.23±2.84% ($P<0.05$) (see e.g., FIG. 5E). The higher apoptotic rates in all groups were most likely due to the effect of DMSO. These results provide direct measurements of the effects of K201 in ameliorating podocyte ER stress-induced calcium leak and protecting against apoptosis in primary podocytes under ER stress.

Figure 6A:
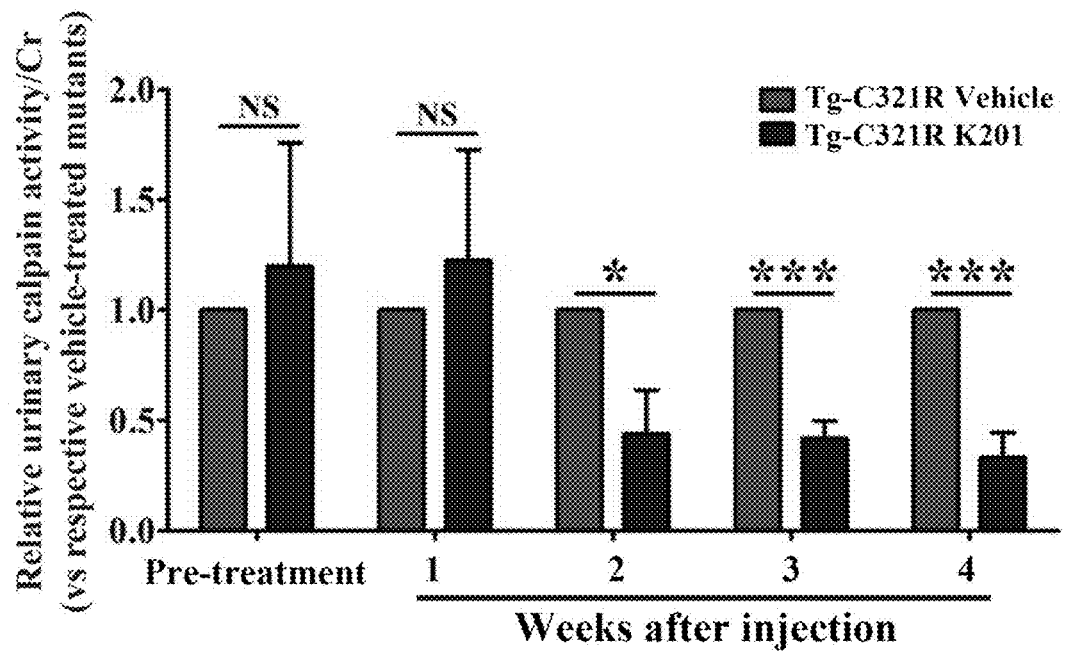
FIG. 6A-FIG. 6C. K201 mitigates podocyte ER stress-mediated proteinuric kidney disease progression, inhibiting urinary calpain activity and attenuating albuminuria. (A) Urinary calpain activity/Cr in both K201- and 20% (2-hydroxypropyl)-β-cyclodextrin (HBC)-treated Tg-C321R mice at pre-treatment (P17-19) and at weekly intervals post-treatment, demonstrating K201 inhibits urinary calpain activity in Tg-C321R mice after two weeks of injection. The urinary calpain activity/Cr in the 20% HBC-treated Tg-C321R mice at respective time points was set as 1. n=6 per group. *P<0.05; *P<0.001 by t test. (B) Urinary albumin measurements in Tg-C321R mutants treated for 4 weeks with K201 (12.5 mg/kg-15 mg/kg, once daily) intraperitoneal injection starting at 3 weeks of age. The pretreatment albuminuria was measured at P17-19. n=6 per group for vehicle or K201-injected Tg-C321R mice, and n=8 per group for vehicle or K201-injected Lamb2$^{+/-}$ mice. Mean±SD, P<0.01 by ANOVA. (C) Serum BUN of the indicated groups following 4 weeks of K201 or 20% HBC treatment. N=6 per group for vehicle or K201-injected Tg-C321R mice, and n=8 per group for vehicle or K201-injected Lamb2$^{+/-}$ mice. Mean±SD, *P<0.05; NS: not significant by ANOVA.
Figure 6B:
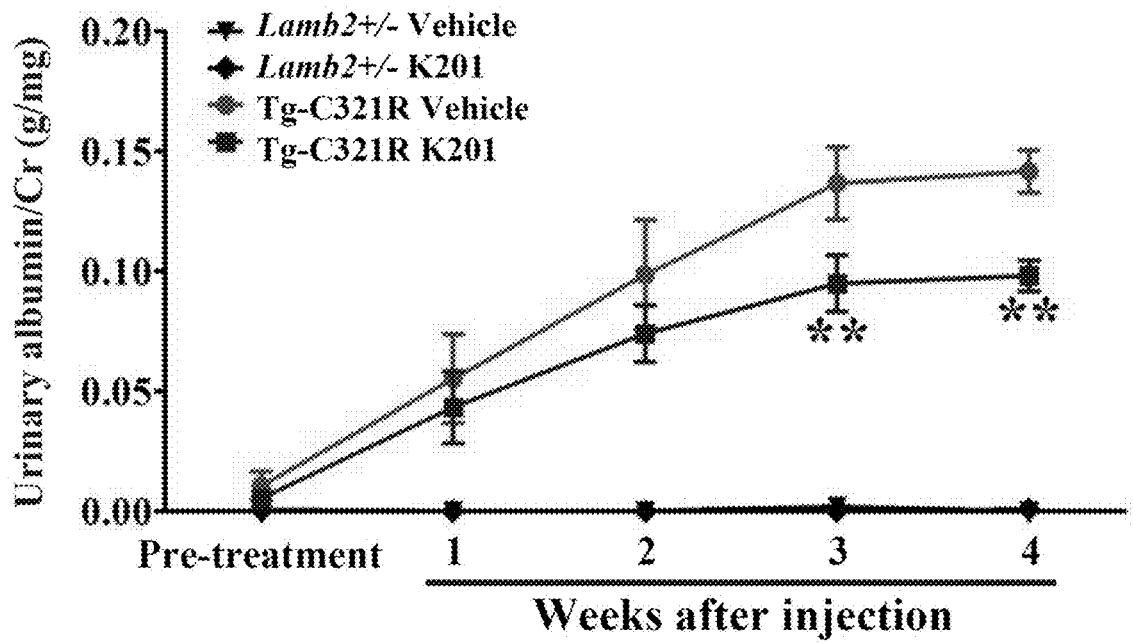
Figure 6C:
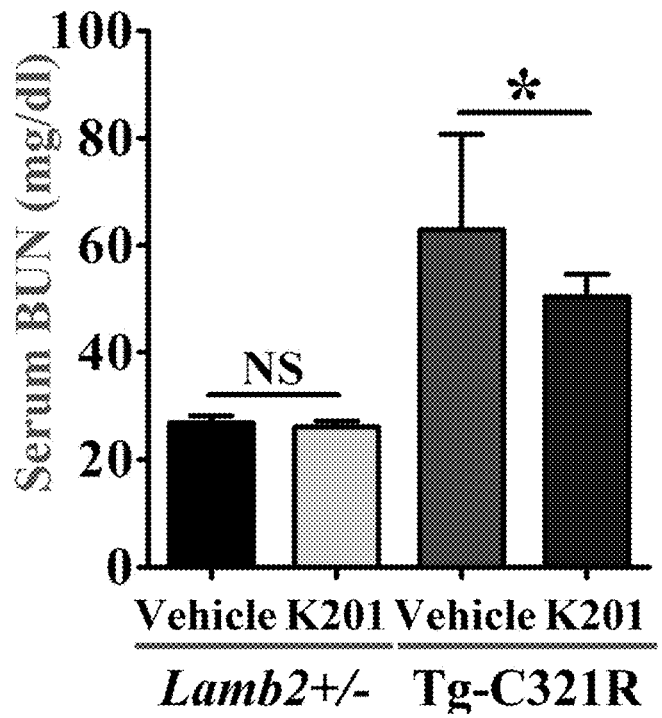
Figure 13:
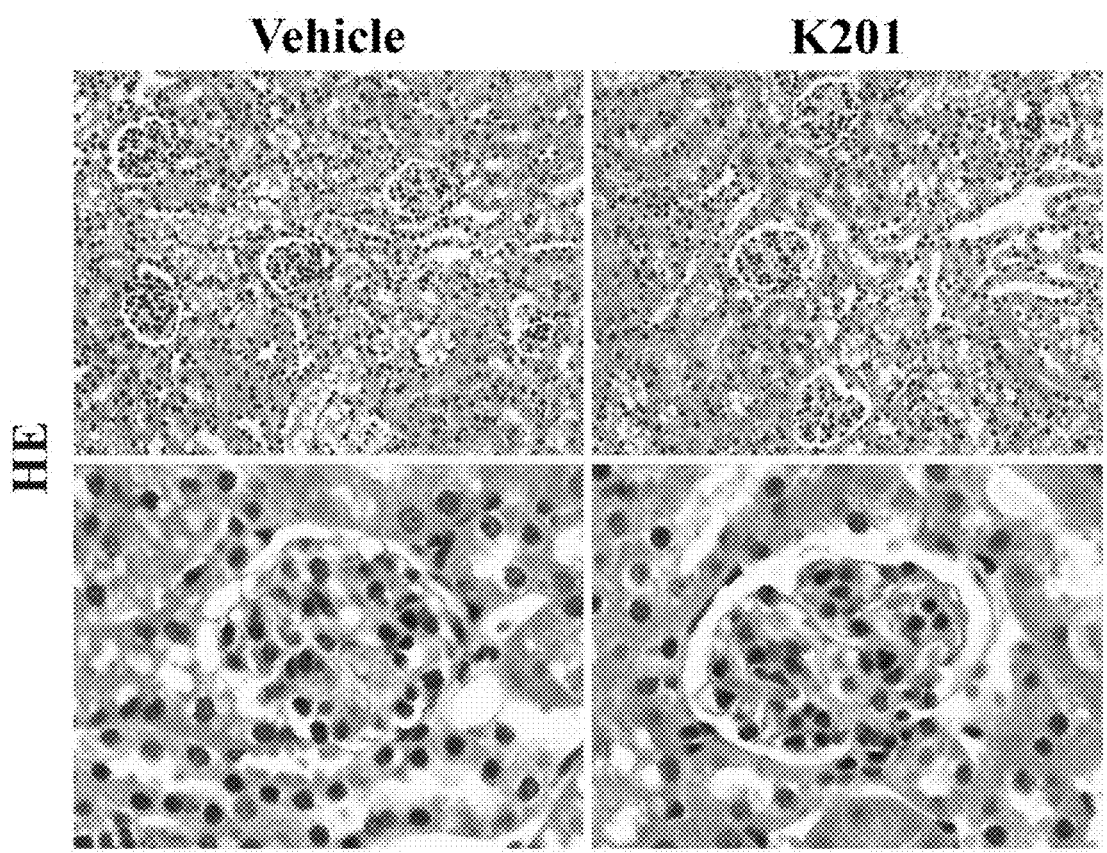
FIG. 13. K201 exhibits no drug toxicity in vivo. Administration of K201 or vehicle (20% HBC) in a cohort of WT (Lamb2$^{+/-}$) mice (n=8 for each group) at 3 weeks of age for 4 weeks. HE staining of K201 or vehicle-injected kidneys at the end of treatment.

To further demonstrate that leaky podocyte RyR2 is an important drug target to induce podocyte injury and that restoring disrupted podocyte ER calcium homeostasis by the RyR2 modulator K201 is therapeutically beneficial, the efficacy of K201 was determined in vivo. At 3 weeks of age when Tg-C321R mutants had developed very mild albuminuria, a cohort of Tg-C321R mice (n=12) and control Lamb2$^{+/-}$ littermates (n=16) was injected intraperitoneally with K201 or vehicle, which is 20% (2-hydroxypropyl)-β-cyclodextrin (HBC), a commonly used non-toxic solubilizer for lipophilic drugs. K201 (12.5 mg/kg in the first week when the weight of mice was around 10 grams or 15 mg/kg afterwards) and 20% HBC were administered once daily, 5 days in a row in a week over a course of 4 weeks. Urinary calpain activity/Cr was dramatically decreased in K201-treated Tg-C321R mutants compared with 20% HBC-treated mutant mice as early as 2 weeks after the treatment and continued to be suppressed by K201 at 4 weeks post-treatment (see e.g., FIG. 6A), indicating that K201 injection effectively blocks ER calcium leak in Tg-C321R podocytes in vivo. Subsequently, K201 treatment significantly reduced albuminuria at 3 weeks (0.095±0.029 versus 0.137±0.037 g/mg Cr) and 4 weeks (0.098±0.016 versus 0.142±0.022 g/mg Cr) post-injection (see e.g., FIG. 6B) as well as improved kidney function as indicated by blood urea nitrogen (BUN) at the end of 4 weeks of injection (see e.g., FIG. 6C). Meanwhile, no abnormality of kidney histology (see e.g. FIG. 13A) and renal function as indicated by blood urea nitrogen (BUN) (see e.g., FIG. 6C) was noted in K201-treated mice as compared to vehicle-treated control littermates. Together, for the first time, this study shows that the podocyte ER RyR2 calcium channel stabilizer K201 can antagonize podocyte ER stress-induced enhanced ER calcium release and proteinuria.

Discovery of MANF as an ER Calcium Channel Stabilizer

Figure 7A:
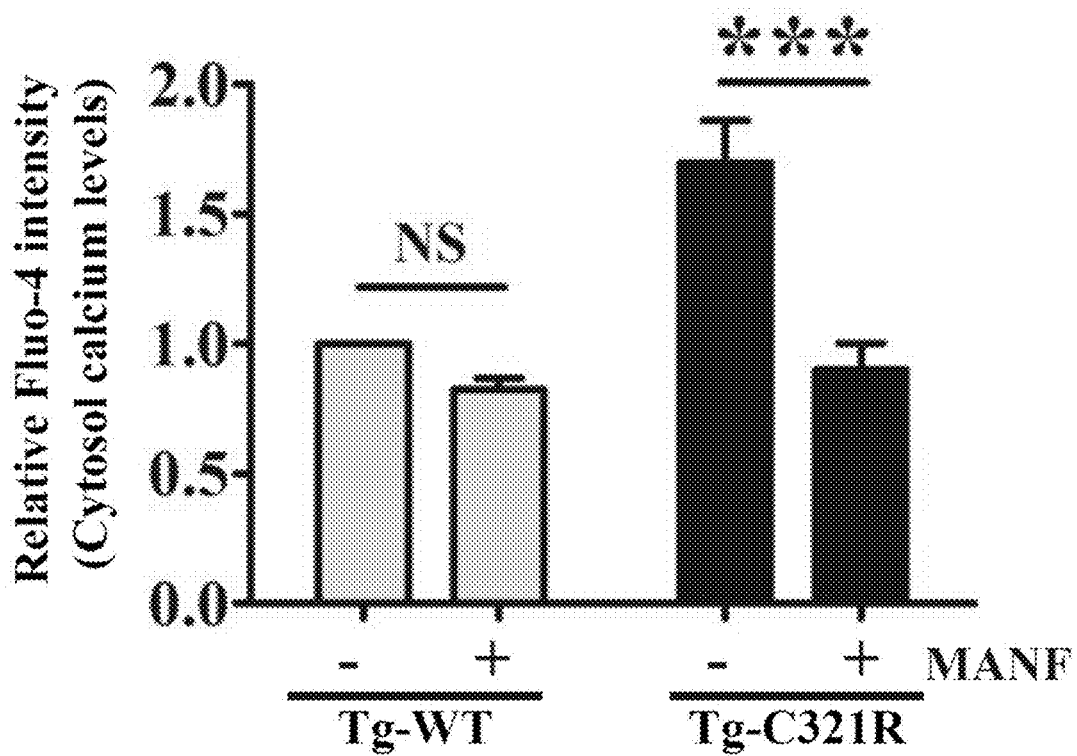
FIG. 7A-FIG. 7F. Recombinant MANF inhibits both calcium-dependent and calcium-independent apoptotic pathways in ER-stressed podocytes. Primary podocytes isolated from Tg-WT and Tg-C321R mice at P27 were treated with 5 µg/ml recombinant MANF or PBS (control) for 24 hours. (A) Cytosolic calcium levels in Tg-WT and Tg-C321R podocytes measured by cytosolic calcium indicator Fluo-4 in the presence or absence of recombinant MANF. Mean±SD of 3 independent experiments. ***P<0.001 by ANOVA. Immunoblot analysis monitoring of (B) p-RyR2 (S2808) and RyR, (C) cleaved spectrin and talin 1, (D) active caspase 12 and CHOP, and (E) XBP1s and ATF4 in control and Tg-C321R podocytes treated with or without MANF. Arrows indicate cleaved proteins. (F) Flow cytometry detection of podocytes undergoing early apoptosis (Annexin V$^+$/PI$^-$ cells) in the presence or absence of MANF. The percentage of early apoptotic cells was expressed as Mean±SD from 3 independent experiments. *P<0.05 by ANOVA.
Figure 7B:
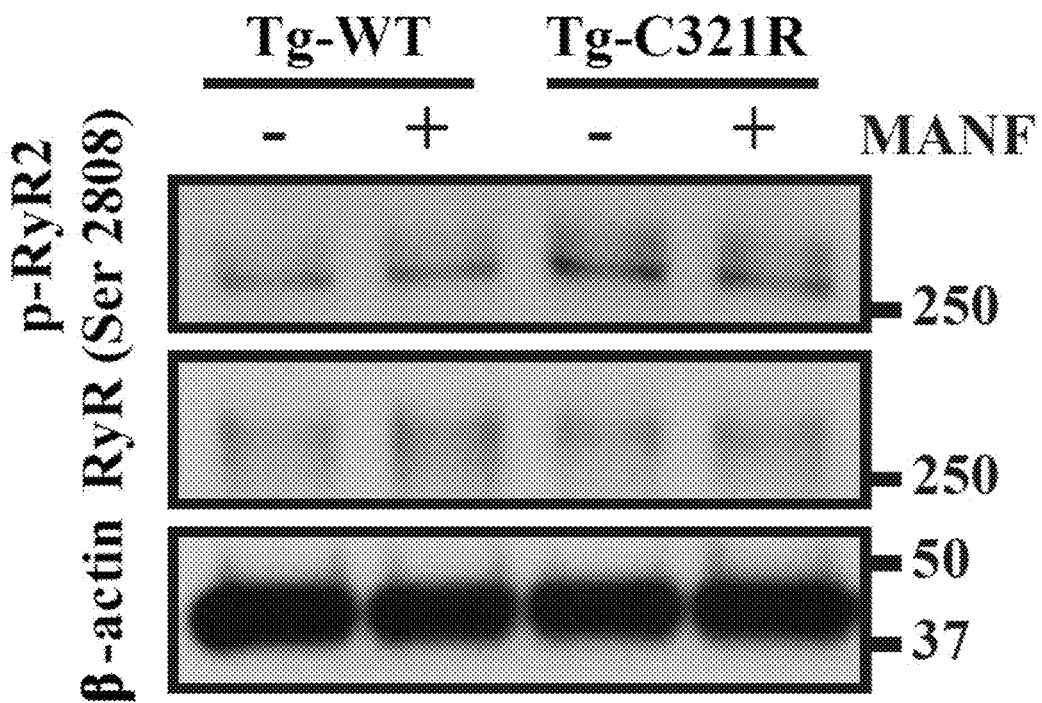
Figure 7C:
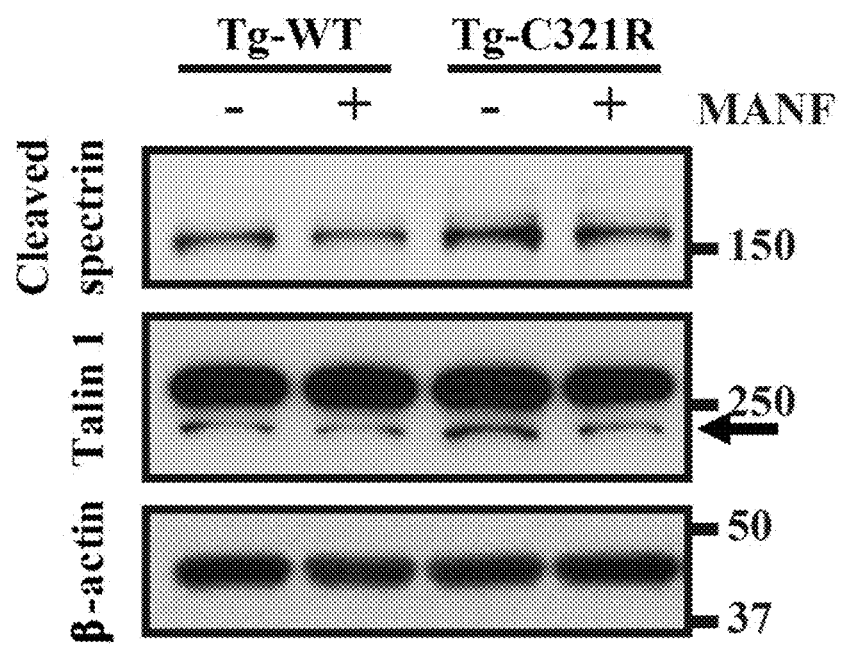
Figure 7D:
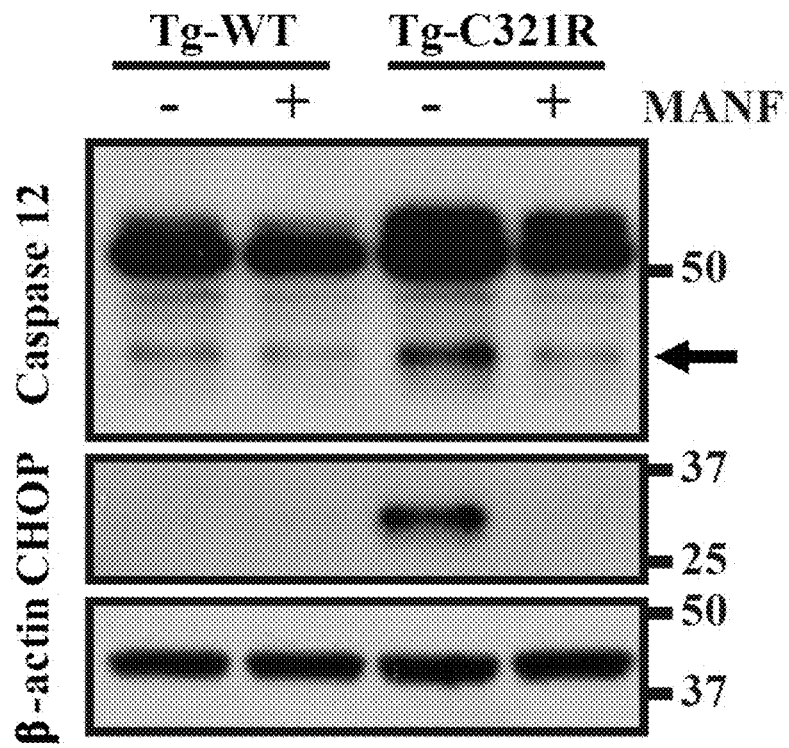
Figure 7E:
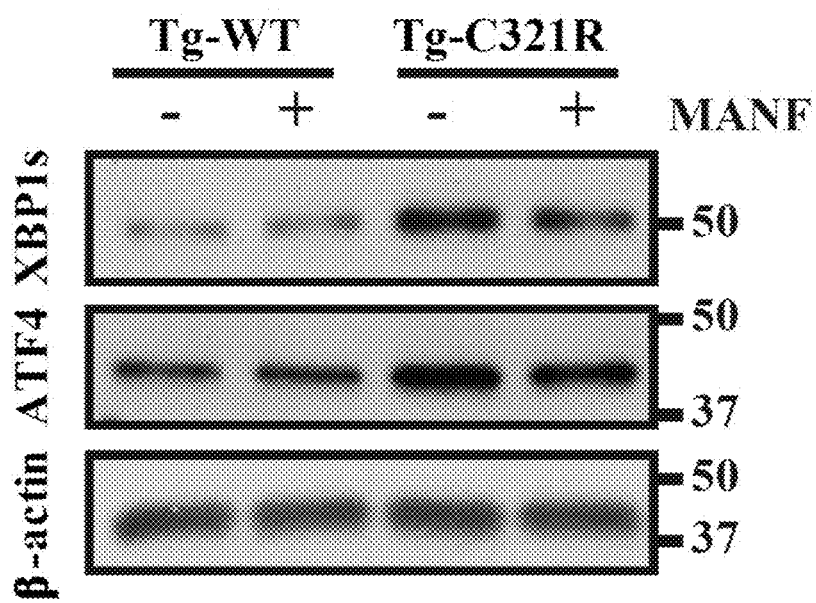
Figure 7F:
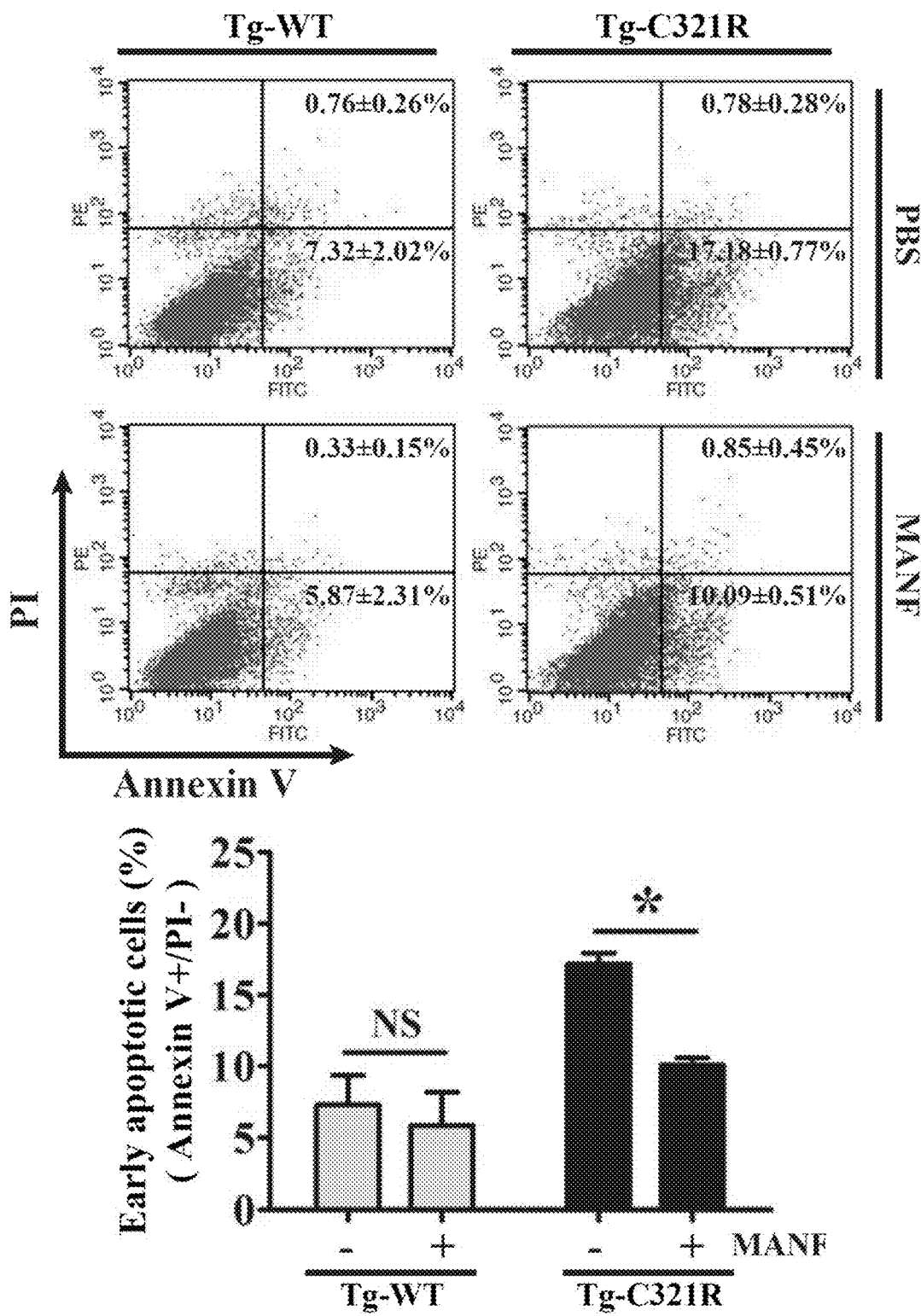

MANF, a newly identified 18 kDa soluble protein, is upregulated in response to experimental ER stress in various cell types. It is retained in the ER by calcium-dependent interaction with BiP, and selectively secreted upon ER calcium depletion. Whether secreted MANF can, in turn, maintain the ER calcium homeostasis has not been investigated. Previously, it has been shown that ER stress induced MANF expression at both transcriptional and translational levels in Tg-C321R podocytes in the early stage of proteinuria. Next, the impact of MANF on primary podocytes isolated from Tg-WT and Tg-C321 mice at P27 was assessed. When control and Tg-C321R podocytes were treated with MANF recombinant protein (5 µg/ml) for 24 hours, cytosolic calcium levels in the mutant podocytes were significantly decreased after the treatment (see e.g., FIG. 7A), which is consistent with reduced phosphorylation of ER RyR2 by the MANF treatment in the mutant podocytes (see e.g., FIG. 7B). As a result, Tg-C321R podocytes treated with MANF showed inhibition of calpain 2 activation, as demonstrated by decreased cleavage of spectrin and talin 1, as well as suppression of active cleaved caspase 12 compared with untreated Tg-C321R podocytes (see e.g., FIG. 7C and FIG. 7D). In addition, CHOP induction in MANF-treated Tg-C321R podocytes was abrogated compared with untreated mutant podocytes (see e.g., FIG. 7D). Since the CHOP gene promoter contains binding sites for the three master transcription factors XBP1s, ATF4 and p50ATF6, and XBP1 s as well as ATF4 were induced in the ER-stressed podocytes (see e.g., FIG. 1A and FIG. 1B), it was therefore reasoned that MANF might suppress the induction of these two transcription factors in the mutant podocytes. Indeed, inhibition of both XBP1s and ATF4 by MANF was observed in the mutant podocytes (see e.g., FIG. 7E). In agreement with the suppression of both caspase 12 and CHOP proapoptotic pathways in Tg-C321R podocytes, MANF treatment substantially attenuated early apoptotic rate (Annexin V$^+$/PI$^-$) in the mutant podocytes from 17.18±0.77% to 10.09±0.51% (P<0.05) at the early stage of disease (see e.g., FIG. 7F). These data show that besides stabilizing ER calcium release channel RyR2, MANF has pleiotropic pro-survival effects to rescue ER-stressed podocytes.

DISCUSSION

The present study shows that hyperphosphorylation of RyR2 in ER-stressed podocytes contributes to increased podocyte ER calcium efflux, leading to downstream activation of calpain 2-caspase 12 proapoptotic pathway at the early stage of NS. These findings have identified an important therapeutic target, ER calcium release channel RyR2 in podocytes, which is involved in podocyte injury. More importantly, the RyR2 inhibitor K201 has been successfully identified, which can suppress podocyte ER calcium leak and subsequent calpain 2-caspase 12 overactivation in podocytes under ER stress, as well as ameliorate proteinuria in the podocyte ER stress-induced monogenic NS mouse model. Most excitingly, for the first time, it has been discovered that MANF can normalize RyR2 complex composition and antagonize podocyte apoptosis in addition to other pro-survival effects. Thus, both a chemical compound and a novel biotherapeutic protein belonging to a new class of drugs—podocyte ER calcium channel stabilizers, which can fix leaky RyR2 in ER-stressed podocytes, have been discovered (see e.g., FIG. 8). RyR2 is a homotetramer comprising four monomers, each containing a transmembrane segment. RyR2 has an enormous cytoplasmic domain that serves as a scaffold for regulator proteins that modulate the channel's activity. The RyR2 cytoplasmic scaffold domain contains kinases (protein kinase A and calcium/calmodulin-dependent kinase A), phosphatases (protein phosphatase 1 and 2a), and Ca$^{2+}$ channel-stabilizing subunit calstabin-2, as well as other modulatory proteins, including phosphodiesterase 4D3, which degrades cyclic adenosine monophosphate (cAMP) and thus inhibits cAMP-dependent protein kinase A activation. Protein kinase A and calcium/calmodulin-dependent kinase A can both phosphorylate different sites (Ser2808, Ser2809, Ser2814, Ser2815, and Ser2030). Mimicking constitutive phosphorylation of RyR2 at Ser2808 in RyR2$^{S2808D/S2808D}$ mice is associated with depletion of calstabin-2, elevated RyR2 oxidation and nitrosylation, resulting in increased diastolic sarcoplasmic reticulum calcium leak in cardiomyocytes. The mice developed age-dependent cardiomyopathy and exhibited increased mortality after myocardial infarction compared with WT littermates. Whether the mutant mice have altered kidney phenotype was not reported. In contrast, genetic ablation of RyR2 phosphorylation at Ser2808 in RyR2$^{S2808A/S2808A}$ mice prevents remodeling of the RyR2 macromolecular complex. These mice are protected against chronic catecholaminergic-induced cardiac dysfunction and development of heart failure after myocardial infarction, as well as against stress-induced cognitive dysfunction. Here for the first time, it has been shown that defective RyR2 channel function due to hyperphosphorylation at Ser2808 in ER-stressed podocytes may be one molecular mechanism underlying the aberrant ER calcium release that can cause podocyte apoptosis and injury. Thus, inhibition of podocyte RyR2 leak is an attractive therapeutic strategy for the treatment of primary NS induced by podocyte ER stress.

K201, also known as JTV-519, is a derivative of 1,4-benzothiazepine that has been shown to stabilize the closed state of RyR2 in cardiomyocytes, thus reducing heart failure progression and ventricular arrhythmia by inhibiting diastolic sarcoplasmic reticulum calcium leak. The investigational drug that was studied in clinical trials for treatment of arrhythmia as well as protection against acute myocardial infarction has an outstanding in vivo safety profile. In the current study, K201 is used successfully to treat ER stress-induced podocytopathy. In addition to inhibiting phosphorylation of RyR2-Ser2808, K201 may exert additional therapeutic effects in correcting the maladaptive remodeling of podocyte RyR2. Other components of the RyR2 macromolecular complex, including protein kinases, phosphatases, calstabin-2, and phosphodiesterase 4D3 warrant further examination.

In the present study, it has also been discovered that MANF reduces phosphorylation of RyR2 at Ser-2808 and confers the protection from the detrimental effects of increased ER calcium efflux in podocytes. It has been found that MANF can mitigate diabetes, exert neurotrophic function in Parkinson's disease, protect cardiac myocytes in myocardial infarction, reduce cortical neuron injury in ischemic stroke, and promote macrophage phenotype switch from proinflammatory to prorepair anti-inflammatory macrophages in animal models. It has also been recently shown that MANF is a urinary biomarker for ER stress-mediated kidney diseases. However, the biological function of this protein has not been studied in kidney disease and the cytoprotective mechanisms remain obscure. Consistent with previous reports that MANF modulates ER stress signaling branches and inhibits CHOP induction in animal models of cerebral ischemia and diabetes, respectively, this study has shown that MANF attenuates the upregulation of ER signaling arms IRE1α-XBP1s and PERK-eIF2α-ATF4, as well as suppresses the ER calcium depletion-independent CHOP apoptotic pathway. In addition, MANF acts on dysfunctional podocyte RyR2 channels to inhibit Ser2808 phosphorylation and calcium leak. Further studies will be performed to determine the molecular mechanism underpinning the protective effect of MANF on the malfunctioning ER calcium release channel in podocytes. Podocyte-specific MANF transgenic mice can be generated to examine in vivo effects of MANF on podocyte ER dysfunction and proteinuria.

In conclusion, this study provides a novel mechanism for treating podocyte ER stress-induced proteinuria that targets podocyte leaky RyR2 channels. This study suggests that development of podocyte ER RyR2 stabilizers may have wide clinical applications in the treatment of podocyte ER stress-induced hereditary or sporadic podocytopathies, including, but not limited to, hereditary NSs, FSGS, MN, MCD, Alport syndrome or diabetic nephropathy, which may share the common feature of having the "druggable" dysregulated RyR2 in podocytes.

Methods

Mice

Tg-WT, Tg-C321R and Lamb2$^{+/-}$ mice have all been described previously. All animal experiments conformed to the National Institutes of Health Guide for the Care and Use of Laboratory animals and were approved by the Washington University Animal Studies Committee.

Isolation of Mouse Glomeruli

Mice were perfused through the heart with magnetic 4.5 μm-diameter Dynabeads (Invitrogen, Carlsbad, Calif.). Kidneys were minced into small pieces, digested by collagenase A (Sigma-Aldrich, St. Louis, Mo.) and DNAse I (Sigma-Aldrich), filtered, and collected using a magnet. The purity of glomeruli was >95%.

Mouse Primary Podocyte Culture

Isolated glomeruli from Tg-WT, Tg-C321R, and Lamb2$^{+/-}$ mice at P27 were plated onto collagen type I-coated culture dishes, and cultured in 5% $CO_2$ at 37° C. in DMEM (Gibco, NY):Ham's F-12 (Lonza, NY) (2:1) that contained 3T3-L1 supernatant, 5% heat-inactivated fetal bovine serum (Gibco), 1% Insulin-Transferrin-Selenium liquid media supplement (Gibco), and 100 U/ml penicillin-streptomycin (Gibco). After 3 days, cell colonies began to sprout around the glomeruli. These cells (P0) showed an epithelial morphology with a polyhedral shape when confluence was reached. Passage 0 podocytes from the indicated genotypes were used for RNA sequencing, and passages 1 and 2 podocytes for other in vitro studies.

Antibodies and Reagents

Commercially available antibodies were obtained as follows: anti-caspase 12, anti-caspase 3, anti-p-JNK, anti-JNK, anti-p-eIF2α, anti-eIF2α, and anti-IRE1α antibodies were from Cell Signaling (Beverly, Mass.); anti-ATF6 and anti-p-IRE1α antibodies were from Novus Biological (Littleton, Colo.); anti-CHOP antibody was from Thermo Scientific; anti-XBP1s antibody was from BioLegend (San Diego, Calif.); anti-talin 1 and anti-spectrin alpha chain antibodies were from Millipore; anti-ATF4 antibody was from Santa Cruz Biotechnology (Santa Cruz, Calif.), anti-RyR and anti-phospho-RyR2 (S2808) antibodies were from Abcam (Cambridge, Mass.); horseradish peroxidase (HRP)-conjugated anti-β-actin antibody was from Sigma-Aldrich. HRP-conjugated anti-mouse and anti-rabbit secondary antibodies were from Santa Cruz Biotechnology. Rat collagen 1 was from Trevigen (Gaithersburg, Md.). Fluo-4 AM was purchased from Invitrogen, and probenecid was from Santa Cruz. Recombinant human MANF was from R&D Systems (Minneapolis, Minn.). K201 was produced by NIH/NCATS.

Western Blot Analysis

Mouse primary podocytes and isolated glomeruli were lysed by RIPA buffer (Cell signaling) containing protease inhibitor cocktail (Sigma-Aldrich) and phosphatase inhibitor tablets (Roche, Indianapolis, Ind.). The protein concentrations of cell and glomerular lysates were determined by Bio-Rad Protein assay (Hercules, Calif.) using BSA as a standard. Denatured proteins were separated on SDS-polyacrylamide gels and then transferred to polyvinylidene difluoride membranes (Thermo Scientific). The membranes were blocked with 5% non-fat milk for 1 h and then incubated overnight with primary antibodies. Following incubation, membranes were washed with 0.1% Tris-buffered saline/Tween buffer and incubated with the appropriate HRP-conjugated secondary antibodies. The proteins were then detected using ECLplus kit (GE, Pittsburgh, Pa.) and visualized in an x-ray developer. To ensure equal protein loading, the same blot was stripped with stripping buffer (25 mM glycine and 1% SDS, pH 2.0) and then incubated with an HRP-conjugated anti-mouse β-actin antibody. Protein band intensities were quantified using Image J software (NIH, Bethesda, Md.).

RNA Sequencing and Bioinformatics Analysis

RNA isolated from primary podocytes (P0) was purified using RNeasy Plus Mini Kit (Qiagen). RNA quality was assessed using a Bioanalyzer (Agilent Technologies) and only samples with RNA Integrity Numbers (RIN) above 9 were used for cDNA production. The library was prepared from RNA (30 ng) by using SMARTer® PCR cDNA synthesis kit (Clontech, Mountain View, Calif.). Single-end 50-bp sequencing was performed in an Illumina HiSeq3000, and the sequencing performance was assessed with RSeQC version 2.3. Reads were aligned to the Ensembl release 76 assembly with STAR version 2.0.4b. Gene counts were derived from the number of uniquely aligned unambiguous reads by Subread: feature Count version 1.4.5. All gene counts were then imported into the R/Bioconductor package EdgeR and trimmed mean of M values (TMM) normalization size factors were calculated to adjust for samples for differences in library size. The TMM size factors and the matrix of counts were then imported into R/Bioconductor package Limma to test for differential gene expression between Tg-WT (n=4) and Tg-C321R (n=3) mice. GSEA was used to test pathway enrichment for differentially expressed genes and the R/Bioconductor package Pathview was utilized to generate pathway maps on known signaling and metabolism pathways curated by KEGG.

Lentiviral Transduction of Primary Podocytes

The pLenti6.3 expression vectors encoding SERCaMP or GLuc-STOP have been described previously. The lentiviral vectors were packaged into virions in HEK 293T cells. In brief, 80% confluent HEK 293T cells were transfected with pLenti6.3-SERCaMP or pLenti6.3-GLuc-STOP and the two helper plasmids pMD2.G and psPAX2 (both from Addgene) in antibiotic-free DMEM with 10% FBS using Lipofectamine 2000 (Invitrogen), according to the manufacturer's protocol. After 18 hours, the medium was changed to DMEM with 10% FBS and penicillin-streptomycin. 24 to 48 hours thereafter, the virus-containing cell culture supernatant was harvested, centrifuged at 1000 rpm for 3 minutes, filtered through a 0.45 m filter (Millipore, Billerica, Mass.), and frozen at $-80°$ C. Primary podocytes from the respective mice at P27 were transduced with the lentiviruses, which were titered using the Lenti-X p24 rapid titer kit (Clontech) and used at a multiplicity of infection (MOI) of 5.

Luciferase Assay

Primary podocytes from Tg-WT, Tg-C321R and Lamb2$^{+/-}$ mice at P27 were cultured on collagen I-coated 12-well plates at $1.2 \times 10^4$ cells/well and transduced with lentiviruses expressing SERCaMP or GLuc-STOP for 8 hours. 48 hours thereafter, the Gluc activity in the media from the transduced podocytes was assayed by a BioLux Gaussia Luciferase Assay Kit (New England Biolabs, Ipswich, Mass.) according to the manufacturer's instructions and quantified with a Femtomaster FB12 Luminometer (Zylux, Oak Ridge, Tenn.). The actual values of raw light units were normalized with respect to total cell protein for each group.

Urinary calpain activity was measured by Calpain-Glo™ Protease Assay (Promega, Madison, Wis.). In brief, urines were incubated with calpain substrate (Succinyl-LLVY-aminoluciferin). Following cleavage of substrate by calpain, the substrate for luciferase (aminoluciferin) was released, allowing the luciferase reaction to occur and luminescence to be detected by Femtomaster FB12 Luminometer. The actual values of raw light units were normalized by urine Cr for each group.

Measurement of Cytosolic Calcium Levels

The cytosolic $Ca^{2+}$ levels were measured by Fluo-4 AM (Invitrogen). Primary podocytes of the indicated genotypes were plated on 6-well plates at $1 \times 10^5$ cells/well and stained with 2.5 µM Fluo-4 AM and 1 mM probenecid in the dark at 37° C. for 30 minutes. Then the cells were washed with PBS and kept in the dark for another 30 minutes to allow cleavage of intracellular AM esters. Fluorescence was measured by flow cytometer Calibur 3 (BD Biosciences, San Jose, Calif.) at the FACS core facility of Washington University School of Medicine. The results were analyzed by Cell Quest. For measuring intracellular $Ca^{2+}$ levels in primary podocytes treated with or without K201 or MANF, cells were plated on 96-well plates at $0.8 \times 10^4$ cells per well and stained with Fluo-4 AM along with probenecid to enable high-throughput readout. Fluorescence was measured at excitation wavelength 485 nm and emission wavelength 528 nm by a fluorescent plate reader Synergy H1 (BioTek, Winooski, Vt.).

Apoptosis Analysis in Primary Podocytes

Apoptotic cell death was measured by FITC Annexin V/PI apoptosis detection kit (BD Biosciences) according to the manufacturer's protocol. Primary podocytes from the indicate genotypes were plated on 6-cm dishes at $1.5 \times 10^5$ cells/dish in the absence or presence of K201 or MANF for 24 hours. The untreated- and treated-podocytes were harvested, washed with cold PBS twice, resuspended in binding buffer, and stained with Annexin V-FITC and PI in dark at room temperature for 15 minutes. After incubation, binding buffer was added, and the podocytes were analyzed by flow cytometer Calibur 3 (BD Biosciences). Unstained cells, cells stained with FITC-Annexin V or PI alone were used as controls to set up compensation and quadrants in flow cytometry. The results were analyzed by Cell Quest program.

BUN Measurement

BUN was measured by using a QuantiChrom™ urea assay kit (DIUR-500) (BioAssay Systems, Hayward, Calif.).

Urinalysis

Mouse urines were collected by manual restraint or using a metabolic cage. The mouse urines were centrifuged at 1800 g for 10 minutes to remove debris before being frozen at $-70°$ C. Urinary Cr concentration was quantified by a QuantiChrom™ creatinine assay kit (DICT-500) (BioAssay Systems) and albuminuria was measured by a QuantiChrom™ BCG albumin assay kit (DIAG-250) (BioAssay Systems).

Statistics

Statistical analyses were performed using GraphPad Prism 5 software (San Diego, Calif.). Data were expressed as mean±SD of three or more independent experiments. A 2-tailed Student's t test was used to compare 2 groups. One-way ANOVA with post-hoc Tukey test was used to compare multiple groups. P<0.05 was considered statistically significant. The statistical analysis for RNA sequencing was described above.

Light Microscopy

For light microscopy, kidneys were fixed in 4% paraformaldehyde, dehydrated through graded ethanols, embedded in paraffin, sectioned at 4 µm, and stained with Hematoxylin & Eosin (H&E) by standard methods.

Example 2: MANF Rescues Er-Stressed Podocytes in Nephrotic Syndrome

The following example describes how MANF rescues endoplasmic reticulum (ER)-stressed podocytes in nephrotic syndrome (NS). The ER plays an important role in the folding, assembly, and post-translational modification of secretory proteins. Disturbances to ER homeostasis cause accumulation of unfolded or misfolded protein in the ER lumen that results in ER stress. Emerging evidence has demonstrated that ER stress contributes to the development and progression of glomerular and tubular diseases.

ER stress activates cellular unfolded protein responses (UPR) to reduce ER stress, regulate ER homeostasis, and prevent cell death. The consequence of the UPR includes the following.

First, translational attenuation inhibits new protein synthesis and prevents further accumulation of unfolded proteins. Second, transcriptional induction of ER chaperones increases protein folding activity. Third, degradation of misfolded proteins in the ER, which is called ER-associated degradation (ERAD), is enhanced. Finally, apoptosis ensues when the ER function is severely impaired.

Pierson syndrome is an autosomal recessive disease characterized by severe congenital nephrotic syndrome and ocular and neurological abnormalities. It is caused by laminin β2 (LAMB2) mutations. LAMB2 is a component of the laminin α5β2γ1 trimer (see e.g., FIG. 19).

The laminin α5β2γ1 trimer is a major component of the mature glomerular basement membrane (GBM). Laminin trimerization occurs in the ER and then laminin is secreted into the extracellular space. Different LAMB2 deletions and missense mutations have been identified in Pierson syndrome. The C321R mutation is located in the LEa domain of LAMB2. This cysteine to arginine mutation disrupts disulfide bonding in the LEa domain, which could easily result in LAMB2 misfolding. The C321R mutation causes nephrotic syndrome.

Figure 20:
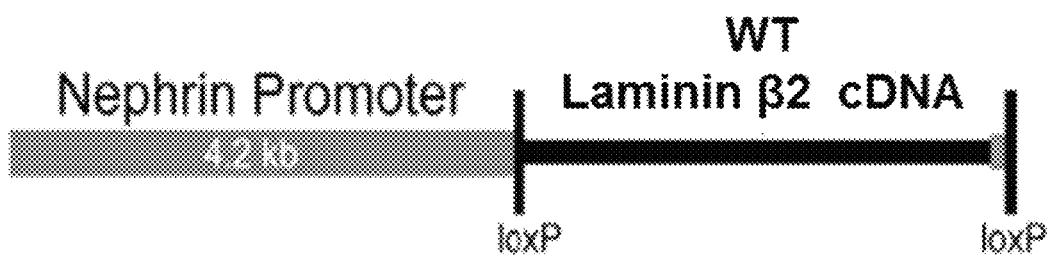
FIG. 20. Schematic of the genetic construct used to generate a podocyte-specific C321R-LAMB2 transgenic mouse on the Lamb2$^{-/-}$ background.
Figure 20:
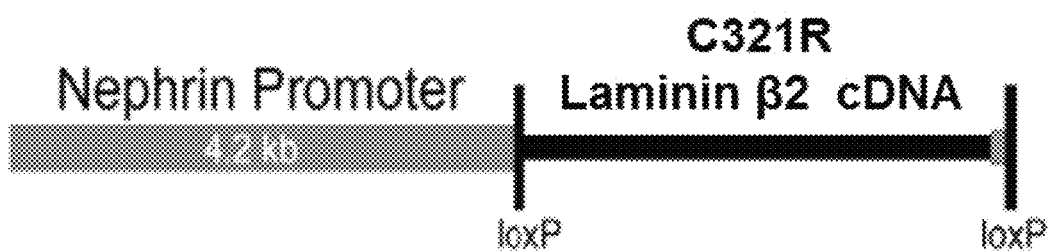
Figure 21A:
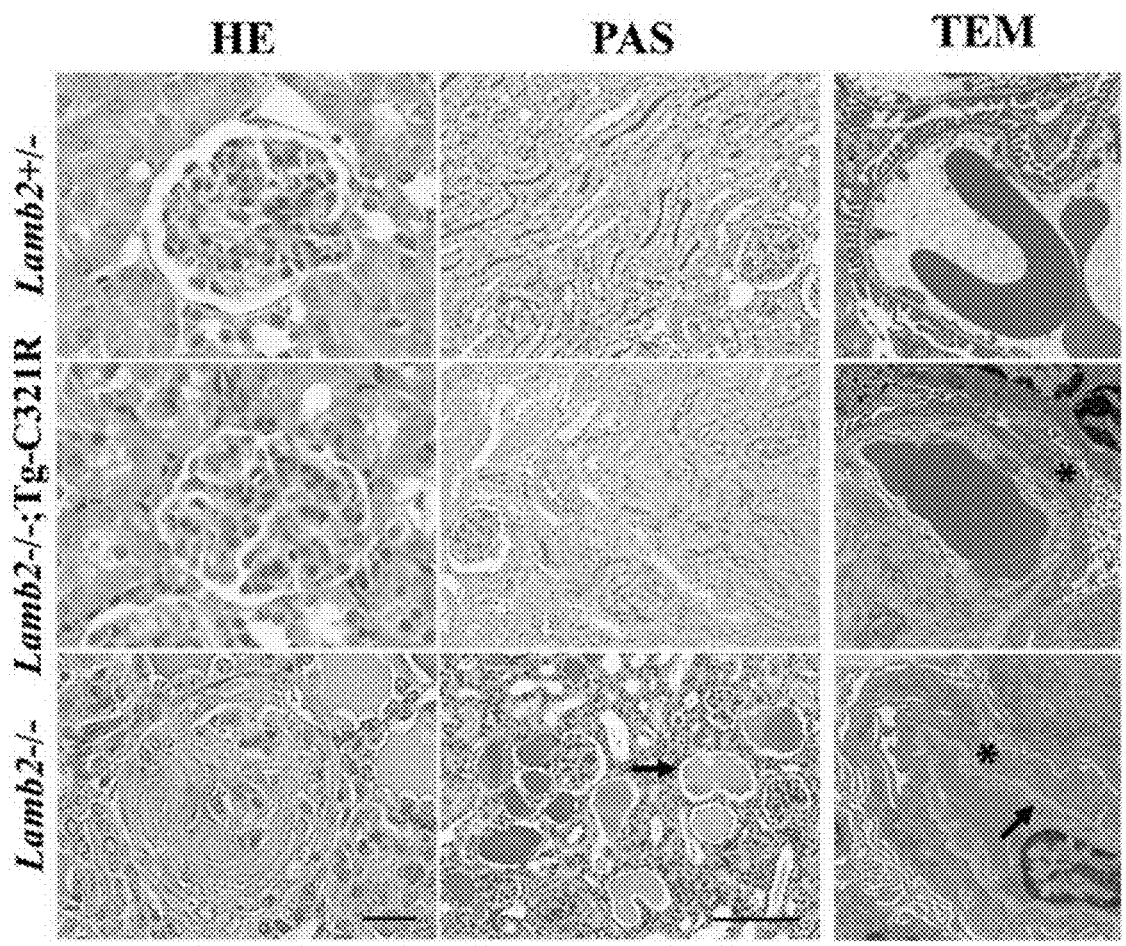
FIG. 21A-FIG. 21B. Renal histopathology shows glomerulosclerosis, glomerular basement membrane thickening, and interstitial fibrosis observed in Lamb2$^{-/-}$ is attenuated in Lamb2$^{-/-}$; Tg-C321R. (A) Hematoxylin and eosin (HE) and periodic acid-Schiff (PAS) stained kidney sections from Tg-WT, Tg-C321R and Lamb2$^{+/-}$ mice, as well as transmission electron microscopy (TEM) images at postnatal 24 days. (B) TEM images and Trichrome stained kidney sections from Tg-C321R and Lamb2$^{+/-}$ mice at 6 weeks of age.
Figure 21B:
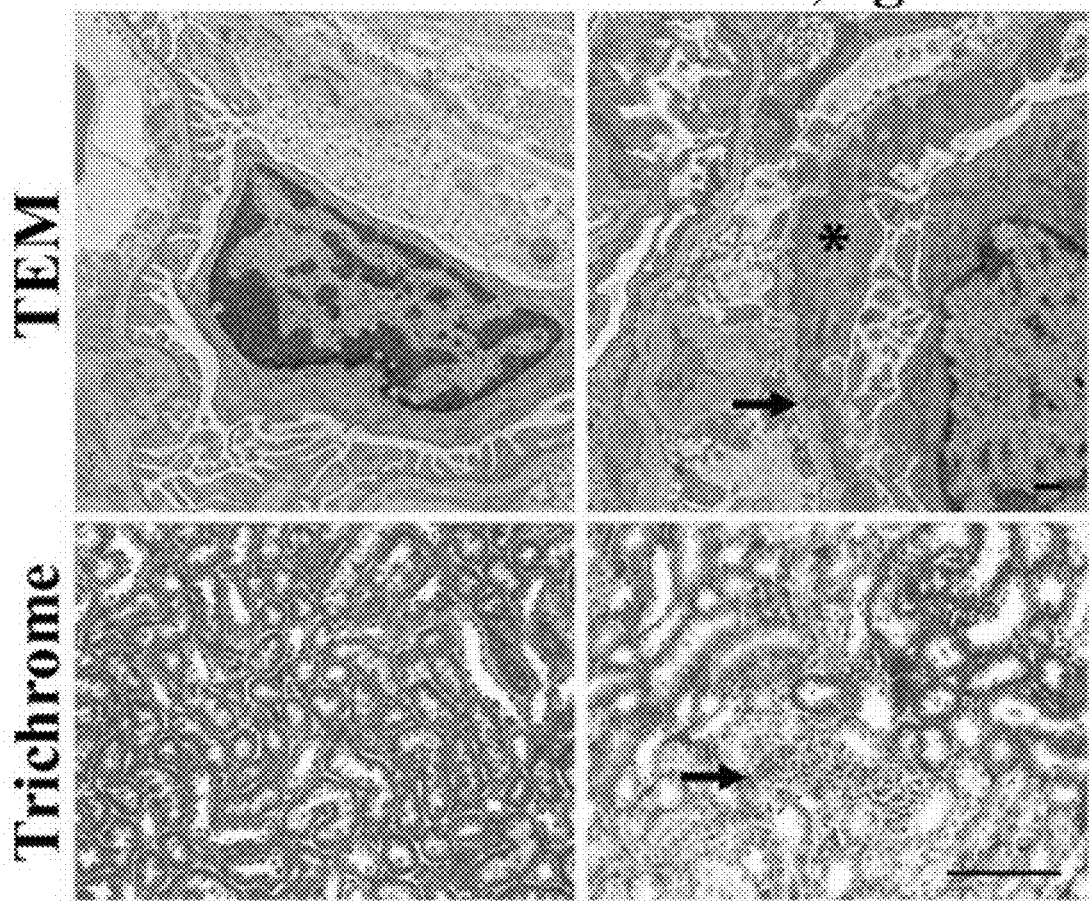

To investigate the mechanism by which the C321R-LAMB2 mutation causes nephrotic syndrome, a transgenic mouse model was created in which endogenous LAMB2 is replaced by mutant C321R-LAMB2 and is expressed specifically in podocytes (see e.g., FIG. 20). LAMB2 cDNA with the C321R mutation was inserted under the control of the podocyte-specific nephrin promoter. The C321R-LAMB2 transgene was then bred into the Lamb2$^{-/-}$ background (Lamb2$^{-/-}$; Tg-C321R or Tg-C321R, for short). A control transgenic mouse with wild-type LAMB2 expressed under the nephrin promoter in a Lamb2$^{-/-}$ background was also created (Lamb2$^{-/-}$; TG-WT or Tg-WT, for short).

In order to phenotype the Lamb2$^{-/-}$; Tg-C321R mice, the renal histopathology was examined and compared to wild-type (Lamb2$^{-/-}$) and Lamb2$^{-/-}$ mice (see e.g., FIG. 21A and FIG. 21B). By three weeks, Lamb2$^{-/-}$ mice developed mesangial expansion, glomerulosclerosis, and glomerular basement membrane (GBM) thickening, which was absent in the Lamb2$^{-/-}$; Tg-C321R mice (see e.g., FIG. 21A). PAS staining showed that Lamb2$^{-/-}$ mice exhibited abundant renal tubular protein casts and complete loss of brush borders in proximal tubules, which was not observed in the Lamb2$^{-/-}$; Tg-C321R mice. These findings suggest that transgene expression and the subsequent deposition of C321R-LAMB2 in the GBM partly ameliorate the severe defects of Lamb2$^{-/-}$ mice early in the disease. By six weeks, Trichrome staining showed that Lamb2$^{-/-}$; Tg-C321R mice had begun to develop interstitial fibrosis, which was absent in wild-type littermates (see e.g., FIG. 21B).

Missense mutations in LAMB2 may lead to protein misfolding, disruption of protein trafficking and ER retention. Protein folding in the ER occurs with the help of ER-resident molecular chaperones and enzymes, such as BiP. BiP is also a key sensor linked to the regulation of UPR.

Figure 14A:
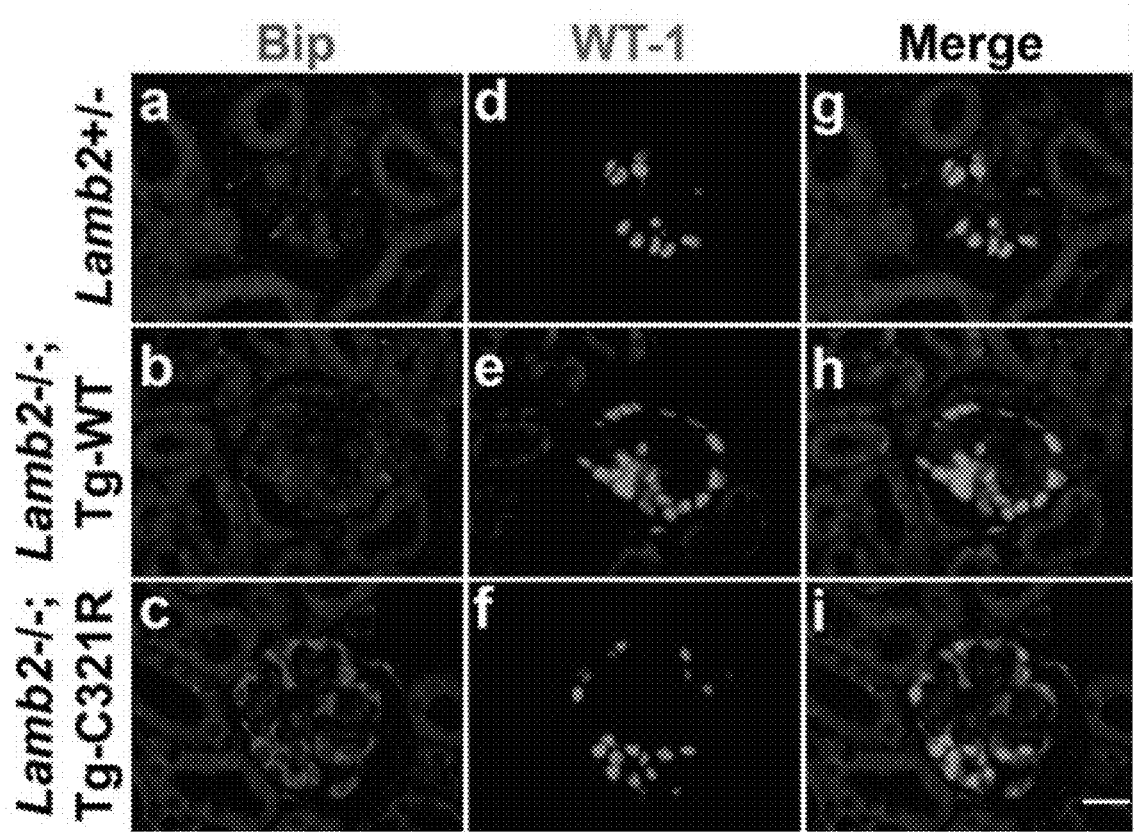
FIG. 14A-FIG. 14C. Podocyte ER stress is induced in Lamb2$^{-/-}$; Tg-C321R mice. (A) Dual immunofluorescence staining for immunoglobulin binding protein (BiP) and the podocyte nucleus marker WT-1 in frozen kidney sections from Tg-WT, Tg-C321R, and Lamb2$^{+/-}$ mice. Western blot analysis of BiP expression in (B) glomerular lysates and (C) primary podocytes from mice of the indicated genotypes at P25.
Figure 14B:
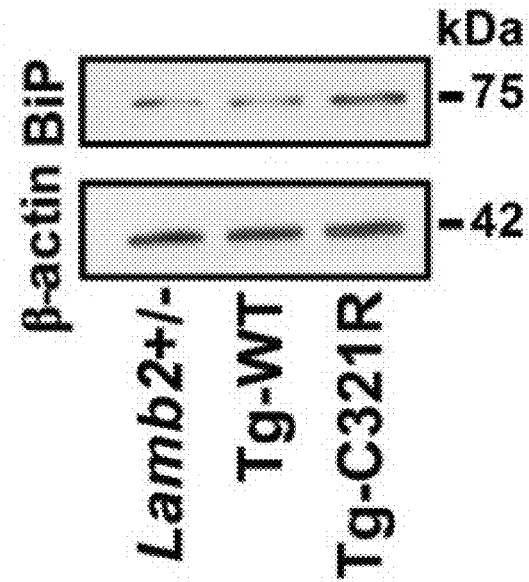
Figure 14C:
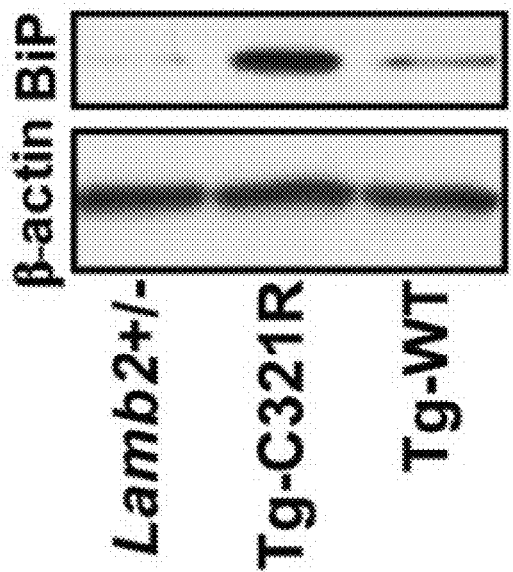
Figure 15A:
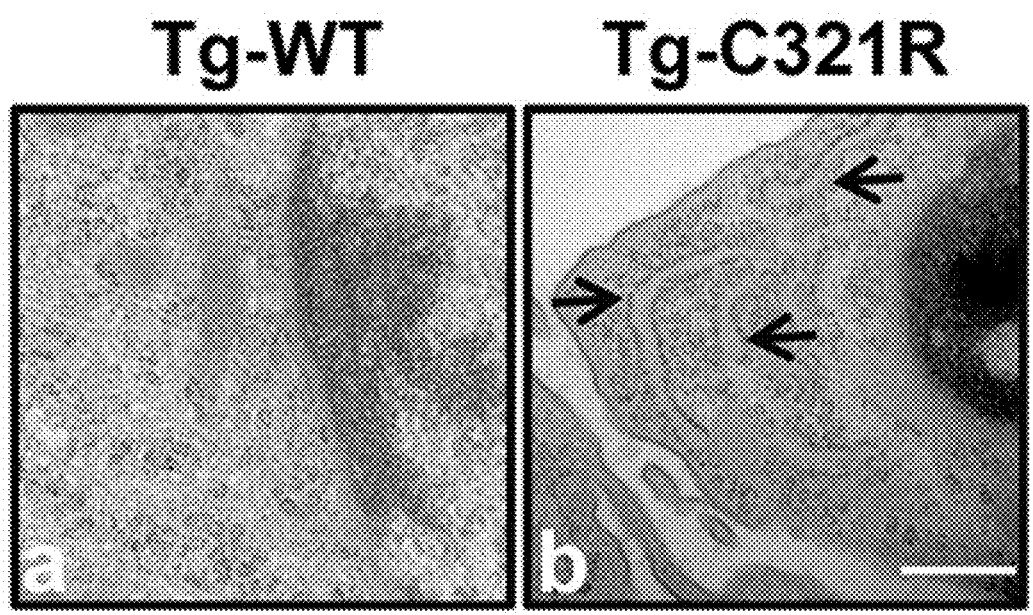
FIG. 15A-FIG. 15B. Podocyte ER stress causes ER distension and podocyte injury. (A) Transmission electron microscopy image of ER in podocytes from Tg-WT and Tg-C321R mice. Arrows indicate abnormal swelling or vesicle formation. (B) Dual immunofluorescence staining for podocin and desmin expression in podocytes from Tg-WT, Tg-C321R and Lamb2$^{-/-}$ mice.
Figure 15B:
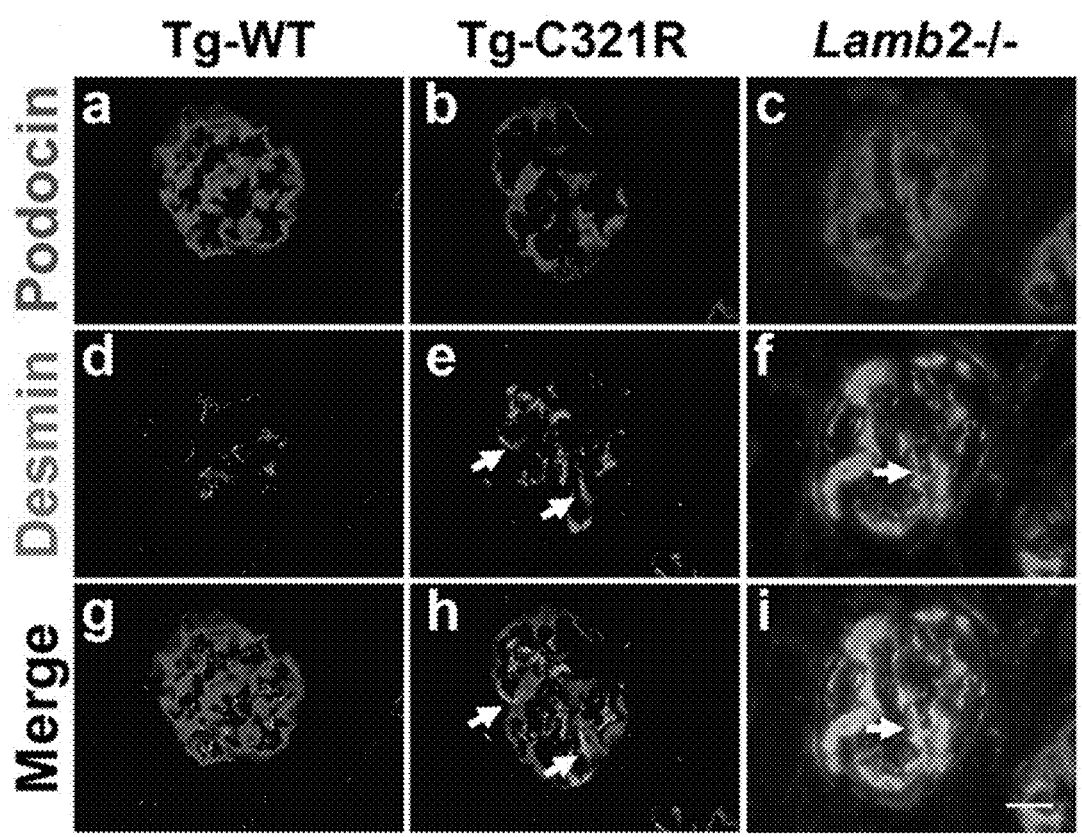

It was reported that the C321R mutation induces BiP upregulation in the mutant podocytes at 3 weeks of age, as demonstrated by double immunofluorescence staining of BiP and the podocyte nucleus marker WT-1 (see e.g., FIG. 14A), as well as a Western blot of isolated glomeruli (see e.g., FIG. 14B) and primary podocytes (see e.g., FIG. 14C).

Under ER stress conditions, there are three pathways that induce the adaptive UPR. Activated PERK leads to eIF2α phosphorylation. Active eIF2α inhibits general protein translation and induces ATF4. ATF4 induces the expression of ER chaperones. ATF6 translocates into the cis-Golgi compartment, where it is cleaved. The active form of ATF6 (p50ATF6) acts as a transcription factor and leads to induction of ER chaperones. Active IRE1 induces the splicing XBP1 mRNA. Spliced XBP1 mRNA encodes an active transcription factor XBP1s that upregulates ERAD components and ER chaperones.

Figure 1B:
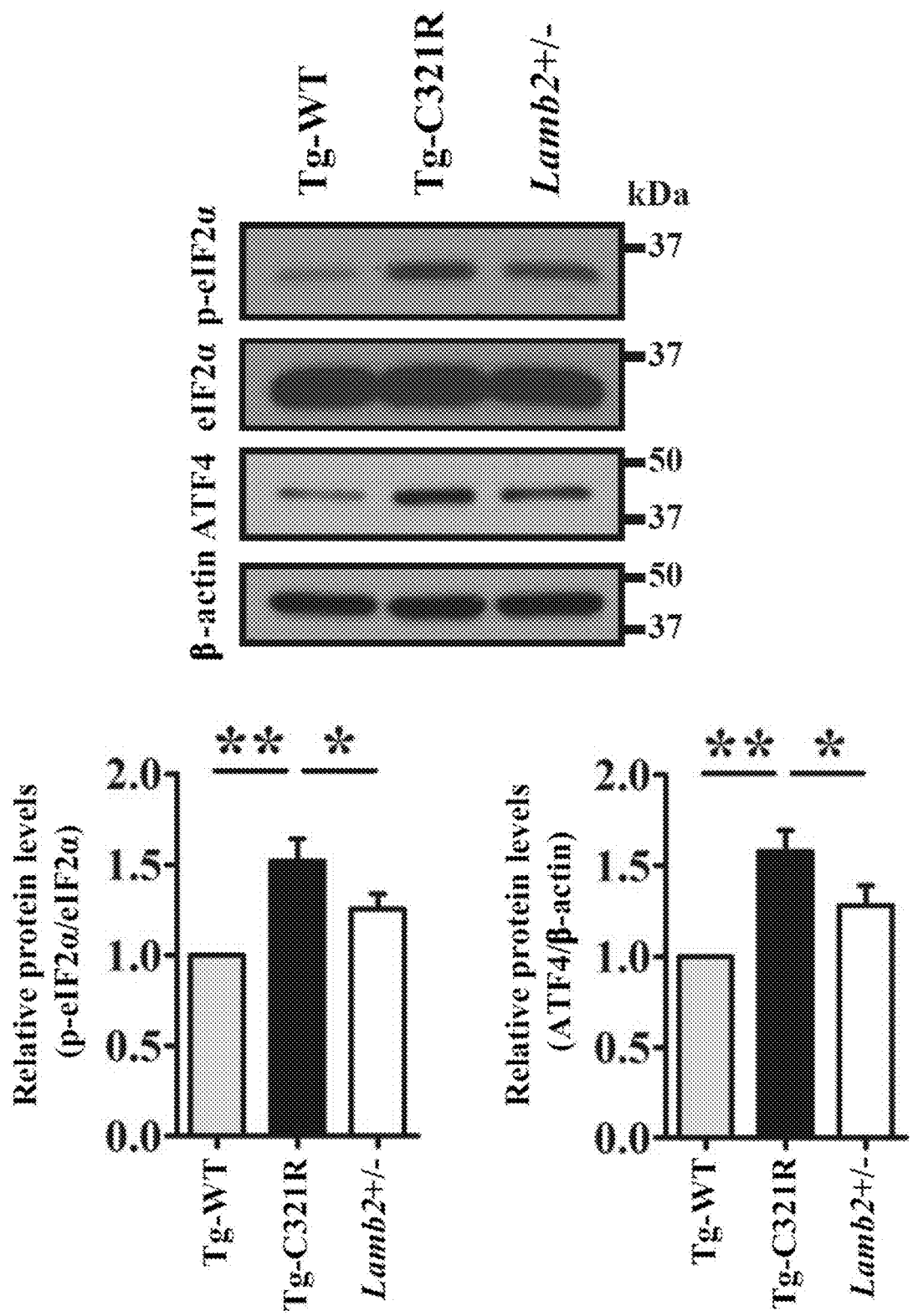
Figure 1C:
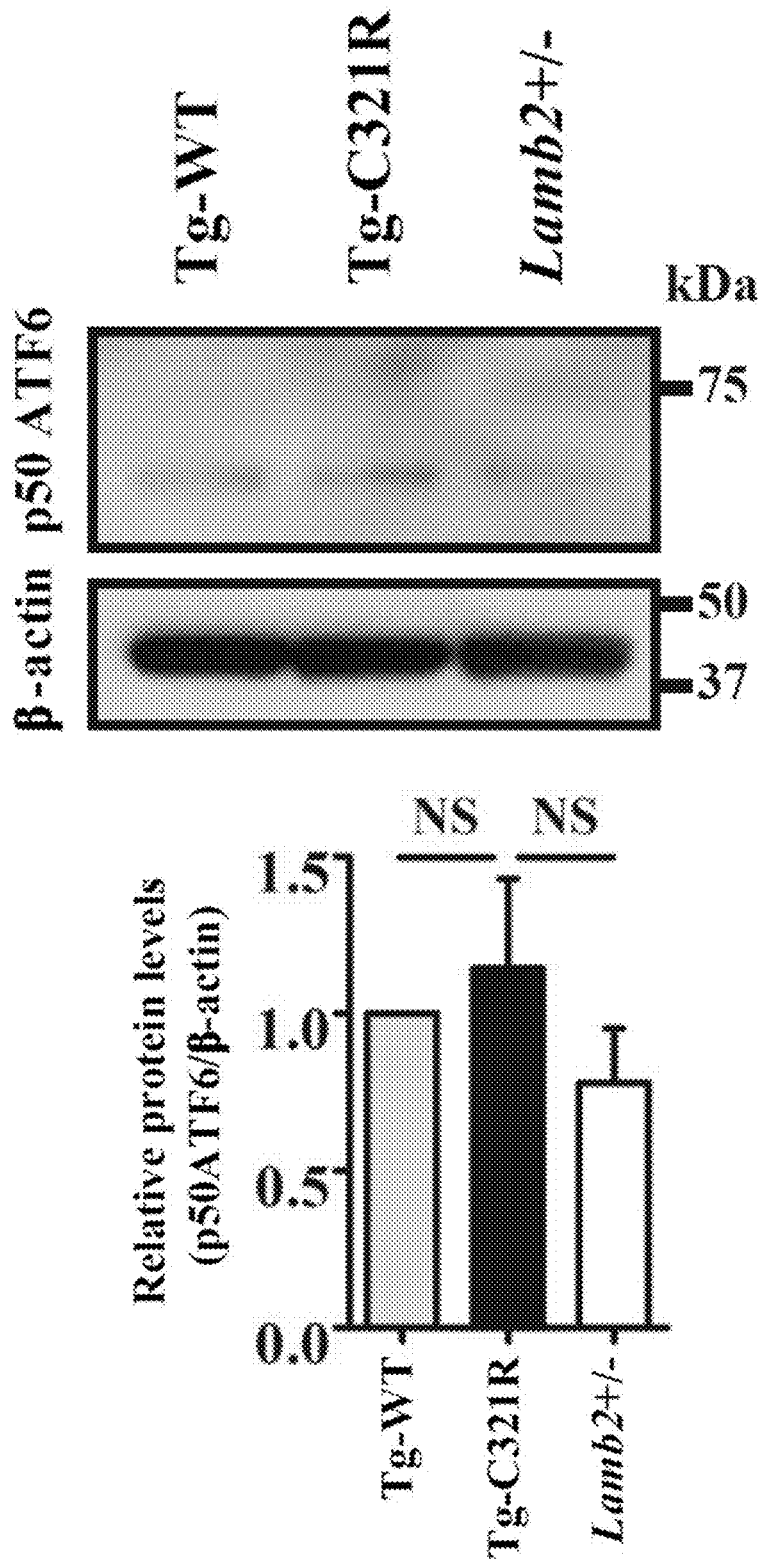

Investigation of the Signaling Pathways of C321R Mutation-Induced Podocyte ER Stress First, protein expression levels of the adaptive UPR signaling pathway in Tg-C321R podocytes were examined at P27 (see e.g., FIG. 1). Expression of p-IRE1α and splicing XBP1 was significantly increased in mutant podocytes compared to Tg-WT podocytes (see e.g., FIG. 1A). The levels of P-eIF2α and ATF4 were also higher in Tg-C321R podocytes than in Tg-WT podocytes (see e.g., FIG. 1B). However, there was no significant difference in p50ATF6 expression between Tg-WT and Tg-C321R genotypes (see e.g., FIG. 1C).

These results indicate that podocyte ER stress induced by C321R-LAMB2 activates the IRE1α/XBP1 pathway and eIF2α/ATF4 pathway. Severe ER stress causes ER dysfunction and morphological changes, leading to apoptosis. TEM data showed significant podocyte rough ER distention in Tg-C321R mice compared with Tg-WT mice (see e.g., FIG. 15A). Immunostaining also showed increased desmin expression, an indicator of podocyte injury, in Tg-C321R mice compared to Tg-WT mice (see e.g., FIG. 15B).

Figure 16B:
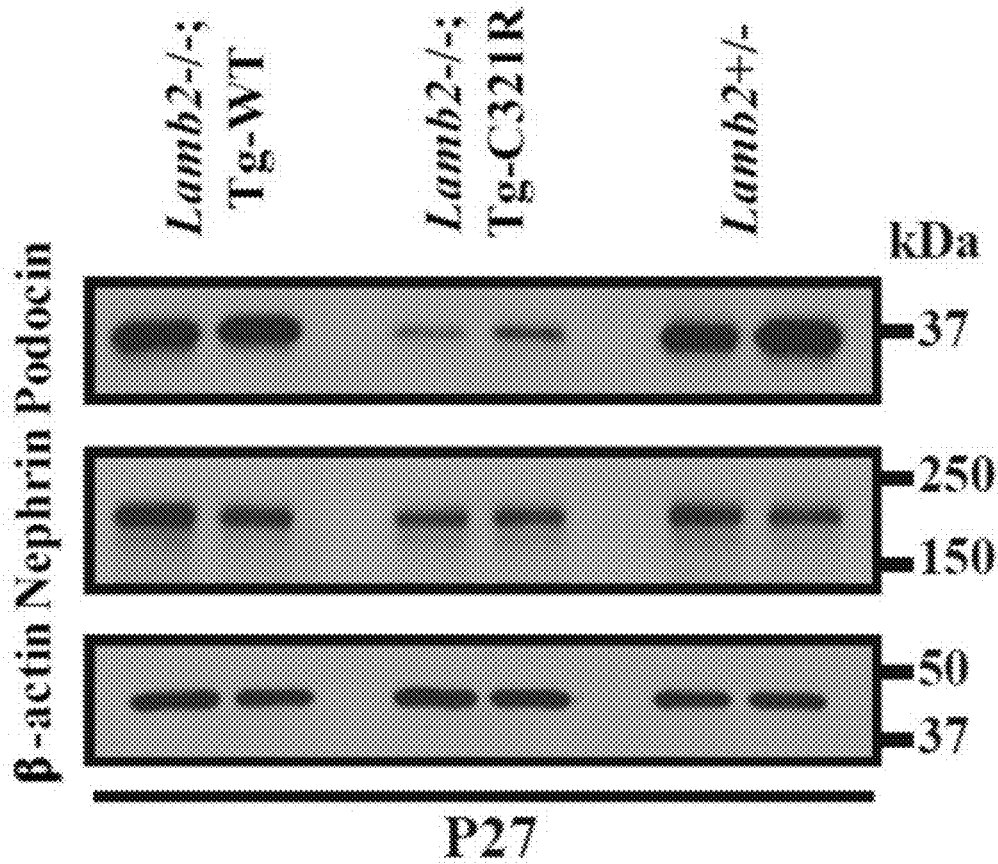
Figure 16C:
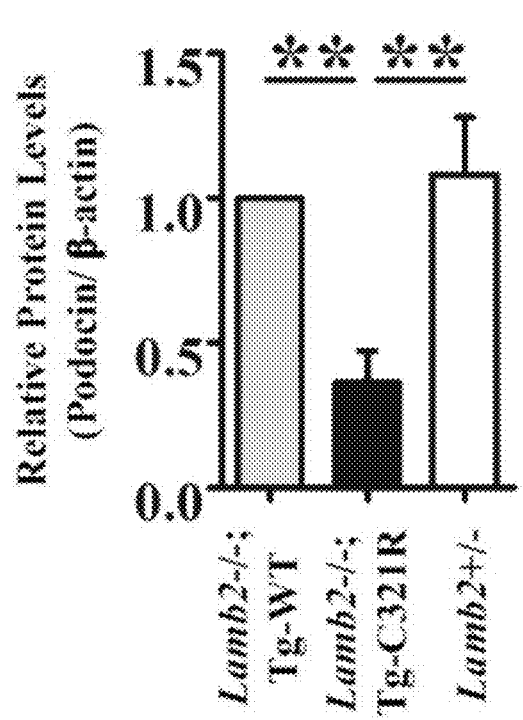
Figure 16C:
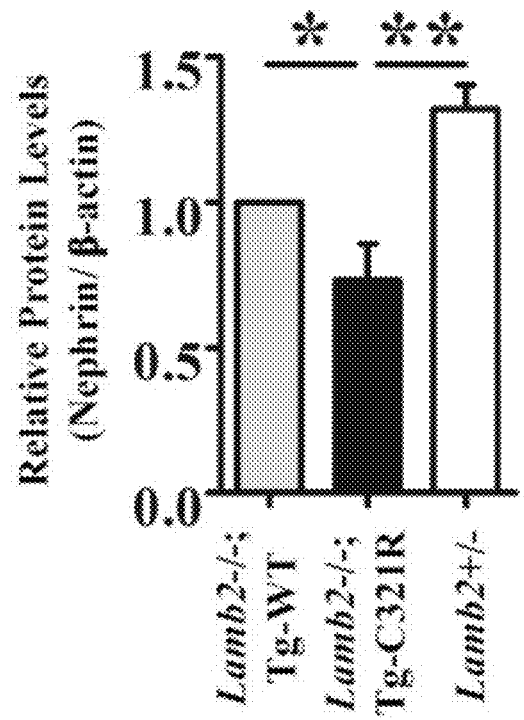
Figure 16D:
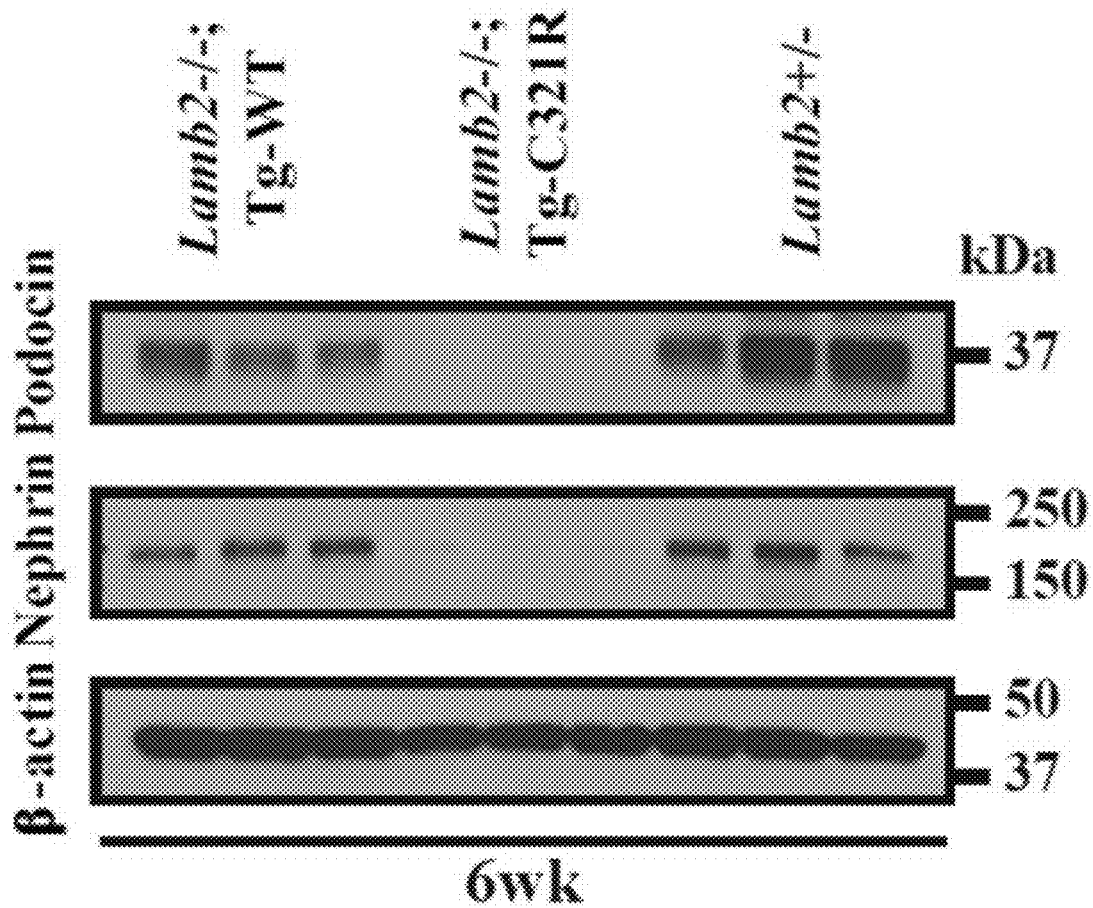

The expression levels of podocin and nephrin, proteins that are important for maintaining the slit diaphragm (SD) of podocytes, were also investigated in primary podocytes and glomeruli at P27. It was found that podocin and nephrin were significantly decreased in Tg-C321R podocytes compared to Tg-WT podocytes (see e.g., FIG. 16A and FIG. 16B). Both podocin and nephrin expression were also significantly decreased in Tg-C321R glomeruli compared to WT and Tg-WT glomeruli (see e.g., FIG. 16C). Podocin and nephrin expression in glomeruli isolated from 6 wk mice was also examined. Podocin and nephrin expression was further decreased in 6 wk Tg-C321R glomeruli compared to WT and Tg-WT glomeruli (see e.g., FIG. 16D). These results indicate that nephrin and podocin expression is downregulated in TG-C321R podocytes.

Figure 17A:
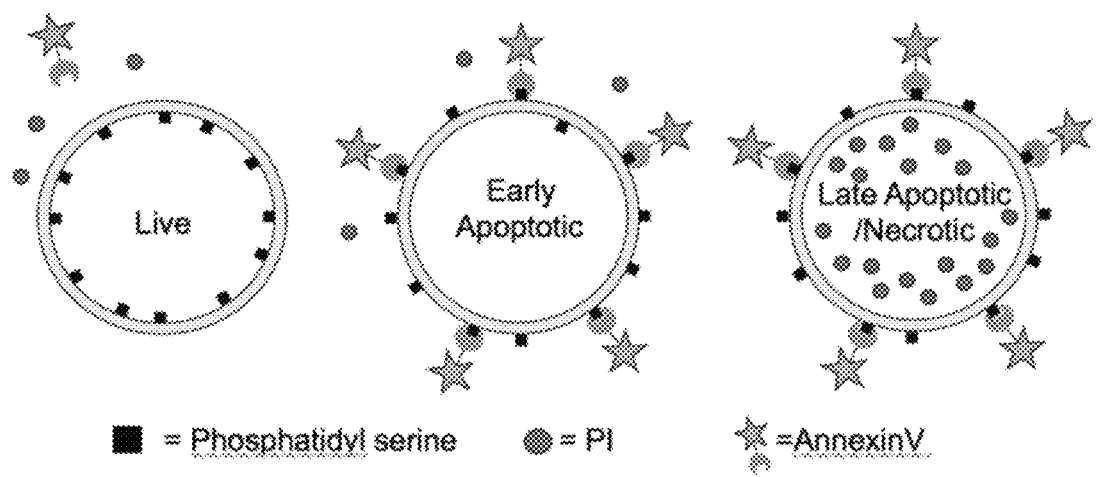
FIG. 17A-FIG. 17C. Apoptosis is increased in Tg-C321R podocytes. (A) Schematic of Annexin V and PI dyes binding to early apoptotic and late apoptotic cells, respectively. (B) Flow cytometry detection and (C) analysis of podocytes from Tg-WT, Tg-C321R and Lamb2$^{+/-}$ mice undergoing early apoptosis (Annexin V$^+$/PI$^-$ cells).

Because it was necessary to directly detect apoptosis in podocytes undergoing ER stress, Annexin V and propidium iodide (PI) were used to measure apoptosis in a cell population. Cells in early apoptosis bind Annexin V but not PI, while cells in late apoptosis bind to both Annexin V and PI (see e.g., FIG. 17A).

Figure 17B:
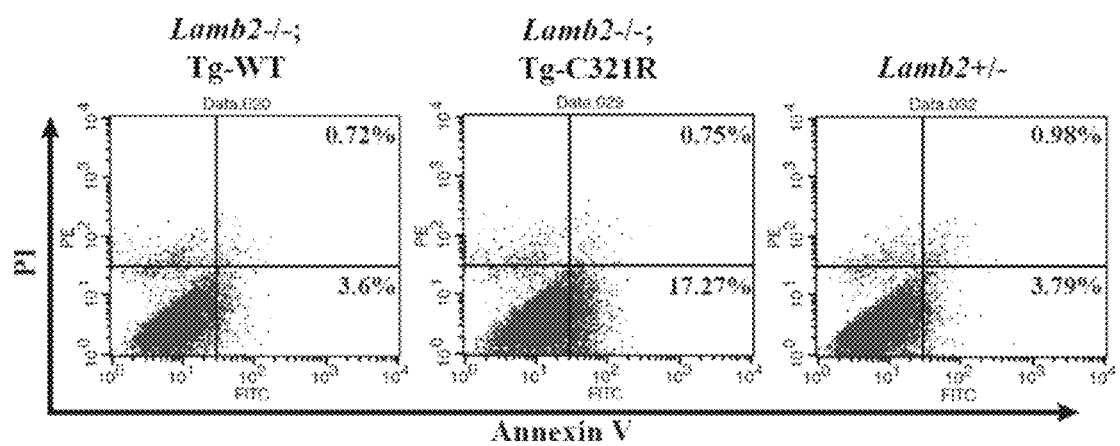
Figure 17C:
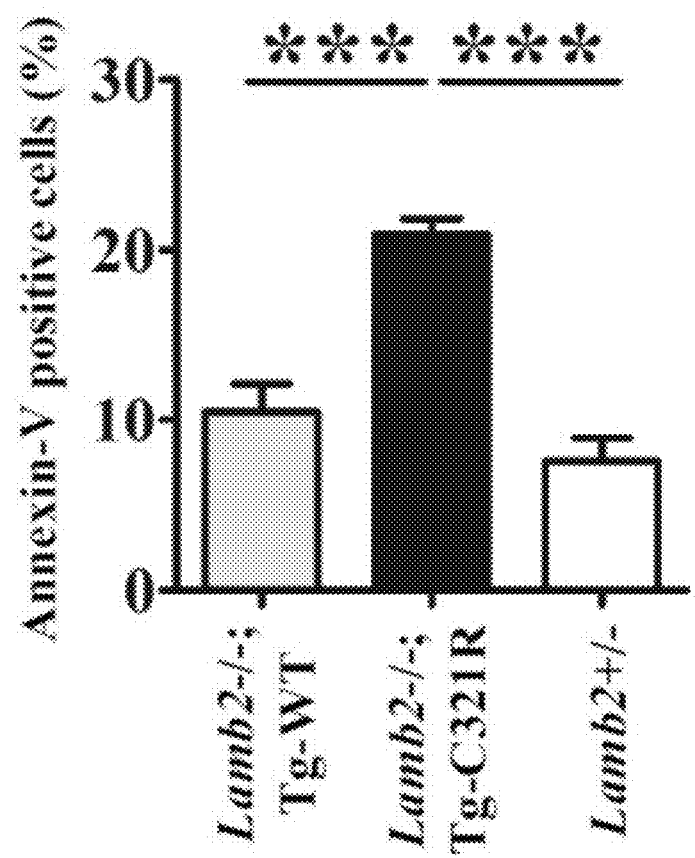
Figure 18A:
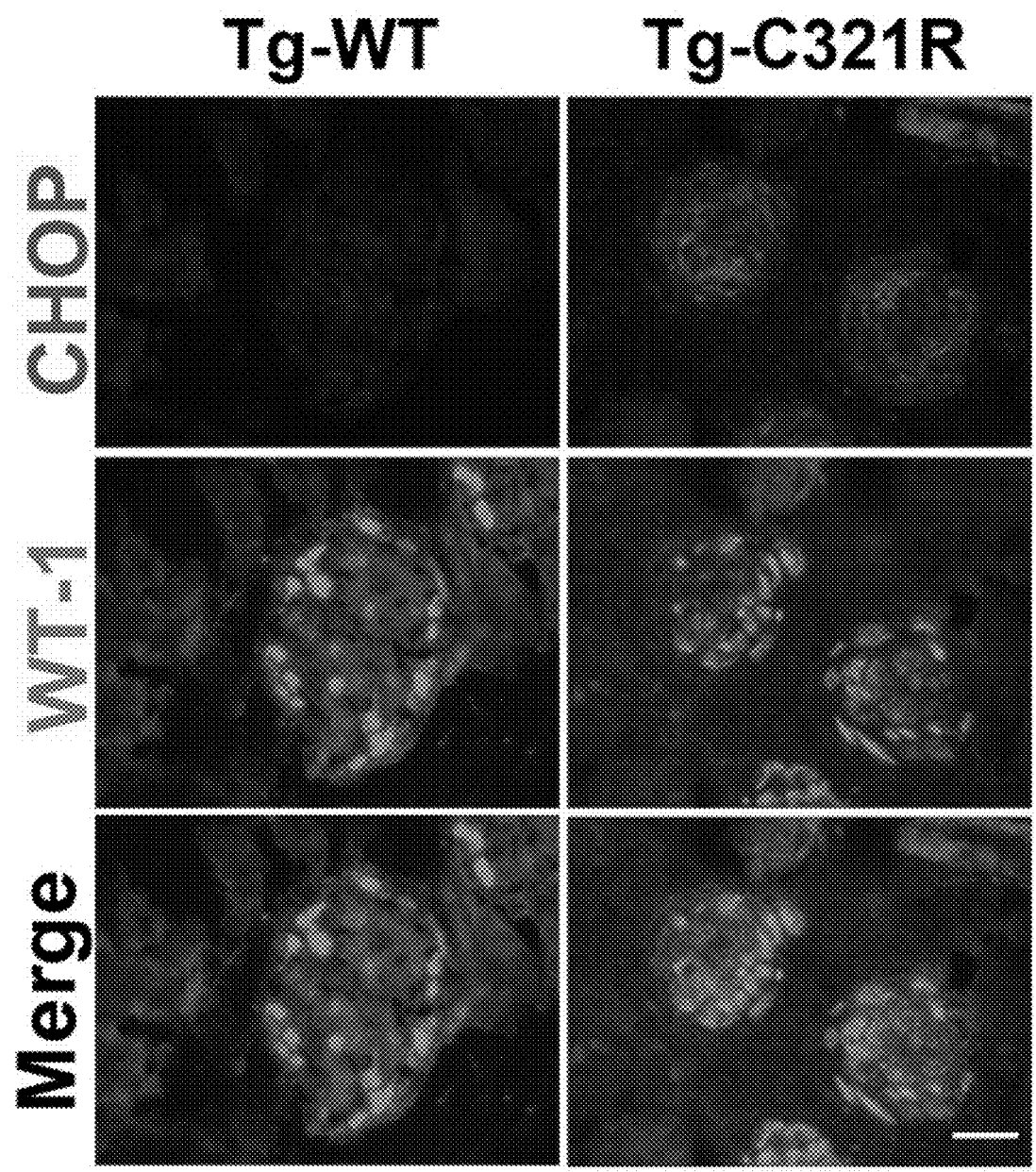
FIG. 18A-FIG. 18C. Podocyte ER stress induces CHOP activation. (A) Dual immunofluorescence staining for CHOP and the podocyte nucleus marker WT-1 on frozen kidney sections from Tg-WT and Tg-C321R mice. Western blot analysis of CHOP expression in (B) glomerular lysates and (C) primary podocytes from Tg-WT, Tg-C321R and Lamb2$^{+/-}$ mice.
Figure 18B:
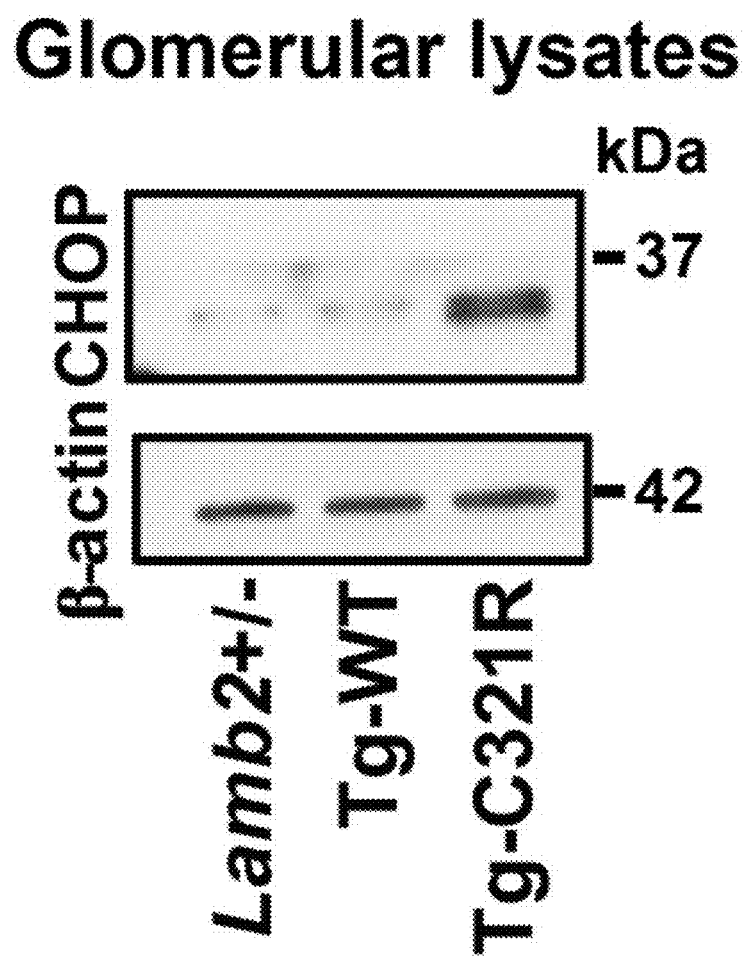
Figure 18C:
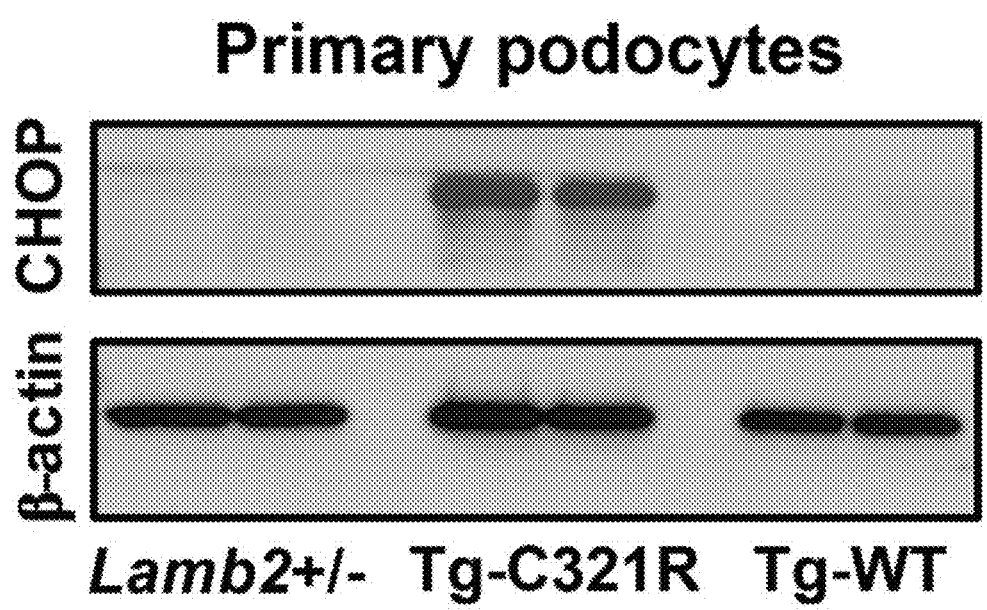

It was observed that the number of Annexin V positive/PI negative apoptotic cells was significantly increased in Tg-C321R podocytes compared with WT and Tg-WT podocytes (see e.g., FIG. 17B and FIG. 17C).

Excessive or prolonged ER stress can result in apoptotic cell death through the activation of the pro-apoptotic UPR pathway. Pro-apoptotic UPR is mediated by CHOP, JNK, and caspase 12 through the three UPR pathways that impair ER function and promote apoptosis.

In the pro-apoptotic UPR signaling pathway, CHOP (see e.g., FIG. 18A and FIG. 18C) and cleaved caspase 12 expression (see e.g., FIG. 2B) was significantly increased in Tg-C321R podocytes compare with WT and Tg-WT podocytes. Cleaved caspase 3 expression was also increased in Tg-C321R podocytes (see e.g., FIG. 2C).

Figure 9A:
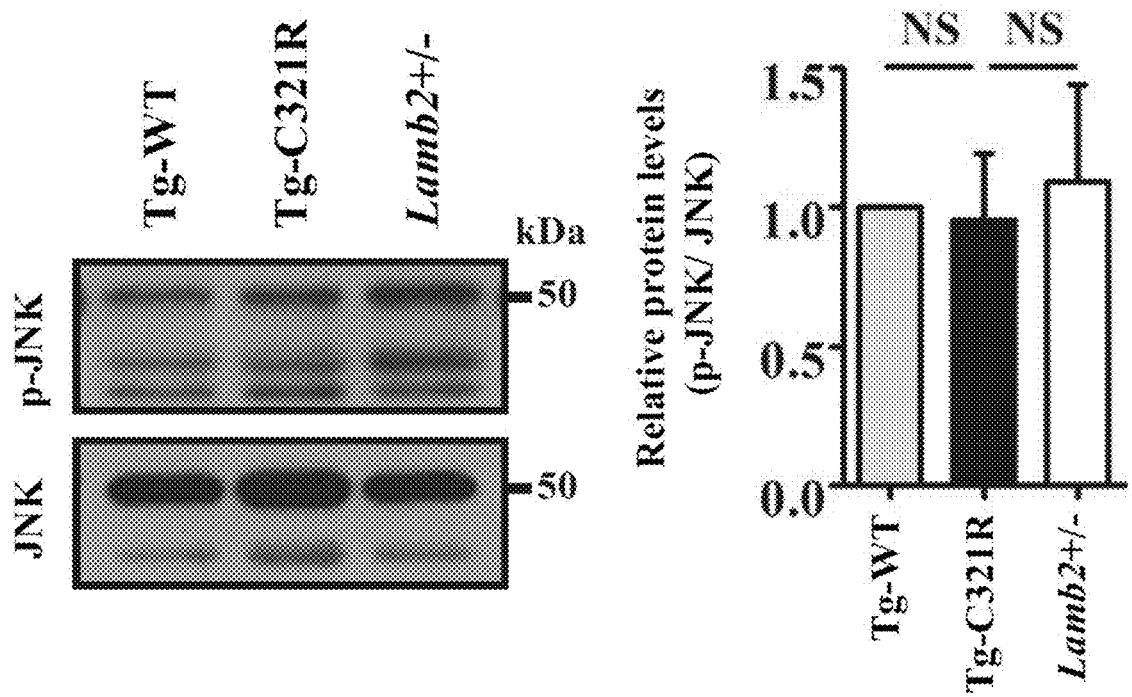
FIG. 9A-FIG. 9B. The JNK pathway is not involved in ER stress-induced apoptosis in Tg-C321R podocytes and glomeruli. Primary podocyte lysates (A) and glomerular lysates (B) from Tg-WT, Tg-C321R and Lamb2$^{+/-}$ mice at P27 were analyzed by Western blot with the indicated antibodies. Ratio of p-JNK to total JNK was quantified by densitometric analysis of 5 independent experiments. Mean±SD; NS: not significant by ANOVA.
Figure 9B:
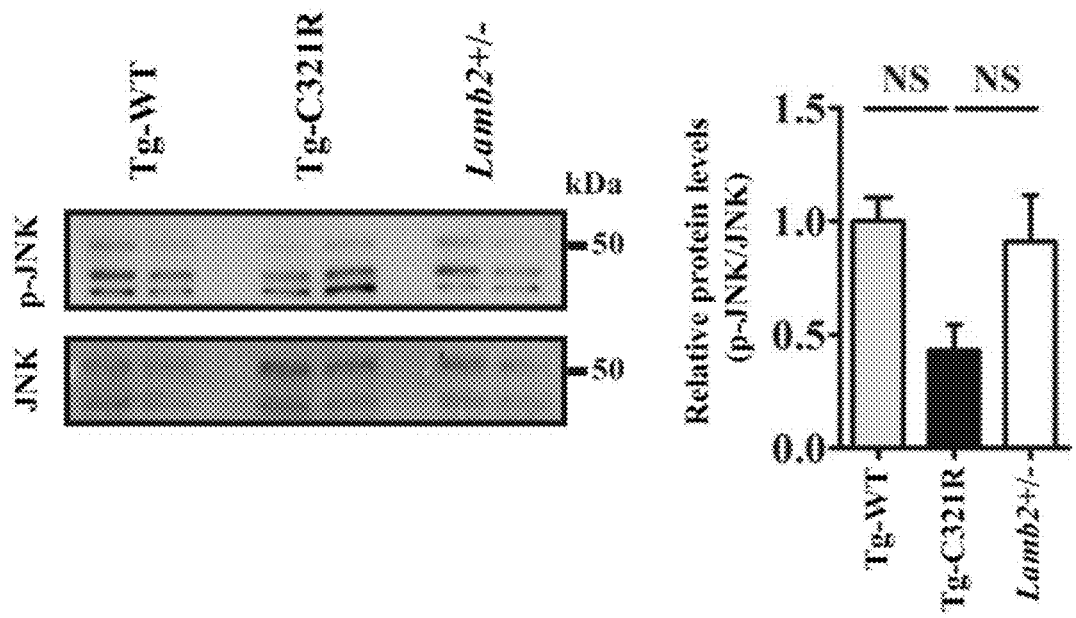

However, expression of p-JNK was not significantly different between Tg-WT and Tg-C321R podocytes (see e.g., FIG. 9A). It was shown that the C321R mutation activates caspase 12 and the CHOP apoptotic pathways.

Next, the involved apoptotic pathways were investigated using isolated glomeruli. Cleaved caspase 12 (see e.g., FIG. 2D) and CHOP expression (see e.g., FIG. 18A and FIG. 18B) were significantly increased in Tg-C321R glomeruli. Cleaved caspase 3 expression was slightly increased in Tg-C321R glomeruli (see e.g., FIG. 2D). However, there was no significant difference in p-JNK expression between Tg-WT and Tg-C321R glomeruli (see e.g., FIG. 9B).

These expression patterns are consistent with primary podocyte results. Therefore, the C321R-LAMB2 mutant leads to ER stress-mediated apoptosis via caspase 12 and CHOP pathway in the podocytes.

Intracellular Ca$^{2+}$ is mainly stored in the ER lumen. There are three receptors that regulate Ca$^{2+}$ homeostasis. SERCA induces calcium uptake into the ER. RYR and IP3R induce ER calcium release into the cytosol. Oligomerization of Bax/Bak promotes $Ca^{2+}$ release from ER into cytosol through IP3R and RYR. An increased level of intracellular $Ca^{2+}$ activates the calpain/caspase 12 pathway.

Prolonged ER stress leads to $Ca^{2+}$ release from the ER into cytosol through Bax/Bak, IP3R, and RYR. It activates calpain, which cleaves procaspase 12. Activated caspase 12 then initiates a caspase cascade and causes consequent apoptosis. Thus, activation of caspase 12 pathway is induced by ER $Ca^{2+}$ release and calpain activation.

For measuring cytosol calcium levels, a high affinity calcium indicator fluo-4 was used. Cytosolic calcium levels of mouse primary podocytes were measured using FACS and microplate reader. Cytosolic calcium levels were significantly increased in Tg-C321R podocytes compare to WT and Tg-WT podocytes (see e.g., FIG. 3D). The consistent results from both FACS and Microplate reader ensure the validity of the result.

Calpain activation was also evaluated. Measuring spectrin cleavage is a well-known method for detecting calpain activation. Spectrin is a cytoskeletal protein and is localized at the cytosolic site of the plasma membrane, and it plays crucial roles in cell proliferation and attachment. Spectrin is irreversibly cleaved by calpain, and is then degraded, leading to destruction of the cytoskeleton and cell death.

To further investigate calpain activation, talin 1 cleavage was also evaluated. Talin 1 is a key integrin and actin-binding protein, and it is also cleaved by calpain.

As described herein, the podocyte calpain-mediated talin 1 cleavage plays a vital role in the pathogenesis of nephrotic syndrome. To investigate calpain activation, spectrin and talin 1 cleavage were measured in podocyte lysates from Tg-WT and Tg-C321R mice. As shown here, cleaved spectrin and talin 1 expression was significantly increased in Tg-C321R mice (see e.g., FIG. 3A, FIG. 3B). It was also noted that caspase 12 activation was increased in Tg-C321R mice compared to Tg-WT (see e.g., FIG. 2B, FIG. 2D). Therefore, these results indicate that podocyte ER stress induced by the C321R-LAMB2 mutation activates calpain 2-caspase 12 proapoptotic pathway.

To confirm that the calcium overload detected in the cytosol is from the ER leakage, a Gluc-based secreted ER calcium-monitoring proteins (SERCaMPs) system was used. This system can be used to monitor ER calcium homeostasis. In normal conditions, SERCaMP is localized in the ER and secreted in response to ER calcium depletion condition.

Figure 4D:
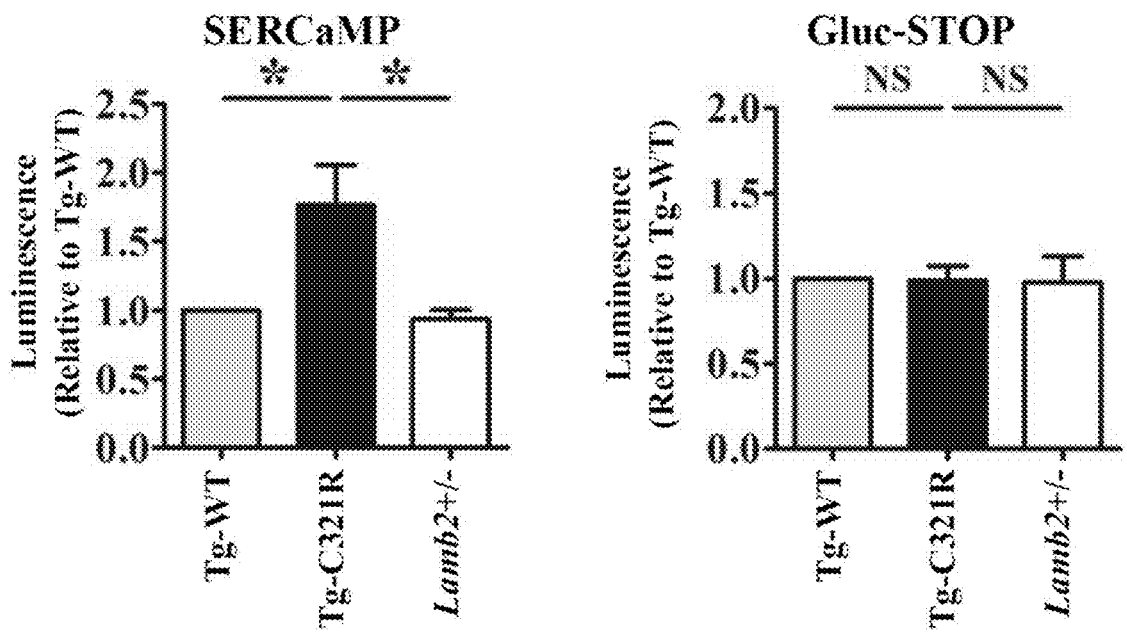

It was found that the secreted SERCaMP was increased in Tg-C321R podocytes compared with Tg-WT and WT podocytes (see e.g., FIG. 4D).

Figure 5B:
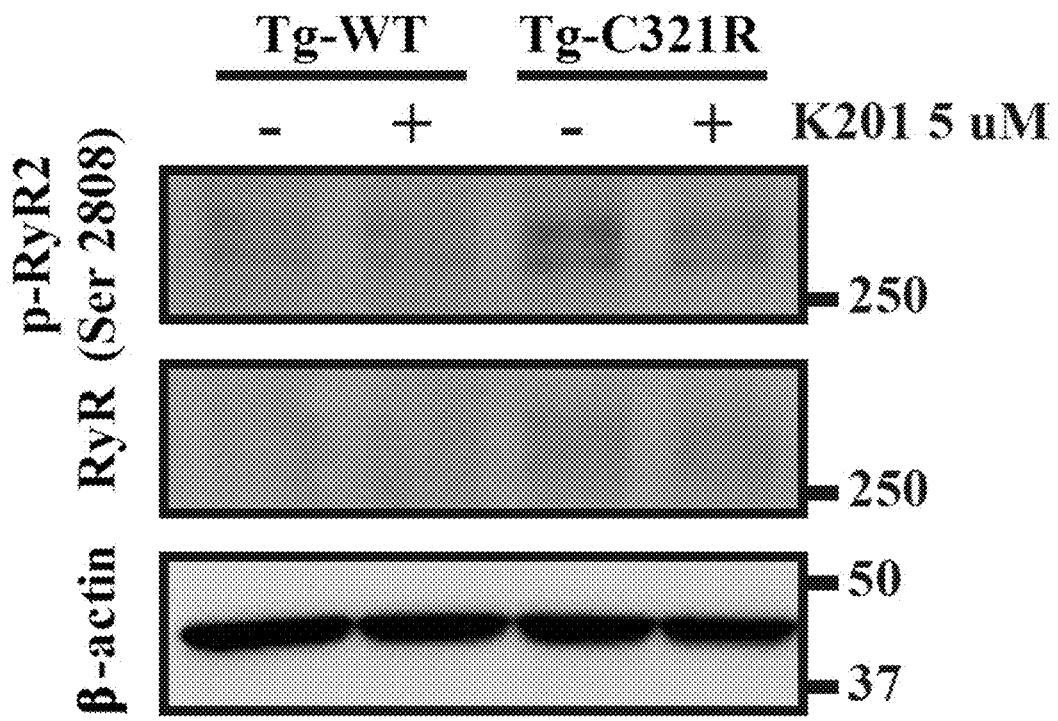
Figure 5C:
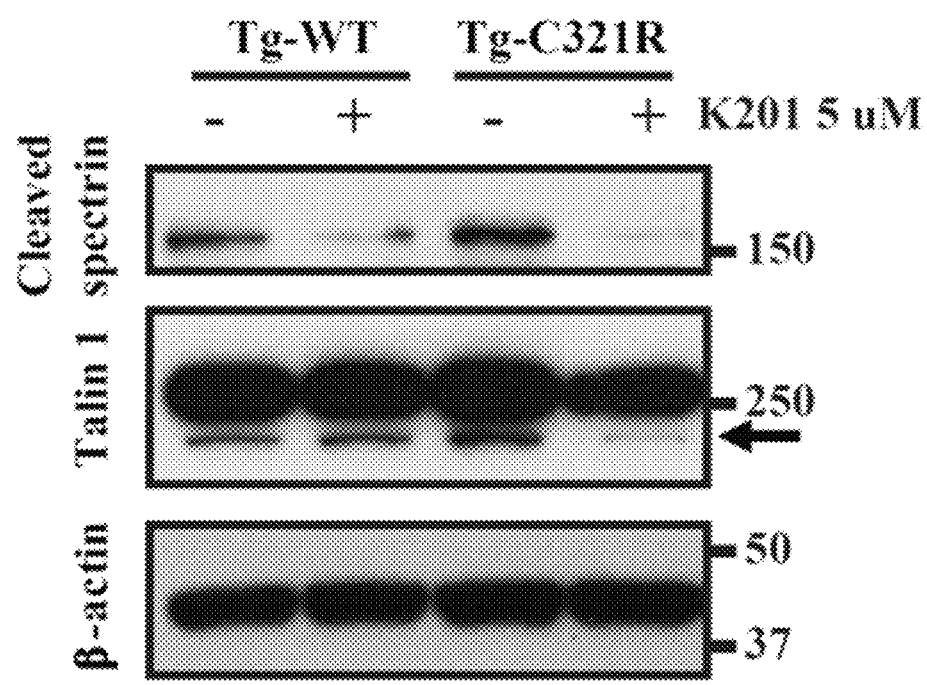
Figure 5D:
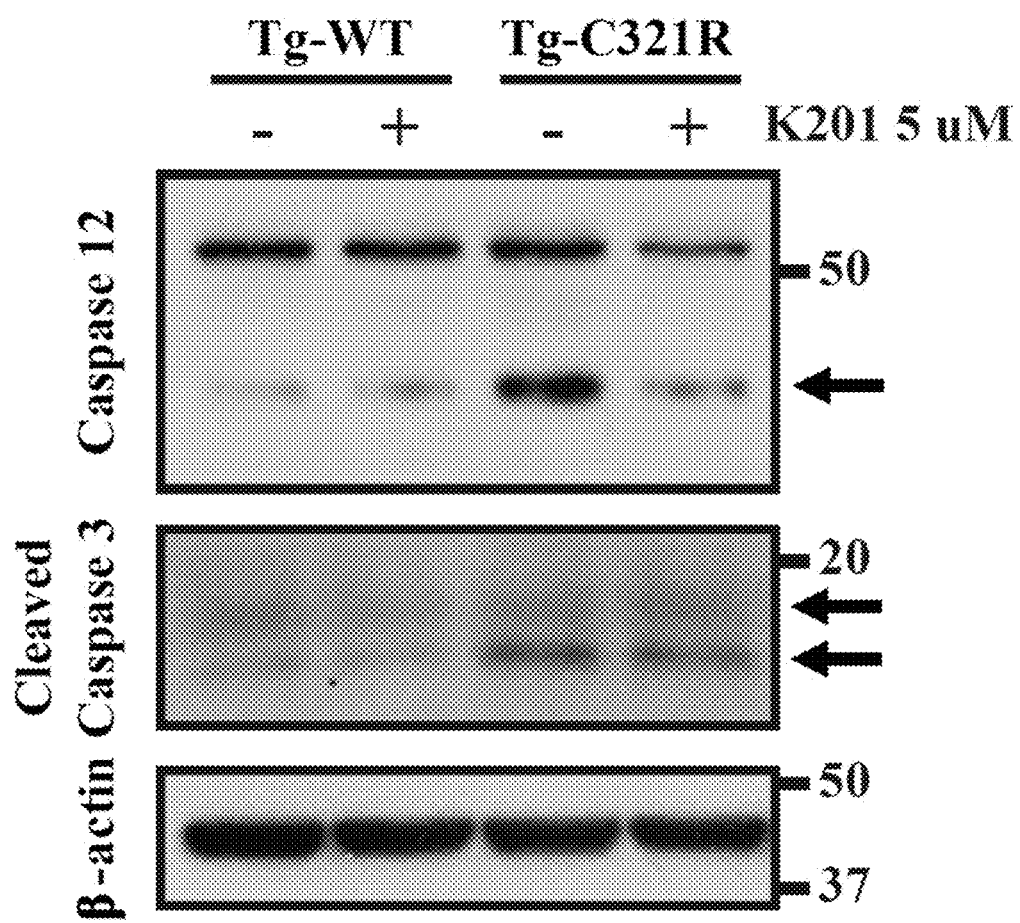
Figure 5E:
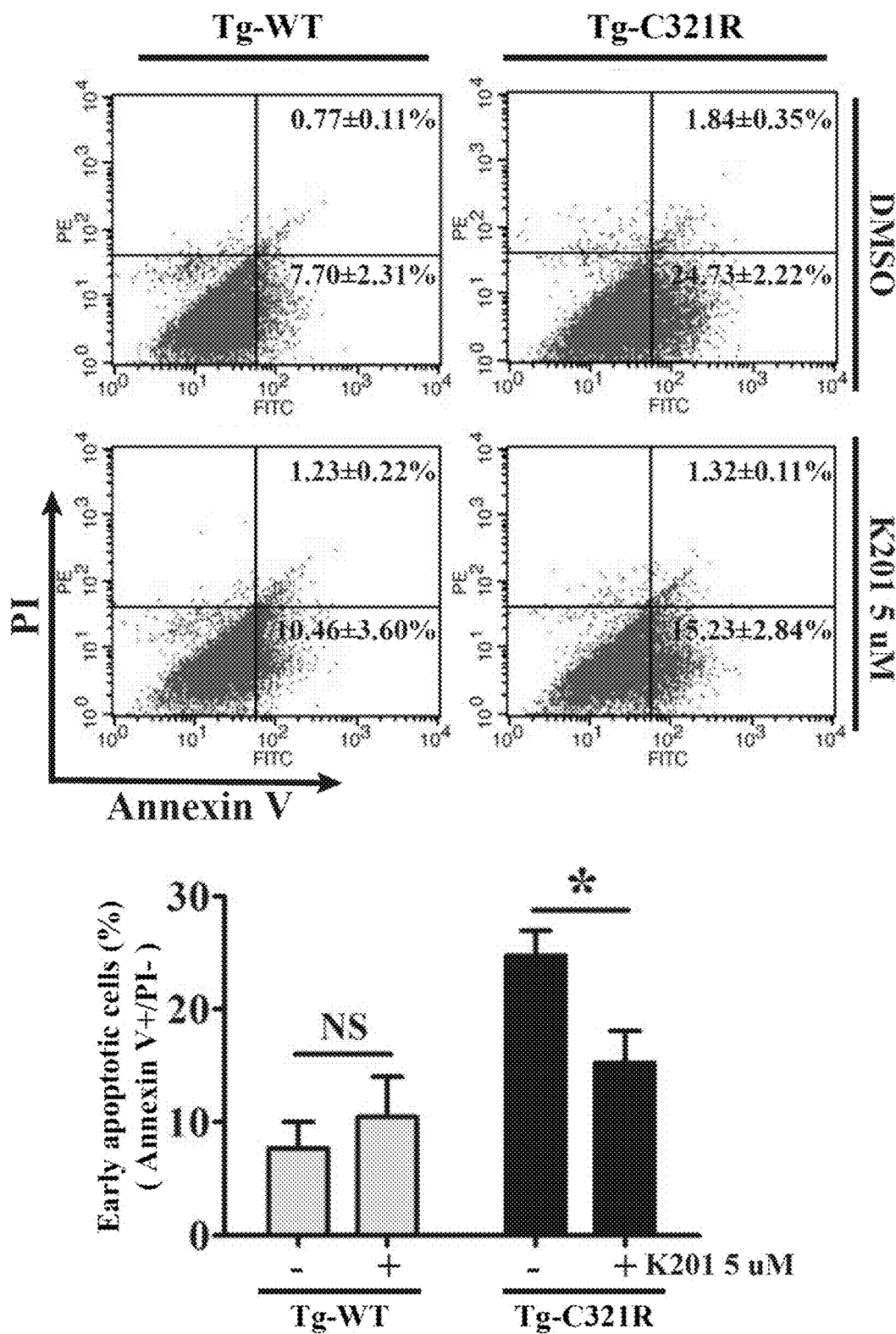
Figure 8:
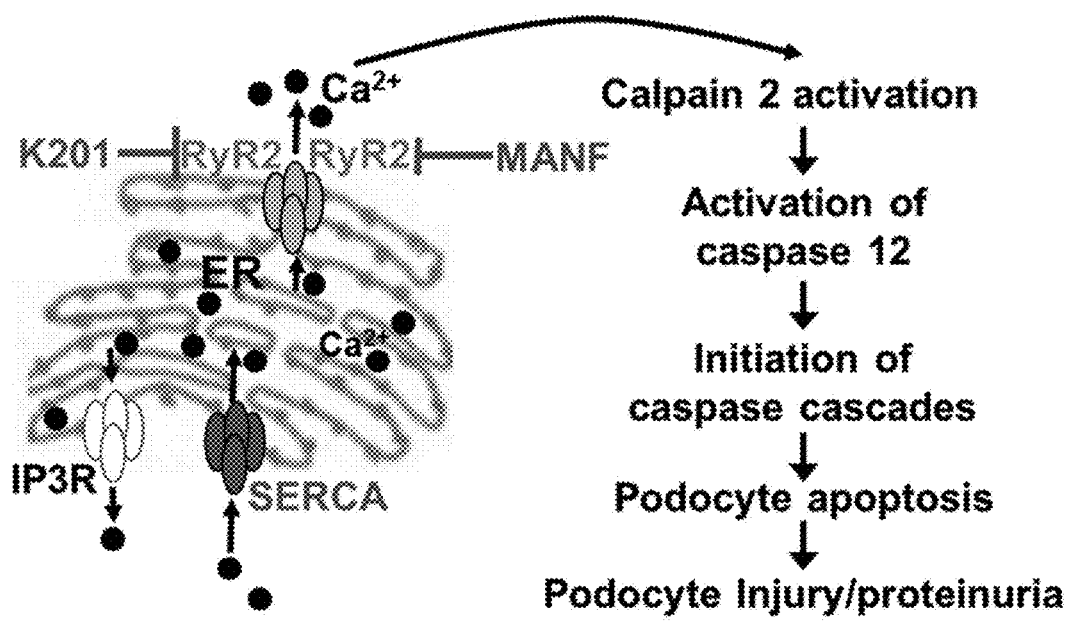
FIG. 8. Schematic showing K201 and MANF modulate podocyte ER calcium depletion-induced apoptosis and injury.

Calcium in the ER lumen is maintained at concentrations 1000-fold to 10,000-fold greater than in the cytoplasm by the sarco/endoplasmic reticulum $Ca^{2+}$ ATPase (SERCA), a pump for uphill transport of $Ca^{2+}$ ions from the cytoplasm into the ER lumen (see e.g., FIG. 8). Thapsigargin (TG), an irreversible SERCA inhibitor, blocks ER calcium uptake from cytosol. The majority of calcium efflux from the ER is mediated by ryanodine receptor (RYR) and inositol 1, 4, 5-triphosphate receptor (IP3R) channels. FIG. 5B directly demonstrated that phosphorylation of RyR2 at Ser 2808 is a molecular mechanism mediating enhanced ER calcium efflux under ER stress.

Identification of MANF as a Treatment to Inhibit Podocyte ER Stress-Mediated Apoptosis MANF has a cytoprotective role against ER stress-mediated apoptosis. MANF treatment attenuated ER calcium release and cytosolic calcium levels in Tg-C321R cells (see e.g., FIG. 7A), inhibited calpain 2-caspase 12 activation (see e.g., FIG. 7C and FIG. 7D) via reducing phosphorylation of RyR2 (see e.g., FIG. 7B). MANF treatment also suppresses apoptosis in Tg-C321R podocytes (see e.g., FIG. 7F) through inhibition of both caspase 12 and CHOP (see e.g., FIG. 7D).

Figure 22:
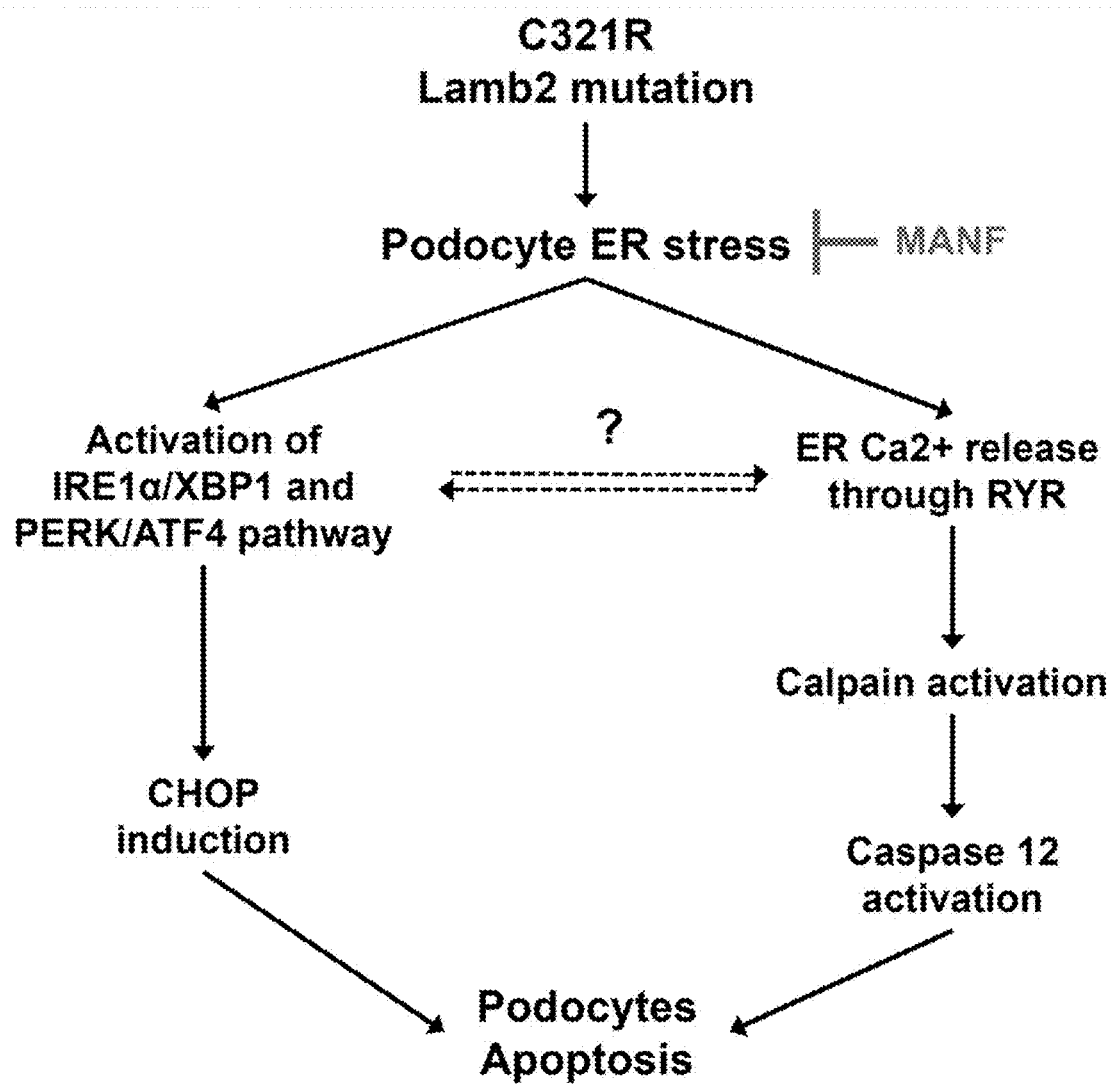
FIG. 22. Schematic showing how the C321R mutation results in podocyte ER stress and apoptosis, which can be inhibited by MANF.
Figure 23:
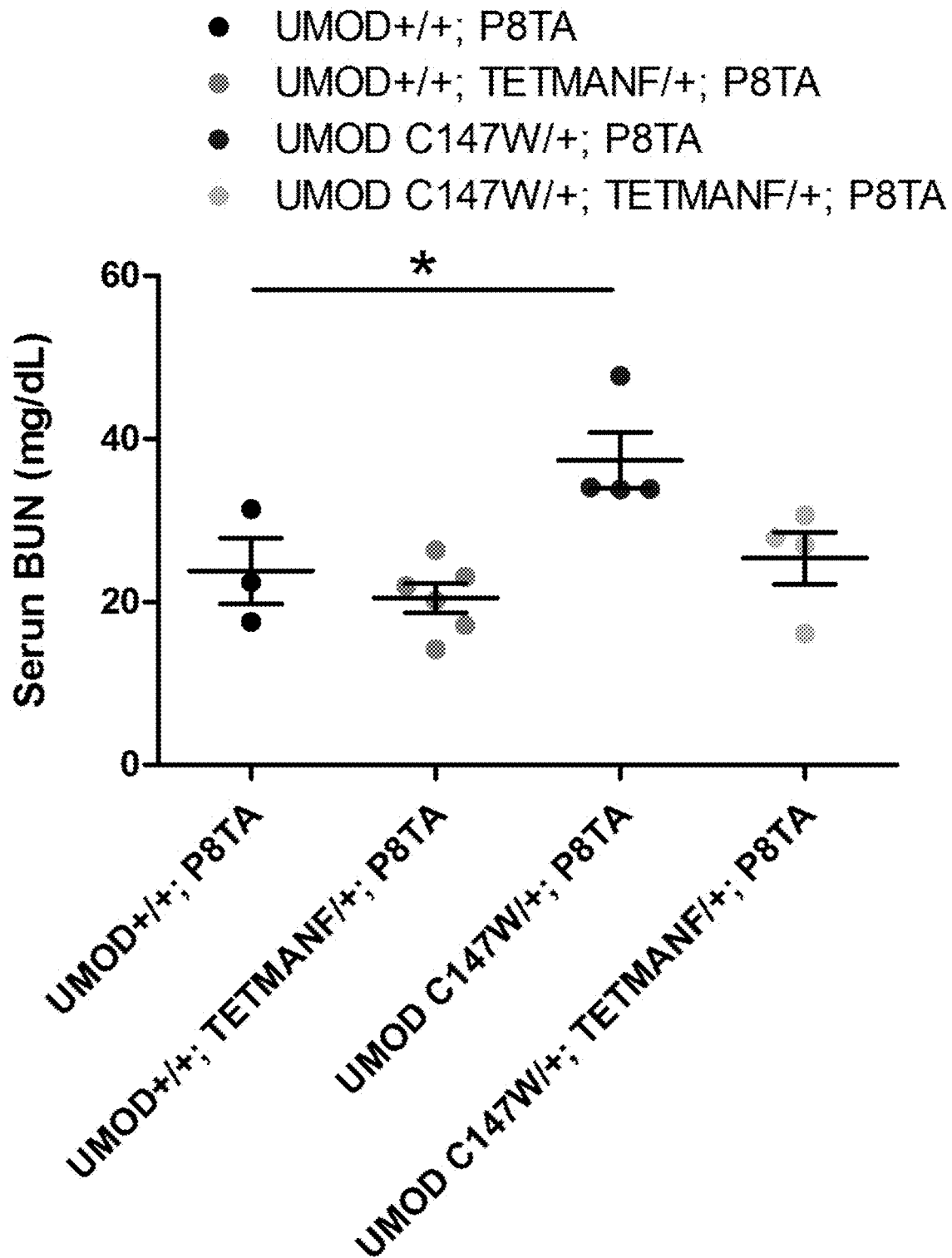
FIG. 23. Plot showing MANF treatment improved the kidney function in Umod C147W/+ mice.

In summary, the rescue effects of MANF on podocytes undergoing ER stress are shown here (see e.g., FIG. 22).

Example 3: Developing a Novel Treatment for Er Stress-Mediated Monogenic Kidney Diseases The following example describes the novel use of MANF to treat ER stress-mediated monogenic kidney diseases.

Summary

The overall goal of the study is to investigate the therapeutic significance of a newly identified endoplasmic reticulum (ER) soluble protein mesencephalic astrocyte-derived neurotrophic factor (MANF) in the treatment of ER stress-mediated monogenic kidney diseases. Currently there is no treatment targeting ER stress, which underlies the pathogenesis of various kidney diseases. This example demonstrates that MANF can antagonize ER stress-mediated apoptosis in kidney cells. A successful completion of this study will enable the treatment of both hereditary and acquired kidney diseases caused by ER dysfunction.

Scientific Rationale and Background

The advent of next-generation sequencing in recent years has led to a rapid discovery of novel or rare genetic variants in human kidney cell genes, which is transforming the risk assessment, diagnosis, and treatment of monogenic kidney diseases. Mutations may lead to protein misfolding, disruption of protein trafficking and ER retention. An imbalance between the load of misfolded proteins and the folding capacity of the ER causes ER stress and unfolded protein response (UPR). Mounting evidence has demonstrated that ER stress and dysfunction induced by genetic mutations play a causative role in the pathogenesis of genetic disorders, including neurodegenerative disease, monogenic diabetes, and monogenic kidney disease. Currently there is no mechanism-based treatment for monogenic kidney diseases. Here, two prototypical ER stress-induced genetic kidney diseases, hereditary nephrotic syndrome (NS) caused by podocyte ER stress and autosomal dominant tubulointerstitial kidney disease (ADTKD) caused by tubular ER stress are highlighted.

The UPR is initiated by three ER transmembrane proteins, PERK, IRE1, and ATF6. BiP is a key sensor linked to the UPR in the stressed cells. PERK phosphorylates eukaryotic initiation factor-2 α (eIF2α), leading to attenuation of protein translation and induction of activating transcription factor 4 (ATF4). IRE1 is a dual activity enzyme with an endoribonuclease and a kinase domain. IRE1-mediated cleavage of XBP1 leads to a spliced XBP1 mRNA (XBP1s), encoding a potent transcriptional activator. IRE1 also recruits TRAF2 and activates both Jun N-terminal kinase (JNK) and caspase 12, thus transmitting apoptotic signals. ATF6 activates transcription of chaperones after being cleaved in Golgi from 90 kDa to the active 50 kDa ATF6 (p50ATF6). Thus, ATF4, XBP1s, and p50ATF6 are three master transcription factors mediating ER signaling cascades. Cells rendered dysfunctional due to severe or prolonged ER stress are eliminated from the organism by ER stress-specific apoptosis, mediated by caspase 12, JNK, or C/EBP homologous protein (CHOP). ER stress-induced ER calcium efflux to the cytosol also contributes to apoptosis. The increase in the cytosolic free calcium activates calcium-dependent protease calpain 2, which cleaves and activates ER localized procaspase 12. Activated caspase 12 further cleaves downstream executioner caspases.

Primary NS is one of the leading causes of chronic kidney disease (CKD), afflicting more than 500 million people worldwide and increasing in prevalence. It is characterized by heavy proteinuria, accompanied by increased risk of infection and venous thrombosis. Almost 100% of patients with congenital onset and 44% with infantile onset of NS have gene mutations with the overall mutation detection rate being as high as 52% in steroid-resistant pediatric NS patients. Seminal advances in past decades have identified NS as a primary podocytopathy with major discoveries of podocyte-specific gene mutations in human NS patients, including NPHS1, NPHS2, LAMB2, ACTN4, and COL4A encoding nephrin, podocin, laminin P2, α-actinin 4, and collagen IV a chain, respectively. In cell culture studies, certain NS-causing nephrin or podocin missense mutants are trapped inside the ER and activate ER stress. In mouse models, it has been demonstrated that podocyte ER stress induced by pathogenic mutations LAMB2 C321R, ACTN4 K256E, or COL4A3 G1332E leads to podocyte injury and NS. In human studies, multiple COL4A mutations, the most frequent mutations underpinning adult steroid-resistant NS or Alport syndrome (AS), activate the UPR in podocytes.

ADTKD is a monogenic form of renal tubulointerstitial fibrosis, leading to CKD. ADTKD represents as many as 25% of patients with inherited kidney disease, after exclusion of polycystic kidney disease and AS. ADTKD is caused by mutations in UMOD, MUC1, REN, and HNF1B, and its prevalence may have been underestimated due to the lack of distinctive clinical phenotype and diagnostic tests. Uromodulin encoded by UMOD is exclusively expressed in the thick ascending limb (TAL) tubular epithelial cells. Multiple studies have shown that UMOD mutations induce ER stress in TAL, leading to TAL damage, inflammation and fibrosis.

Despite the importance of ER stress and dysfunction in monogenic kidney diseases, there is no treatment that targets the ER due to lack of molecules rescuing ER stress-mediated cell death. Here, the therapeutic application of a novel protein MANF for the treatment of ER disease is investigated by taking advantage of the strong power of monogenic etiology of podocyte ER stress-induced NS and tubular ER stress-induced renal fibrosis, respectively. The results obtained from studies of highly penetrant monogenic diseases, which are more amenable to teasing out the molecular pathogenesis and discovery of drugs, can also be leveraged for the development of new therapeutic approaches to more prevalent acquired forms of NS or fibrosis, which may share the same "druggable" ER stress pathways.

Biotherapeutic Candidate

MANF, an 18 kDa soluble protein localizing to the luminal ER, is a recently identified human ER stress inducible and secreted protein that can promote cell survival and antagonize ER stress-mediated inflammation or apoptosis in various organs. In animal models, it can protect and repair midbrain dopaminergic neurons in Parkinson's disease, protect cardiac myocytes against myocardial infarction, reduce cortical neuron injury in ischemic stroke, and promote the survival of pancreatic p cells in diabetes. However, the biological function of this protein in renal diseases has not been studied previously.

A monogenic podocyte ER stress-induced NS mouse model has been developed carrying the C321R mutation in the glomerular basement membrane constituent LAMB2, which is synthesized and secreted by podocytes. It has been shown that in Lamb2-; NEPH-Tg-WT mice, transgenic (Tg) expression of the wild type (WT) P2 cDNA in podocytes via the podocyte-specific mouse nephrin promoter (NEPH) on the Lamb2-, background is sufficient to prevent proteinuria in Lamb2$^{-/-}$ mice. It has also been shown that Lamb2$^{-/-}$ mice expressing C321R-LAMB2 in podocytes (Lamb2$^{-/-}$; NEPH-Tg-C321R) recapitulate features of human NS patients carrying the C321R-LAMB2 mutation. For simplicity, Lamb2$^{-/-}$; NEPH-Tg-C321R and Lamb2$^{-/-}$; NEPHTg-WT mice will hereafter be referred to as Tg-C321R and Tg-WT mice, respectively. Tg-C321R mice exhibit LAMB2 transcript levels in podocytes comparable to those in Tg-WT and WT littermates. In the first postnatal month when Tg-C321R mutants exhibit trace proteinuria without notable renal histological alternations, podocyte ER stress induced by the C321R mutant protein is evident. At 6-8 weeks of age, the mutant mice exhibit focal segmental glomerulosclerosis (FSGS) and overt proteinuria and die around 12 weeks. In this podocyte ER stress model, it has been demonstrated that activation of caspase 12 and CHOP, but not JNK, at an early stage of the disease mediates podocyte injury and subsequent development of NS.

Primary podocytes, which were isolated and cultured from Tg-WT and Tg-C321 mice at P27, were treated with recombinant protein MANF for 24 h. Treatment with MANF significantly suppressed the upregulation of ATF4 and XBP1s in Tg-C321R podocytes compared to Tg-WT podocytes (see e.g., FIG. 7E). When cytosolic calcium levels in MANF-treated and untreated podocytes were measured by cell-permeant cytosolic calcium indicator Fluo-4, MANF markedly blocked the accelerated podocyte ER-to-cytosol calcium efflux in the mutant podocytes relative to control podocytes (see e.g., FIG. 7A). Consequently, MANF treatment inhibited calpain 2 hyperactivation, as indicated by the decreased cleavage of alpha II spectrin, a well characterized substrate for calpain 2, as well as its downstream procaspase 12 activation (cleavage) in Tg-C321R podocytes (see e.g., FIG. 7C and FIG. 7D). Moreover, MANF treatment attenuated CHOP activation in the mutant podocytes (see e.g., FIG. 7D). Ultimately, MANF decreased early apoptosis in Tg-C321R podocytes, as evidenced by flow cytometry analysis of Annexin V+/Propidium Iodide (PI)-podocytes (10.73% before vs 17.27% after treatment) (see e.g., FIG. 7F). Collectively, these data convincingly demonstrate that MANF ameliorates ER stress and protects against ER stress-specific apoptosis.

Umod C147W/+ mice that recapitulate ADTKD patients carrying the corresponding mutation have also been obtained. In this mouse model, caspase 12 and CHOP are activated by the mutation-induced tubular ER stress, resulting in TAL injury, inflammation, and renal fibrosis with the full-blown disease at 24 weeks.

Conditional renal tubular-specific MANF transgenic mice have been generated. TET-MANF mice were crossed with renal tubular-specific rtTA (Pax8-rtTA; P8TA) mice to generate bitransgenic TETMANF/+; P8TA mice, which were further bred to Umod C147W mice to generate Umod C147W/+; TETMANF/+; P8TA and Umod C147W/+; P8TA mice. Meanwhile, control Umod$^{+/+}$; TETMANF/+; P8TA and Umod$^{+/+}$; P8TA littermates were also generated. By administrating DOX, MANF expression was induced in renal tubules of Umod C147W/+; TETMANF/+; P8TA mice and control Umod$^{+/+}$; TETMANF/+; P8TA mice starting at 6 weeks of age until 24 weeks of age. Meanwhile, single transgenic mice including Umod C147W/+; P8TA and Umod$^{+/+}$; P8TA treated with DOX for the same duration were also included as controls. As shown in FIG. 24, MANF treatment improved the kidney function in Umod C147W/+ mice, as evidenced by the decrease of BUN levels in DOX treated-Umod C147W/+; TETMANF/+; P8TA mice compared with DOX treated-Umod C147W/+; P8TA mice.

First Biological Readout in Clinic

The agent, MANF, is indicated to treat ER stress-mediated monogenic kidney diseases. In addition, MANF may also be applied to much more prevalent sporadic forms of nephrotic syndrome (NS), including podocyte ER stress-mediated diabetic nephropathy and Focal Segmental Glomerulosclerosis (FSGS) that are leading causes of NS and chronic kidney disease (CKD), and to acquired forms of renal fibrosis arising from tubular ER stress. Proteinuria and kidney function will be assessed longitudinally before, during and after the treatment in NS patients. In addition, a large genotyped ADTKD-UMOD cohort has been assembled in the US and these 329 patients with well-annotated clinical information can be enrolled as the first clinical study to demonstrate proof of mechanism. Recently, it has been discovered that CRELD2 is a urinary ER stress biomarker in both mouse models and human patients, including ADTKD-UMOD. This study will monitor urine CRELD2 levels before, during, and after the treatment. Other urinary renal fibrosis biomarkers, including epidermal growth factor (EGF) will also be measured in serial urine collections.

Research Plan and Reagents

Based on strong preliminary data, the hypothesis is that treatment of ER-stressed kidney cells with MANF can antagonize ER stress-mediated apoptosis, thereby mitigating proteinuria in hereditary NS or renal fibrosis in ADTKD. To accomplish these research goals, the following will be completed.

(1) Investigate Whether MANF Treatment Ameliorates Proteinuria in Podocyte ER Stress-Induced NS.

Experimental Design 1. Generate conditional podocyte-specific MANF transgenic mice. The doxycycline (DOX)-inducible MANF transgenic (TET-MANF) mice and podocyte-specific reverse tetracycline-controlled transcriptional activator (rtTA) (nephrin-rtTA; NEFTA) driver mice are available. In the presence of DOX, MANF will be induced specifically in podocytes in bitransgenic NEFTA/+; MANF/+(abbreviated to NEFTA/MANF) mice. NEFTA/MANF mice will be further bred to Tg-C321R mice to generate Tg-C321R; NEFTA/MANF mice. Meanwhile, Tg-WT; NEFTA/MANF mice will also be generated as controls. By using DOX as a genetic switch, MANF expression will be upregulated in podocytes starting at 3 weeks of age for 10 weeks or longer in different genotypes.

Experimental Design 2. Determine if podocyte-specific MANF overexpression ameliorates ER stress and proteinuria in Tg-C321R mice. Tg-C321R; NEFTA/MANF and age-matched Tg-WT; NEFTA/MANF mice treated with or without DOX will be employed to test the therapeutic effect of MANF. Urine, blood, kidneys, glomeruli, and podocytes will be harvested at 3, 6, and 12 weeks.

The following assays will be performed to characterize the phenotype on the above mice: serial urine collections for monitoring spot albumin and CRELD2 to Cr ratios by ELISA; serial serum collections for checking kidney functions (serum BUN and Cr) and albumin; and HE, PAS, Trichrome, and Transmission electron microscopy (TEM) for examining kidney histopathology and ultrastructural changes of the glomerular filtration barrier. Severity of the glomerulosclerosis will be graded based on a scale of 0-4. Dual immunofluorescence (IF) staining of TUNEL (terminal deoxynucleotidyl transferase dUTP nick end labeling) and the podocyte nucleus marker WT-1 will be performed to compare podocyte apoptosis among the different groups at the indicated time points. WT-1 staining will also be used to quantify average podocyte numbers per glomerulus among the different genotypes. RNA and protein will be obtained from both glomeruli and primary podocytes of the indicated groups at the different time points. ER stress-mediated apoptotic pathways including calpain2-caspase 12 and CHOP, as well as downstream targets, including caspases 9 and 3, Bax, Bak, and Bcl-2, will be studied at both transcriptional and translational levels.

(2) Determine Whether MANF Treatment Suppresses Renal Fibrosis in Tubular ER Stress Induced ADTKD.

Experimental Design. Determine if tubular-specific MANF overexpression inhibits ER stress and renal fibrosis in Umod C147w/+ mice. Umod C147W/+; TET/MANF/+; P8TA, Umod C147W/+; P8TA, Umod$^{+/+}$; TET/MANF/+; P8TA and Umod$^{+/+}$; P8TA littermates treated with or without DOX will be employed in the study. Urine, blood, and kidneys will be collected at 6, 12, 16, and 24 weeks. The following assays will be performed to characterize the phenotype on the above mice: serial urine collections for CRELD2 to Cr ratios by ELISA; serial serum collections for checking kidney functions; and HE, PAS, Trichrome, and Sirius red staining for examining kidney histopathology and fibrosis. RNA and protein will be extracted from kidneys of the indicated groups at the different time points. ER stress-mediated apoptotic pathways including caspase 12 and CHOP, ER stress-mediated inflammation, as well as renal fibrosis will be studied to determine whether MANF can protect Umod C147W/+ kidneys against ER stress-mediated inflammation and fibrosis.

What is claimed is:

1. A method of treating a subject in need thereof having an endoplasmic reticulum (ER) stress-mediated kidney disease comprising: administering a therapeutically effective amount of a pharmaceutical composition comprising K201 or mesencephalic astrocyte-derived neurotrophic factor (MANF) to the subject.

2. The method of claim 1, wherein the therapeutically effective amount of K201 or MANF is an amount sufficient to reduce apoptosis and injury in podocytes or tubular cells or to stabilize ER calcium channels in podocytes or tubular cells, compared to a control or the subject prior to administration of K201 or MANF.

3. The method of claim 1, wherein the therapeutically effective amount of K201 or MANF reduces RyR2 phosphorylation in podocytes or reduces calcium leaks in ER-stressed podocytes or tubular cells.

4. The method of claim 1, wherein the therapeutically effective amount of K201 or MANF: inhibits ER stress-mediated pro-apoptotic pathways, suppressing ER stress-induced apoptosis; inhibits ER stress-induced calcium efflux from the ER to cytosol in kidney cells; inhibits ER calcium depletion; inhibits albuminuria; decreases urinary calpain activity; corrects leaky RyR2 calcium channels; inhibits podocyte or tubular cell injury; inhibits podocyte or tubular cell apoptosis; or decreases proteinuria, compared to a control or the subject prior to administration of K201 or MAN F.

5. The method of claim 1, wherein K201 or MANF is a podocyte ER calcium channel stabilizing agent.

6. The method of claim 1, wherein
the therapeutically effective amount of MANF is an amount sufficient to reduce RyR2 phosphorylation; block RyR2-Ser2808 phosphorylation-mediated ER calcium depletion, inhibit calpain 2 activation, decrease cleavage of spectrin and talin 1, suppress active cleaved caspase 12, reduce CHOP induction, and reduce early apoptotic rate in podocytes or tubular cells; or the therapeutically effective amount of K201 is an amount sufficient to suppress phosphorylation of RyR2; block RyR2-Ser2808 phosphorylation-mediated ER calcium depletion; decrease proteinuria; or block or inhibit podocyte injury in ER-stressed podocytes.

7. The method of claim 1, wherein the ER stress-mediated kidney disease is selected from the group consisting of: a podocyte ER stress-mediated glomerular disease; a diabetic nephropathy; a primary nephrotic syndrome; renal fibrosis; a tubular ER stress-mediated kidney disease; and chronic kidney disease caused by an ER stress-mediated kidney disease.

8. The method of claim 7, wherein
(i) the primary nephrotic syndrome is selected from the group consisting of: focal segmental glomerulosclerosis (FSGS), membranous nephropathy (MN), and minimal change disease (MCD);
(ii) the podocyte ER stress-mediated glomerular disease is selected from the group consisting of: minimal change disease (MCD), focal segmental glomerulosclerosis (FSGS), membranous nephropathy (MN), hereditary nephrotic syndrome, sporadic nephrotic syndrome, diabetic nephropathy (DN), Alport syndrome, chronic kidney disease (CKD) caused by nephrotic syndrome (NS), and podocyte ER stress-mediated diabetic nephropathy (DN); or
(iii) the tubular ER stress-mediated disease is selected from the group consisting of: autosomal dominant tubulointerstitial kidney disease (ADKTD), ischemic acute kidney injury, autosomal dominant polycystic kidney disease (ADPKD), and renal fibrosis.

9. The method of claim 8, wherein the tubular ER stress-mediated disease is selected from the group consisting of renal fibrosis, autosomal dominant tubulointerstitial kidney disease (ADTKD), ischemic acute kidney injury, and autosomal dominant polycystic kidney disease (ADPKD).

* * * * *